(12) United States Patent
Rharbi et al.

(10) Patent No.: US 11,096,880 B2
(45) Date of Patent: *Aug. 24, 2021

(54) PROCESS FOR DYEING KERATIN FIBRES USING AT LEAST ONE DIRECT DYE AND AT LEAST ONE DISULFIDE, THIOL OR PROTECTED-THIOL FLUORESCENT DYE

(71) Applicant: L'OREAL, Paris (FR)

(72) Inventors: Samira Rharbi, Saint-Ouen (FR); Melanie Bellet, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/622,264

(22) PCT Filed: Jun. 18, 2018

(86) PCT No.: PCT/EP2018/066114
§ 371 (c)(1),
(2) Date: Dec. 12, 2019

(87) PCT Pub. No.: WO2018/229295
PCT Pub. Date: Dec. 20, 2018

(65) Prior Publication Data
US 2020/0100999 A1  Apr. 2, 2020

(30) Foreign Application Priority Data
Jun. 16, 2017  (FR) ...................................... 1755479

(51) Int. Cl.
A61Q 5/10 (2006.01)
A61K 8/49 (2006.01)
A61Q 5/06 (2006.01)

(52) U.S. Cl.
CPC .......... *A61K 8/4933* (2013.01); *A61K 8/4926* (2013.01); *A61K 8/4946* (2013.01); *A61Q 5/065* (2013.01); *A61K 2800/434* (2013.01); *A61K 2800/4324* (2013.01); *A61K 2800/592* (2013.01)

(58) Field of Classification Search
CPC ........ A61Q 5/065; A61K 8/4926; A61K 8/49; A61K 8/4946; A61K 8/494; A61K 8/355; A61K 2800/432; A61K 2800/88; A61K 8/466; A61K 2800/884; A61K 8/4953; A61K 8/46; A61K 8/4933; A61K /; C09B 53/00; C09B 55/00; C09B 49/00
USPC .......................................................... 8/426
See application file for complete search history.

(56) References Cited

U.S. PATENT DOCUMENTS

| | | |
|---|---|---|
| 3,100,739 A | 8/1963 | Kaiser et al. |
| 3,524,842 A | 8/1970 | Grossmann et al. |
| 3,578,386 A | 5/1971 | Kalopissis et al. |
| 3,617,163 A | 11/1971 | Kalopissis et al. |
| 3,817,698 A | 6/1974 | Kalopissis et al. |
| 3,869,454 A | 3/1975 | Lang et al. |
| 3,955,918 A | 5/1976 | Lang |
| 4,003,699 A | 1/1977 | Rose et al. |
| 4,025,301 A | 5/1977 | Lang |
| 4,103,145 A | 7/1978 | Oliveri |
| RE30,199 E | 1/1980 | Rose et al. |
| 4,308,878 A | 1/1982 | Silva |
| 4,886,517 A | 12/1989 | Bugaut et al. |
| 5,046,516 A | 9/1991 | Barradas |
| 5,087,733 A | 2/1992 | Deppert et al. |
| 5,494,058 A | 2/1996 | Chan |
| 5,708,151 A | 1/1998 | Mockli |
| 5,879,413 A | 3/1999 | Pengilly et al. |
| 5,888,252 A | 3/1999 | Mockli |
| 5,919,273 A | 7/1999 | Rondeau et al. |
| 5,957,140 A | 9/1999 | McGee |
| 5,983,903 A | 11/1999 | Nanba et al. |
| 5,993,490 A | 11/1999 | Rondeau et al. |
| 6,045,591 A | 4/2000 | Deneulenaere |
| 6,136,042 A | 10/2000 | Maubru |
| 6,179,881 B1 | 1/2001 | Hendon et al. |
| 6,284,003 B1 | 9/2001 | Rose et al. |
| 6,451,069 B2 | 9/2002 | Matsunaga et al. |
| 6,458,167 B1 | 10/2002 | Genet et al. |
| 6,730,789 B1 | 5/2004 | Birault et al. |

(Continued)

FOREIGN PATENT DOCUMENTS

| | | |
|---|---|---|
| CN | 103327953 A | 9/2013 |
| DE | 2359399 A1 | 6/1975 |

(Continued)

OTHER PUBLICATIONS

International Search Report for counterpart Application No. PCT/EP2018/066115, dated Sep. 3, 2018.
International Search Report for counterpart Application No. PCT/EP2018/066114, dated Sep. 3, 2018.
Zviak, Charles, "Science Des Traitements Capillaires," [Hair Treatment Science], published by Masson, 1988, pp. 214-279.
Non-Final Office Action for copending U.S. Appl. No. 16/622,258, dated Oct. 20, 2020.

(Continued)

*Primary Examiner* — Eisa B Elhilo
(74) *Attorney, Agent, or Firm* — The Marbury Law Group, PLLC

(57) ABSTRACT

The present invention relates to a process for dyeing and/or lightening keratin fibres, in particular human keratin fibres such as the hair, using b) one or more disulfide, thiol or protected-thiol fluorescent direct dyes and a) one or more direct dyes different from b).

The present invention also relates to a cosmetic composition comprising the dyes defined above, and also to a multi-compartment device containing said dyes.

The present invention also relates to the use of the dyes a) and b) for dyeing light or dark keratin fibres, without using an additional dye different from those defined above, for giving the fibres very chromatic, particularly visible colours.

19 Claims, No Drawings

(56) References Cited

U.S. PATENT DOCUMENTS

| | | |
|---|---|---|
| 6,797,013 B1 | 9/2004 | Lang et al. |
| 6,863,883 B1 | 3/2005 | Tsujino et al. |
| 7,717,964 B2 | 5/2010 | Daubresse et al. |
| 7,744,657 B2 | 6/2010 | Greaves et al. |
| 7,780,743 B2 | 8/2010 | Greaves et al. |
| 8,038,731 B2 | 10/2011 | Daubresse et al. |
| 8,840,684 B2 | 9/2014 | Greaves |
| 9,265,705 B2 | 2/2016 | Guerin et al. |
| 2006/0080791 A1 | 4/2006 | Daubresse et al. |
| 2009/0313769 A1* | 12/2009 | Daubresse ........... A61K 8/4933 8/406 |
| 2010/0000029 A1 | 1/2010 | Eliu et al. |
| 2013/0227797 A1* | 9/2013 | Greaves ................ A61Q 5/10 8/405 |
| 2013/0283544 A1 | 10/2013 | Greaves |
| 2014/0075687 A1* | 3/2014 | Guerin .................. A61K 8/49 8/405 |
| 2014/0259454 A1 | 9/2014 | Couroux et al. |
| 2015/0101132 A1 | 4/2015 | David et al. |
| 2015/0265513 A1 | 9/2015 | Degeorge et al. |
| 2020/0179255 A1 | 6/2020 | David et al. |
| 2020/0261340 A1 | 8/2020 | Blaise et al. |
| 2020/0337973 A1 | 10/2020 | Blaise et al. |

FOREIGN PATENT DOCUMENTS

| | | |
|---|---|---|
| DE | 2527638 A1 | 5/1976 |
| DE | 2538363 A1 | 5/1976 |
| DE | 4137005 A1 | 5/1993 |
| DE | 4220388 A1 | 12/1993 |
| EP | 0714954 A2 | 6/1996 |
| EP | 0770375 A1 | 5/1997 |
| EP | 0850636 A1 | 7/1998 |
| EP | 0850637 A1 | 7/1998 |
| EP | 0860636 A1 | 8/1998 |
| EP | 0918053 A1 | 5/1999 |
| EP | 0920856 A1 | 6/1999 |
| EP | 1062940 A1 | 12/2000 |
| EP | 1133975 A2 | 9/2001 |
| EP | 1133976 A2 | 9/2001 |
| EP | 1386916 A1 | 2/2004 |
| EP | 1647580 A1 | 4/2006 |
| EP | 2004759 A2 | 12/2008 |
| EP | 2070988 A2 | 6/2009 |
| EP | 2075289 A1 | 7/2009 |
| FR | 1221122 A | 5/1960 |
| FR | 1516943 A | 3/1968 |
| FR | 1540423 A | 9/1968 |
| FR | 1560664 A | 3/1969 |
| FR | 1567219 A | 5/1969 |
| FR | 2189006 A1 | 1/1974 |
| FR | 2275462 A1 | 1/1976 |
| FR | 2285851 A1 | 4/1976 |
| FR | 2570946 A1 | 4/1986 |
| FR | 2757385 A1 | 6/1998 |
| FR | 2788433 A1 | 7/2000 |
| FR | 2801308 A1 | 5/2001 |
| FR | 2920779 A1 | 3/2009 |
| FR | 2920780 A1 | 3/2009 |
| FR | 2921256 A1 | 3/2009 |
| FR | 2921379 A1 | 3/2009 |
| FR | 2968954 A1 | 6/2012 |
| GB | 738585 A | 10/1955 |
| GB | 1163385 A | 9/1969 |
| GB | 1195386 A | 6/1970 |
| GB | 1514466 A | 6/1978 |
| JP | 2006-111626 A | 4/2006 |
| JP | 2010-501032 A | 1/2010 |
| JP | 2014-501339 A | 1/2014 |
| WO | 93/16991 A1 | 9/1993 |
| WO | 95/01772 A1 | 1/1995 |
| WO | 95/15144 A1 | 6/1995 |
| WO | 96/15765 A1 | 5/1996 |
| WO | 97/44004 A1 | 11/1997 |
| WO | 99/48465 A1 | 9/1999 |
| WO | 01/66646 A1 | 9/2001 |
| WO | 03/029359 A1 | 4/2003 |
| WO | 2004/039771 A1 | 5/2004 |
| WO | 2005/097051 A2 | 10/2005 |
| WO | 2006/136617 A2 | 12/2006 |
| WO | 2007/110531 A2 | 10/2007 |
| WO | 2007/110532 A2 | 10/2007 |
| WO | 2007/110533 A2 | 10/2007 |
| WO | 2007/110534 A2 | 10/2007 |
| WO | 2007/110535 A2 | 10/2007 |
| WO | 2007/110536 A2 | 10/2007 |
| WO | 2007/110537 A2 | 10/2007 |
| WO | 2007/110538 A2 | 10/2007 |
| WO | 2007/110539 A2 | 10/2007 |
| WO | 2007/110540 A2 | 10/2007 |
| WO | 2007/110541 A2 | 10/2007 |
| WO | 2007/110542 A2 | 10/2007 |
| WO | 2008/019977 A2 | 2/2008 |
| WO | 2009/034059 A2 | 3/2009 |
| WO | 2009/037325 A2 | 3/2009 |
| WO | 2009/040354 A1 | 4/2009 |
| WO | 2017/081314 A1 | 5/2017 |
| WO | 2018/206661 A1 | 11/2018 |
| WO | 2018/229296 A1 | 12/2018 |

OTHER PUBLICATIONS

International Search Report and Written Opinion for counterpart Application No. PCT/EP2018/062038, dated Jun. 25, 2018.
Ashford's Dictionary of Industrial Chemicals, Second Edition, 2001, pp. 14-39.
Greene, T.W., "Protective Groups in Organic Synthesis," John Wiley & Sons, ed., NY, 1981, pp. 193-217.
Kirk-Othmer Encyclopedia of Chemical Technology, "Hair Preparation," 4th Ed., vol. 12, 1994, p. 881-918.
Kocienski, P., "Thiol Protecting Groups," Thieme 3rd Ed., 2005, Chapter 5.
Ullmann's Encyclopedia of Industrial Chemistry, "Hair Preparation," 2002, DOI: 10.1002114356007.a12_571.
Ullmann's Encyclopedia, "Peptide Synthesis," pp. 4-5, 2005, Wiley-VCH Verlag GmbH & Co. KGaA, Weinheim 10.1002/14356007.a19 157.
International Search Report for counterpart Application No. PCT/EP2016/077555, dated Jan. 2, 2017.
Translated Notice of Reasons for Refusal for counterpart JP Application No. 2018-523810, dated May 27, 2019.
Translation of Chinese Office Action for counterpart Application No. 201680065233.7, dated Jul. 28, 2020.
Non-Final Office Action for copending U.S. Appl. No. 15/774,733, dated Feb. 24, 2021.
Hegazy, M.A. et al., "Novel Cationic Gemini Surfactants as Corrosion Inhibitors for Carbon Steel Pipeline," Corrosion Science, vol. 52, Issue 9, (2010), pp. 2897-2904.
Non-Final Office Action for copending U.S. Appl. No. 16/611,437, dated Apr. 27, 2021.
Final Office Action for copending U.S. Appl. No. 16/622,258, dated May 11, 2021.

* cited by examiner

PROCESS FOR DYEING KERATIN FIBRES USING AT LEAST ONE DIRECT DYE AND AT LEAST ONE DISULFIDE, THIOL OR PROTECTED-THIOL FLUORESCENT DYE

CROSS REFERENCE TO RELATED APPLICATION

This is a national stage application of PCT/EP2018/066114, filed internationally on Jun. 18, 2018, which claims priority to French Application No. 1755479, filed on Jun. 16, 2017, both of which are incorporated by reference herein in their entireties.

The present invention relates to a process for dyeing and/or lightening keratin fibres, in particular human keratin fibres such as the hair, using b) one or more disulfide, thiol or protected-thiol fluorescent direct dyes and a) one or more direct dyes different from b).

The present invention also relates to a cosmetic composition comprising the dyes defined above, and also to a multi-compartment device containing said dyes.

The present invention also relates to the use of the dyes a) and b) for dyeing light or dark keratin fibres, without using additional dye different from those defined above, for conferring very chromatic, particularly visible colours on the keratin fibres.

Many people have sought for a long time to modify the colour of their hair and in particular to mask their grey hair.

It is especially known practice to dye keratin fibres, in particular human keratin fibres, with dye compositions containing oxidation dye precursors, which are generally known as oxidation bases. These oxidation bases are colourless or weakly coloured compounds, which, when combined with oxidizing products, may give rise to coloured compounds via a process of oxidative condensation.

The shades obtained with these oxidation bases may be modified by combining them with couplers or colour modifiers. The variety of molecules used as oxidation bases and couplers allows a wide range of colours to be obtained.

Another well-known method consists in obtaining "semi-permanent" dyeing by applying to the keratin fibres direct dyes, which are coloured and colouring molecules that have affinity for said fibres.

The direct dyes conventionally used are chosen from nitrobenzene, anthraquinone, nitropyridine, azo, xanthene, acridine, azine and triarylmethane direct dyes. The chemical species may be non-ionic, anionic (acidic dyes) or cationic (basic dyes). The direct dyes may also be natural dyes.

Conventional direct dyeing processes consist in applying to keratin fibres dye compositions comprising direct dyes. After application, a leave-on time is observed so as to allow the dyeing molecules to penetrate by diffusion into the fibres. On conclusion of the process, the fibres are rinsed.

In contrast with oxidation dyeing, these direct dyeing processes have a tendency to better protect the integrity of the fibres. The resulting colourings are generally chromatic, but, however, are only semi-temporary. The nature of the interactions that bind the direct dyes to the keratin fibres and their desorption from the surface and/or the core of the fibre are responsible for their weak dyeing power.

Although a wide range of colours is currently accessible, it generally proves necessary to combine three dyes of complementary colours—trichromatic principle—in order to obtain a natural shade (see, for example, WO 95/15144 and WO 95/01772). This tripartite combination does not, however, show good persistence with respect to repeated shampooing. It generally, or even systematically, induces an unaesthetic changing of the colour, which the consumer finds dissuasive.

These colourings are furthermore not sufficiently fast in the face of external agents such as light or perspiration.

Thus, there is a real need to implement processes for the direct dyeing of keratin materials, in particular of keratin fibres, in particular human keratin fibres such as the hair, which do not have the drawbacks mentioned above, i.e. which make it possible especially to lead to colourings that have good properties, especially in terms of chromaticity, power, intensity, sheen, selectivity and colour build-up, and which are persistent in particular with respect to shampooing. In addition, it is sought to obtain very chromatic, particularly visible colours while at the same time remaining aesthetic. The fluorescence, associated with these colour effects, can be particularly uniform and amplified, while at the same time remaining aesthetic, under UV radiation.

It is also sought to be able to visibly lighten dark keratin fibres without having recourse to conventional bleaching products which may damage the fibres. The fluorescence, associated with these optical lightening effects, can be particularly uniform and amplified, while at the same time remaining aesthetic, under UV radiation.

Another aim of the present invention is thus to be able to dye and/or lighten dark keratin fibres, in particular human dark keratin fibres such as the hair, preferably only with the two direct dyes a) and b) without necessarily having to add an oxidizing agent.

The applicant has discovered, surprisingly, that a process for dyeing keratin fibres using b) one or more disulfide, thiol or protected-thiol fluorescent dyes and a) one or more direct, in particular ionic, preferably cationic or anionic, dyes different from b) makes it possible to achieve the objectives set out above.

Thus, the main subject of the present invention relates to a process for dyeing keratin fibres, in particular human keratin fibres such as the hair, consisting in applying to said materials:
  a) one or more in particular ionic, direct dyes; and
  b) one or more disulfide, thiol or protected-thiol fluorescent direct dyes;
it being understood that a) the direct dye(s) and b) the disulfide, thiol or protected-thiol fluorescent dyes are applied to said keratin materials jointly or sequentially, and that the dyes a) and b) are distinct.

Another subject of the invention is a cosmetic composition comprising:
  a) one or more in particular ionic, direct dyes;
  b) one or more disulfide, thiol or protected-thiol fluorescent direct dyes;
  c) optionally, one or more reducing agents, and
  d) optionally, the pH of said composition being between 2 and 11 inclusive, preferably between 2.5 and 10.5 inclusive, more preferentially between 3 and 10 inclusive.

The combination of the a) one or more in particular ionic, direct dye(s) and b) one or more disulfide, thiol or protected-thiol fluorescent direct dye(s) makes it possible in particular to obtain colourings which are very chromatic and particularly visible, having good colouring properties, in particular in terms of chromaticity, persistence, power, intensity, sheen and selectivity, in particular on light hair. The combination according to the invention also makes it possible to visibly lighten dark keratin fibres. Furthermore, under UV radiation, the fluorescence phenomenon associated with the colour effects is particularly marked and aesthetic.

Moreover, the colourings obtained by means of the process and the composition according to the invention show good resistance to the various attacking factors to which the hair may be subjected, such as light, bad weather, washing and perspiration. They are in particular persistent with respect to shampooing, especially after at least three shampoo washes.

A subject of the present invention is also a multi-compartment device comprising a first compartment containing one or more in particular ionic, in particular cationic or anionic, direct dye(s) a) as defined above, and a second compartment containing one or more disulfide, thiol or protected-thiol fluorescent dye(s) b) as defined above, it being understood that the dyes a) and b) are distinct.

Another subject of the invention is the use of b) disulfide, thiol or protected-thiol fluorescent direct dye(s) as defined above, combined with the a) in particular ionic, direct dye(s) different from b), for dyeing and/or lightening keratin fibres, preferably human keratin fibres, such as the hair.

The process and the composition of the invention make it possible to obtain, with the fluorescent dyes of the invention, lightening of dark keratin fibres. In particular, the process of the invention makes it possible to obtain visible lightening of keratin fibres such as the hair, which lightening is very fast with respect to shampooing, common attacking factors (sunlight, perspiration) and other hair treatments without degrading the keratin fibre.

For the purposes of the invention, the term "dark keratin fibre" is intended to mean a keratin fibre that has a numerical lightness L* in the CIE system L*a*b*, of less than or equal to 45 and preferably less than or equal to 40, given that, moreover, L*=0 is equivalent to black and L*=100 is equivalent to white.

For the purposes of the invention, the term "dark hair" is intended to mean hair with a tone depth of less than or equal to 6 (dark blond) and preferably less than or equal to 4 (chestnut-brown).

The lightening of hair is evaluated by the "tone depth", which characterizes the degree or level of lightening. The notion of "tone" is based on the classification of natural shades, one tone separating each shade from the shade immediately following or preceding it. This definition and the classification of natural shades are well known to hairstyling professionals and are published in the book "Sciences des traitements capillaires [Hair treatment sciences]" by Charles Zviak, 1988, published by Masson, pp. 215 and 278.

The tone depths range from 1 (black) to 10 (very light blond), one unit corresponding to one tone; the higher the figure, the lighter the shade.

An artificially dyed keratin fibre is a fibre of which the colour has been modified by a dyeing treatment, for example dyeing with direct dyes or oxidation dyes.

The lightening properties of the composition of the invention after application to dark keratin fibres, for example chestnut-brown fibres, may be achieved by reflectance:
the fibres are irradiated with visible light in the wavelength range from 400 to 700 nanometres;
the curves of reflectance as a function of the wavelength, for fibres treated with the composition of the invention and for untreated fibres, are then compared;
the curve corresponding to the treated fibres should show a reflectance in the wavelength range from 450 to 700 nanometres higher than the curve corresponding to the untreated fibres.

This means that, in the wavelength range from 450 to 700 nanometres, there is at least one region in which the reflectance curve corresponding to the treated fibres is higher than the reflectance curve corresponding to the untreated fibres. The term "higher" means a difference in reflectance of at least 0.05% and preferably of at least 0.1%. This does not prevent there from being in the wavelength range from 450 to 700 nanometres at least one region in which the reflectance curve corresponding to the treated fibres is superposable, or lower than the reflectance curve corresponding to the untreated fibres.

Preferably, the wavelength at which the difference is maximal between the reflectance curve for the treated hair and that for the untreated hair is in the wavelength range from 450 to 650 nanometres and preferably in the wavelength range from 450 to 620 nanometres.

Other subjects, characteristics, aspects and advantages of the invention will emerge even more clearly on reading the description and the examples that follow.

For the purposes of the present invention and unless otherwise indicated:
the term "direct dye" means natural and/or synthetic dyes, which are soluble in the cosmetic medium, other than oxidation dyes which absorb colour in the visible spectrum, i.e. which appear to be visually coloured; they are dyes which will diffuse superficially on the keratin fibres;
a direct dye "bearing at least one disulfide function" is a direct dye comprising at least one disulfide bond: —S—S— between two carbon atoms;
a "direct dye bearing at leat one protected-thiol function" is a direct dye comprising at least one protected-thiol function —SY in which Y is a protecting group known to those skilled in the art, for instance those described in the publications "*Protective Groups in Organic Synthesis*", T.W. Greene, John Wiley & Sons ed., NY, 1981, pp. 193-217; "*Protecting Groups*", P. Kocienski, Thieme, 3rd ed., 2005, chap. 5; and Ullmann's Encyclopedia, "*Peptide Synthesis*", pp. 4-5, 2005 Wiley-VCH Verlag GmbH & Co. KGaA, Weinheim 10.1002/14356007.a19 157;
a "direct dye bearing at leat one thiol function" is a direct dye comprising at least one thiol function —SY' in which Y' is i) a hydrogen atom; ii) an alkali metal; iii) an alkaline-earth metal; iv) an ammonium group: $N^+R^aR^bR^gR^d$ or a phosphonium group: $P^+R^aR^bR^gR^d$ with $R^a$, $R^b$, $R^g$ and $R^d$, which may be identical or different, representing a hydrogen atom or a group $(C_1-C_4)$alkyl;
by way of visual colour and absorption wavelength of the direct dyes of the invention associated with said colour, mention may be made of the following colours: "yellow"=$\lambda_{max}$>400 nm up to 440 nm limits included, "orange"=$\lambda_{max}$>440 nm up to 490 nm limits included, "red"=$\lambda_{max}$>490 up to 520 nm limits included, "purple to violet"=$\lambda_{max}$>520 nm and 560 nm limits included, "violet"=$\lambda_{max}$>560 nm to 580 nm limits included, "blue"=$\lambda_{max}$>580 nm up to 620 nm limits included, "blue-green"=$\lambda_{max}$>620 nm up to 650 nm limits included, and "green" $\lambda_{max}$>650 nm up to 780 nm limits included; preferably, the direct dyes a) are yellow, orange, red or blue in colour, and the fluorescent direct dyes b) are preferably yellow, orange or red in colour;
a fluorescent direct dye "bearing a disulfide function" is a direct dye comprising one or more fluorescent chromophores as defined below, and comprising a disulfide bond: —S—S— between two carbon atoms and is preferably indirectly bonded to the chromophore(s) of the dye, i.e. between the chromophores and the SS function there is at least one methylene group;

a "direct dye bearing a protected-thiol function" is a direct dye comprising a chromophore, comprising a protected-thiol function —SY in which Y is a protecting group known to those skilled in the art, for instance those described in the publications "*Protective Groups in Organic Synthesis*", T.W. Greene, John Wiley & Sons ed., NY, 1981, pp. 193-217; "*Protecting Groups*", P. Kocienski, Thieme, 3rd ed., 2005, chap. 5; and Ullmann's Encyclopedia, "*Peptide Synthesis*", pp. 4-5, 2005 Wiley-VCH Verlag GmbH & Co. KGaA, Weinheim 10.1002/14356007.a19 157; it being understood that said protected-thiol function is preferably indirectly bonded to the chromophore of the dye, i.e. between the chromophore and the function —SY there is at least one methylene group;

a "direct dye bearing a thiol function" is a direct dye comprising a chromophore, and comprising a thiol function —SY' in which Y' is i) a hydrogen atom; ii) an alkali metal; iii) an alkaline-earth metal; iv) an ammonium group: $N^+R^aR^bR^gR^d$ or a phosphonium group: $P^+R^aR^bR^gR^d$ with $R^a$, $R^b$, $R^g$ and $R^d$, which may be identical or different, representing a hydrogen atom or a group ($C_1$-$C_4$)alkyl, preferentially comprising a thiol function —SH, it being understood that said thiol function is indirectly bonded to the chromophore of the dye, i.e. between the chromophore and the function —SY' there is at least one methylene group;

a "fluorescent chromophore" is a radical derived from a fluorescent dye, that is to say a radical derived from a molecule which absorbs light in the visible range of radiation which is visually perceptible by human beings and which appears coloured to the naked eye, i.e. which absorbs light at an absorption wavelength $\lambda_{abs}$ preferably between 300 and 700 nm inclusive; said chromophore is also capable of re-emitting in the visible range at an emission wavelength $\lambda_{em}$ greater than the absorption wavelength, i.e. preferably $\lambda_{em}$ re-emitting between 400 and 800 nm inclusive; the difference in the absorption wavelength and emission wavelength, also called Stoke's shift, is between 1 nm and 100 nm inclusive; more preferentially the fluorescent chromophores are capable of absorbing at a wavelength $\lambda_{abs}$ between 420 nm and 550 nm inclusive and of re-emitting in the visible range at a wavelength $\lambda_{em}$ between 470 and 600 nm inclusive;

a "chromophore" is said to be "quaternized cationic" or "bearing a quaternized cationic group" if it comprises in its structure at least one permanent cationic charge formed from at least one quaternized nitrogen atom (ammonium) or quaternized phosphorus atom (phosphonium), preferably nitrogen;

a group is said to be "bearing a quaternizable cationic group" when it comprises at least one tertiary amine or tertiary phosphine at the end of a hydrocarbon-based chain, preferably $C_1$-$C_{10}$ alkyl, such as —(CR'R")$_p$—N(R$_a$)—R$^b$ with R' and R", which may be identical or different, representing a hydrogen atom or a ($C_1$-$C_6$) alkyl group; R$_a$ and R$_b$, which may be identical or different, representing a (poly)(hydroxy)($C_1$-$C_6$)alkyl group or R$_a$ and R$_b$ form, together with the nitrogen atom that bears them, a heterocycloalkyl group such as morpholino, piperidino or piperazino; and p representing an integer between 1 and 10 inclusive; preferably, R' and R" represent a hydrogen atom, R$_a$ and R$_b$ represent a ($C_1$-$C_4$)alkyl group and p is between 2 and 5;

the fluorescent dyes according to the invention contain one or more coloured and fluorescent chromophores as defined previously; they are particularly capable of absorbing light at a wavelength $\lambda_{abs}$ between 300 and 700 nm inclusive and of re-emitting in the visible range at a greater wavelength than the absorption wavelength, in particular $\lambda_{em}$ between 400 and 800 nm inclusive: the difference in the absorption wavelength and emission wavelength, also called Stoke's shift, is between 1 nm and 100 nm inclusive; more preferentially, the fluorescent dyes of the invention are dyes capable of absorbing at a wavelength $\lambda_{abs}$ between 420 nm and 550 nm inclusive and of re-emitting in the visible range at a wavelength $\lambda_{em}$ between 470 and 600 nm inclusive;

the chromophores are said to be "different" when they differ in their chemical structure and may be chromophores derived from different families or from the same family on condition that they have different chemical structures: for example, the chromophores may be chosen from the family of azo dyes but differ in the chemical structure of the radicals constituting them or in the respective position of these radicals;

an "alkylene chain" represents an acyclic hydrocarbon-based divalent chain which is of $C_1$-$C_{20}$, particularly $C_1$-$C_6$, more particularly $C_1$-$C_2$ when the chain is linear; optionally substituted with one or more groups, which may be identical or different, chosen from i) hydroxyl, ii) ($C_1$-$C_2$)alkoxy, iii) (poly)hydroxy($C_2$-$C_4$) alkoxy(di)($C_1$-$C_2$)(alkyl)amino, iv) $R^a$—$Z^a$—$C(Z^b)$—$Z^b$, and v) $R^a$—$Z^a$—$S(O)_t$—$Z^c$ with $Z^a$ and $Z^b$, which may be identical or different, representing an oxygen or sulfur atom, or a group $NR^{a'}$, $Z^c$ representing a bond, an oxygen or sulfur atom, or a group $NR^a$; $R^a$ representing an alkali metal, a hydrogen atom, an alkyl group, or alternatively is absent if another part of the molecule is cationic and $R^{a'}$ representing a hydrogen atom or an alkyl group and t is equal to 1 or 2; more particularly, the groups iv) are chosen from carbon/late —C(O)O$^-$ or —C(O)OMetal (Metal=alkali metal), carboxyl —C(O)—OH, guanidino H$_2$H—C(NH$_2$)—NH—, amidino H$_2$H—C(NH$_2$)—, (thio)ureo H$_2$N—C(O)—NH— and H$_2$N—C(S)—NH—, aminocarbonyl —C(O)—NRa'$_2$ or aminothiocarbonyl —C(S)—NRa'$_2$; carbamoyl Ra'—C(O)—NRa' or thiocarbamoyl Ra'—C(S)—NRa'— with Ra', which may be identical or different, representing a hydrogen atom or a ($C_1$-$C_4$)alkyl group;

an "optionally substituted, saturated or unsaturated $C_1$-$C_{30}$ divalent hydrocarbon-based chain" represents a, particularly $C_1$-$C_8$, hydrocarbon-based chain optionally comprising one or more conjugated or non-conjugated double bonds p, the hydrocarbon-based chain being in particular saturated; said chain is optionally substituted with one or more identical or different groups chosen from i) hydroxyl, ii) ($C_1$-$C_2$)alkoxy, iii) (poly)hydroxy($C_2$-$C_4$)alcoxy (di)($C_1$-$C_2$) (alkyl)amino, iv) $R^a$—$Z^a$—$C(Z^b)$—$Z^c$—, and v) $R^a$—$Z^a$—$S(O)_t$—$Z^c$ with $Z^a$, $Z^b$, which may be identical or different, representing an oxygen or sulfur atom, or a group $NR^{a'}$, $Z^c$ representing a bond, an oxygen or sulfur atom, or a group $NR^a$; $R^a$ representing an alkali metal, a hydrogen atom or an alkyl group or else is absent if another part of the molecule is cationic and $R^{a'}$ representing a hydrogen atom or an alkyl group and t is 1 or 2; more particularly, the groups iv) are chosen from carbon/late —C(O)O⁻ or —C(O)OMetal (Metal=alkali metal), carboxyl —C(O)—OH, guanidino H$_2$H—C(NH$_2$)—NH—, amidino H$_2$H—C(NH$_2$)—, (thio)ureo H$_2$N—C(O)—NH— and H$_2$N—C(S)—NH—, aminocarbonyl —C(O)—NR$_a'_2$ or aminothiocarbonyl —C(S)—NR$_a'_2$; carbamoyl R$_a'$—C(O)—NR$_a'$— or thiocarbamoyl R$_a'$—C(S)—NR$_a'$— with Ra', which may be identical or different, representing a hydrogen atom or a (C$_1$-C$_4$) alkyl group;

the "fluorescent dyes" according to the present invention are to be differentiated from optical brighteners. Optical brighteners, also generally known as "brighteners" or "fluorescent brighteners" or "fluorescent brightening agents" or "fluorescent whitening agents or FWA" or "whiteners" or "fluorescent whiteners", are colourless compounds, which do not impart a colour and are consequently not dyes since they do not absorb in the visible light range, but only absorb in the ultraviolet range (wavelength ranging from 200 to 400 nm) and transform the absorbed energy into fluorescent light of a longer wavelength emitted in the visible part of the spectrum in the blue range. The colour impression is then generated only by the purely fluorescent light that is predominantly blue;

the term "(hetero)aryl" is generally intended to mean aryl and heteroaryl groups;

the "aryl" or "heteroaryl" radicals or the aryl or heteroaryl part of a radical may be substituted with at least one radical borne by a carbon atom, chosen from:
- a C$_1$-C$_6$ and preferably C$_1$-C$_4$ alkyl radical optionally substituted with one or more radicals chosen from hydroxyl, C$_1$-C$_2$ alkoxy, C$_2$-C$_4$ (poly)hydroxyalkoxy, acylamino, amino substituted with two C$_1$-C$_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;
- a halogen atom such as chlorine;
- a hydroxyl or thiol group;
- a C$_1$-C$_6$ alkoxy or C$_1$-C$_6$ alkylthio radical;
- a (poly)hydroxy(C$_2$-C$_6$)alkoxy radical;
- an amino radical;
- a 5- or 6-membered heterocycloalkyl radical, preferentially morpholino, piperazino, piperidino or pyrolidino, which is optionally substituted with a (C$_1$-C$_4$) alkyl radical, preferentially methyl;
- a 5- or 6-membered heteroaryl radical, preferentially imidazolyl, optionally substituted with a (C$_1$-C$_4$) alkyl radical, preferentially methyl;
- an amino radical substituted with one or two identical or different C$_1$-C$_6$ alkyl radicals, optionally bearing at least:
  i) a hydroxyl group,
  ii) an amino group optionally substituted with one or two optionally substituted C$_1$-C$_3$ alkyl radicals, said alkyl radicals possibly forming with the nitrogen atom to which they are attached a saturated or unsaturated, optionally substituted 5- to 7-membered heterocycle, optionally comprising at least one other nitrogen or non-nitrogen heteroatom,
  iii) a quaternary ammonium group —N⁺R'R"R''', Y⁻ for which R', R" and R''', which may be identical or different, represent a C$_1$-C$_4$ alkyl group and Y⁻ represents an anionic counterion,
  iv) or an optionally cationic 5- or 6-membered heteroaryl radical, preferentially imidazolium, optionally substituted with a (C$_1$-C$_4$)alkyl radical, preferentially methyl;
- an acylamino radical (—N(R)—C(O)—R') in which the R radical is a hydrogen atom or a C$_1$-C$_4$ alkyl radical optionally bearing at least one hydroxyl group and the R' radical is a C$_1$-C$_2$ alkyl radical;
- a carbamoyl radical ((R)$_2$N—C(O)—) in which the radicals R, which may be identical or different, represent a hydrogen atom or a C$_1$-C$_4$ alkyl radical optionally bearing at least one hydroxyl group;
- an alkylsulfonylamino radical (R'—S(O)$_2$—N(R)—) in which the R radical represents a hydrogen atom or a C$_1$-C$_4$ alkyl radical optionally bearing at least one hydroxyl group and the R' radical represents a C$_1$-C$_4$ alkyl radical, or a phenyl radical;
- an aminosulfonyl radical ((R)$_2$N—S(O)$_2$—) in which the R radicals, which may be identical or different, represent a hydrogen atom or a C$_1$-C$_4$ alkyl radical optionally bearing at least one hydroxyl group;
- a carboxylic radical in acid or salified form (preferably salified with an alkali metal or an ammonium, which is optionally substituted);
- a cyano group;
- a nitro or nitroso group;
- a polyhaloalkyl group, preferably trifluoromethyl;

the cyclic or heterocyclic part of a non-aromatic radical may be substituted with at least one substituent chosen from the following groups:
- hydroxyl;
- C$_1$-C$_4$ alkoxy, C$_2$-C$_4$ (poly)hydroxyalkoxy;
- C$_1$-C$_4$ alkyl;
- alkylcarbonylamino (R—C(O)—N(R')—) in which the radical R' is a hydrogen atom or a C$_1$-C$_4$ alkyl radical optionally bearing at least one hydroxyl group, and the radical R is a C$_1$-C$_2$ alkyl radical or an amino radical optionally substituted with one or two C$_1$-C$_4$ alkyl groups, which may be identical or different, themselves optionally bearing at least one hydroxyl group, said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;
- alkylcarbonyloxy (R—C(O)—O—) in which the radical R is a C$_1$-C$_4$ alkyl radical or an amino group optionally substituted with one or two identical or different C$_1$-C$_4$ alkyl groups themselves optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;
- alkoxycarbonyl (R—X$_1$—C(O)—) in which the radical R is a C$_1$-C$_4$ alkoxy radical, X$_1$ is an oxygen atom or an amino group optionally substituted with a C$_1$-C$_4$ alkyl group itself optionally bearing at least one hydroxyl group, said alkyl radical possibly forming with the nitrogen atom to which it is attached a saturated or unsaturated, optionally substituted 5- to 7-membered heterocycle, optionally comprising at least one other nitrogen or non-nitrogen heteroatom;

a cyclic or heterocyclic radical, or a non-aromatic part of an aryl or heteroaryl radical, may also be substituted with one or more oxo groups;

an "aryl" radical generally represents a monocyclic or fused or non-fused polycyclic carbon-based group comprising from 6 to 22 carbon atoms, at least one ring of which is aromatic; preferentially, the aryl radical is a phenyl, biphenyl, naphthyl, indenyl, anthracenyl or tetrahydronaphthyl;

a "cationic heteroaryl radical" is a heteroaryl group as defined previously, which comprises an endocyclic or exocyclic cationic group;

when the charge is endocyclic, it is included in the electron delocalization via the mesomeric effect; for example, it is a pyridinium, imidazolium or indolinium group:

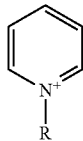  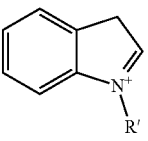

with R and R' being a heteroaryl substituent as defined previously and particularly a (hydroxy)($C_1$-$C_8$)alkyl group, such as methyl;

when the charge is exocyclic, it is not included in the electron delocalization via the mesomeric effect; for example, it is an ammonium or phosphonium substituent $R^+$, such as trimethylammonium, which is outside the heteroaryl, such as pyridyl, indolyl, imidazolyl or naphthalimidyl, in question:

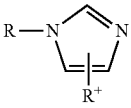 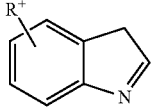

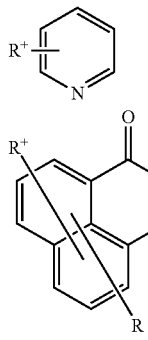

with R being a heteroaryl substituent as defined below and $R^+$ an ammonium $R_aR_bR_cN^+$—, phosphonium $R_aR_bR_cP^+$— or ammonium $R_aR_bR_cN^+$—($C_1$-$C_6$)alkylamino, $R_aR_bR_cN^+$—($C_1$-$C_6$)alkyl or $R_aR_bR_cN^+$—($C_1$-$C_6$)alkoxy group with $R_a$, $R_b$ and $R_c$, which may be identical or different, representing a ($C_1$-$C_8$)alkyl group such as methyl;

a "heteroaryl radical" generally represents a 5- to 22-membered, monocyclic or fused or non-fused polycyclic group, comprising from 1 to 6 heteroatoms chosen from nitrogen, oxygen and sulfur, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl and the ammonium salt thereof;

a "heterocyclic radical" is a 5- to 22-membered, monocyclic or fused or non-fused polycyclic radical that may contain one or two unsaturations but is not aromatic, comprising from 1 to 6 heteroatoms chosen from nitrogen, oxygen and sulfur;

a "heterocycloalkyl radical" is a heterocyclic radical comprising at least one saturated ring;

an "alkyl radical" is a linear or branched $C_1$ to $C_{20}$, preferably $C_1$ to $C_{10}$, more preferentially $C_1$ to $C_8$, better still $C_1$ to $C_6$ and even better still $C_1$ to $C_4$ hydrocarbon-based radical;

the expression "optionally substituted" applied to the alkyl radical implies that said alkyl radical may be substituted with one or more radicals chosen from the following radicals: i) hydroxyl, ii) $C_1$-$C_4$ alkoxy, iii) R—Z—C(X)—Y— with X, Y and Z representing an oxygen or sulfur atom or N(R'), or alternatively X and/or Z represent a bond, R and R', which may be identical or different, represent a hydrogen atom or a ($C_1$-$C_6$)alkyl group, preferably, X represents an oxygen atom, iv) amino optionally substituted with one or two identical or different $C_1$-$C_4$ alkyl radicals, said alkyl radicals possibly forming, with the nitrogen atom that bears them, a 5- to 7-membered heterocycle, optionally comprising another nitrogen or non-nitrogen heteroatom; v) a quaternary ammonium group $N^+R'R''R'''$, $M^-$ for which R', R'' and R''', which may be identical or different, represent a $C_1$-$C_4$ alkyl group, or alternatively —$N^+R'R''R'''$ forms a 5- or 6-membered heteroaryl such as imidazolium optionally substituted with a $C_1$-$C_4$ alkyl group and $M^-$ represents the anionic counterion, vi) carboxyl C(O)OH, vii) carboxylate C(O)O$^-$, $M^+$ with $M^+$ representing a cationic counterion such as alkali metal or alkaline-earth metal, viii) sulfonic —$SO_3H$, ix) sulfonate —$SO_3^-$, $M^+$ with $M^+$ as defined previously, x) cyano and xi) a carbamoyl radical (($R)_2$N—C(O)—) in which R, which may be identical or different, represent a hydrogen atom or a $C_1$ to $C_4$ alkyl radical optionally bearing at least one hydroxyl group;

an "alkoxy radical" is generally an alkyl-oxy radical for which the alkyl radical is a linear or branched $C_1$ to $C_8$ and preferentially $C_1$ to $C_6$ hydrocarbon-based radical;

when the alkoxy group is optionally substituted, this implies that the alkyl group is optionally substituted as defined above;

the term "organic or mineral acid salt" is more particularly intended to mean salts chosen from a salt derived from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)—OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)$—OH; xiv) triflic acid $CF_3SO_3H$; and xv) tetrafluoroboric acid $HBF_4$;

the term "anionic counterion or anion" means an organic or mineral cosmetically acceptable anion or anionic group derived from an organic or mineral acid salt associated with the cationic charge of the dye; more particularly, the anion is chosen from: i) halides such as chloride or bromide; ii) nitrates; iii) sulfonates, including $C_1$-$C_6$ alkylsulfonates: Alk-S(O)$_2$O$^-$ such as methylsulfonate or mesylate and ethylsulfonate; iv) arylsulfonates: Ar—S(O)$_2$O$^-$ such as benzenesulfonate and toluenesulfonate or tosylate; v) carboxylates Alk-C(O)—OH with Alk representing a ($C_1$-$C_6$)alkyl group optionally substituted with one or more hydroxyl or carboxylate groups such as citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$, xiii) phosphates O=P(OH)$_2$—O$^-$, O=P(O$^-$)$_2$—OHO=P(O$^-$)$_3$, HO—[P(O)(O$^-$)]$_w$—P(O)(O$^-$)$_2$ with w being an integer; xiv) acetate; xv) triflate; xvi) borates such as tetrafluoroborate; xvii) sulfate S(O)$_2$O$_2^-$ or SO$_4^{2-}$; xviii) hydrogen sulfate HSO$_4^-$; xix) carbonate; xx) hydrogen carbonate; xxi) perchlorate (ClO$_4^-$) and (xxii) dianionic mineral salts such as a zinc tetrachloride; the anionic counterion, derived from the organic or mineral acid salt, ensures the electrical neutrality of the molecule: thus, it is understood that when the anion comprises several anionic charges, then the same anion may serve for the electrical neutrality of several cationic groups in the same molecule or else may serve for the electrical neutrality of several molecules; for example, a dye which contains two cationic groups may contain either two "singly charged" anionic counterions or a "doubly charged" anionic counterion such as (O=)$_2$S(O$^-$)$_2$ or O=P(O$^-$)$_2$—OH;

in particular, the anionic counterions are chosen from halides such as chloride, bromide, fluoride or iodide; a hydroxide; a sulfate; a hydrogen sulfate; a linear or branched $C_1$-$C_6$ alkyl sulfate, such as the methylsulfate or ethylsulfate ion; carbonates and hydrogen carbonates; carboxylic acid salts such as formate, acetate, citrate, tartrate and oxalate; linear or branched $C_1$-$C_6$ alkylsulfonates, such as the methylsulfonate ion; arylsulfonates for which the aryl part, preferably phenyl, is optionally substituted with one or more $C_1$-$C_4$ alkyl radicals, for instance 4-tolylsulfonate; and alkylsulfonyls such as mesylate;

The term "cationic counterion" is intended to mean alkali metal cations, alkaline-earth metal cations or organic cations such as ammoniums, preferably the anionic counterions of the invention are chosen from alkali metals such as N$^+$ or K$^+$;

The term "chemical oxidizing agent" means any oxidizing agent other than atmospheric oxygen conventionally used in the field. Thus, mention may be made of hydrogen peroxide, urea peroxide, alkali metal bromates, persalts such as perborates and persulfates, and also enzymes, among which mention may be made of peroxidases, 2-electron oxidoreductases such as uricases, and 4-electron oxygenases such as laccases; preferably, the chemical oxidizing agent is hydrogen peroxide;

Moreover, the addition salts that may be used in the context of the invention are especially chosen from addition salts with a cosmetically acceptable base such as alkaline agents as defined below, for instance alkali metal hydroxides, such as sodium hydroxide or potassium hydroxide, aqueous ammonia, amines or alkanolamines;

the expression "at least one" is equivalent to "one or more";

the limits of a range of values are included in that range, in particular in the expressions "between" and "ranging from . . . to . . . "; and the expression "inclusive" for a range of values means that the limits of that range are included in the defined range.

a) The Direct Dyes Different from the Fluorescent Direct Dyes b)

According to one particular embodiment, the direct dye(s) a) different from b), of the invention, is (are) ionic, i.e. is (are) positively or negatively charged or zwitterionic; preferably the direct dye(s) a) of the invention is (are) chosen from cationic or anionic, more preferentially cationic, direct dyes.

According to one particular embodiment, the direct dye(s) a) are yellow, orange, red, green, violet or even blue in colour. More particularly, the dyes a) are yellow, orange or red dyes, preferably yellow or orange dyes. Preferably, the direct dyes a) are not fluorescent.

According to a first preferred embodiment of the invention, the direct dye(s) a) is (are) cationic, i.e. contain(s) at least one quaternized or quaternizable cationic chromophore or at least one chromophore bearing a quaternized or quaternizable cationic group, and not comprising a sulfonate SO$_3^-$ group or carboxylate C(O)O$^-$ group.

According to one particular embodiment of the invention, the cationic direct dye(s) comprise(s) at least one quaternized cationic chromophore.

Mention may be made, as direct dyes according to the invention, of the following dyes: acridines; acridones; anthranthrones; anthrapyrimidines; anthraquinones; azines; (poly)azos, hydrazono or hydrazones, in particular arylhydrazones; azomethines; benzanthrones; benzimidazoles; benzimidazolones; benzindoles; benzoxazoles; benzopyrans; benzothiazoles; benzoquinones; bisazines; bis-isoindolines; carboxanilides; coumarins; cyanines, such as azacarbocyanines, diazacarbocyanines, diazahemicyanines, hemicyanines or tetraazacarbocyanines; diazines; diketopyrrolopyrroles; dioxazines; diphenylamines; diphenylmethanes; dithiazines; flavonoids, such as flavanthrones and flavones; fluorindines; formazans; indamines; indanthrones; indigoids and pseudoindigoids; indophenols; indoanilines; isoindolines; isoindolinones; isoviolanthrones; lactones; (poly)methines, such as dimethines of stilbene or styryl types; naphthalimides; naphthanilides; naphtholactams; naphthoquinones; nitro, in particular nitro(hetero)aromatics; oxadiazoles; oxazines; perilones; perinones; perylenes; phenazines; phenoxazines; phenothiazines; phthalocyanines; polyenes/carotenoids; porphyrins; pyranthrones; pyrazolanthrones; pyrazolones; pyrimidinoanthrones; pyronines; quinacridones; quinolines; quinophthalones; squaranes; tetrazoliums; thiazines; thioindigos; thiopyronines; triarylmethanes or xanthenes; preferably chosen from (poly)azo, hydrazono and triarylmethane dyes.

In particular, the direct dye(s) a) of the invention are chosen from azo cationic dyes. Mention may in particular be made of those resulting from the cationic dyes described in the Kirk-Othmer Encyclopedia of Chemical Technology, "Dyes, Azo", J. Wiley & Sons, updated on 19 Apr. 2010.

Among the azo dyes that may be used according to the invention, mention may be made of the cationic azo dyes described in patent applications WO 95/15144, WO 95/01772 and EP-714954.

According to a preferred embodiment of the invention, the direct dye(s) are chosen from cationic dyes known as "basic dyes".

Mention may be made, among the azo dyes described in the Colour Index International, 3rd edition, in particular of the following compounds:

Basic Red 22
Basic Red 76
Basic Yellow 57
Basic Brown 16
Basic Brown 17

Among the cationic quinone dyes, those mentioned in the abovementioned Colour Index International are suitable and, among these, mention may be made, inter alia, of the following dyes:

Basic Blue 22
Basic Blue 99

Among the azine dyes which are suitable, mention may be made of those listed in the Colour Index International, for example of the following dyes:

Basic Blue 17
Basic Red 2.

Among the cationic triarylmethane dyes which may be used according to the invention, mention may be made, in addition to those listed in the Colour Index, of the following dyes:

Basic Green 1
Basic Violet 3
Basic Violet 14
Basic Blue 7
Basic Blue 26.

Mention may also be made of the cationic dyes described in the documents U.S. Pat. No. 5,888,252, EP 1 133 975, WO 03/029 359, EP 860 636, WO 95/01772, WO 95/15144 and EP 714 954. Mention may also be made of those listed in the encyclopaedia "The Chemistry of Synthetic Dyes" by K. Venkataraman, 1952, Academic Press, vol. 1 to 7, in the "Kirk-Othmer Encyclopedia of Chemical Technology", in the chapter "Dyes and Dye Intermediates", 1993, Wiley and Sons, and in various chapters of "Ullmann's Encyclopedia of Industrial Chemistry", 7th edition, Wiley and Sons.

According to a specific embodiment, the direct dyes are cationic azo dyes, described in EP 850 636, FR 2 788 433, EP 920 856, WO 99/48465, FR 2 757 385, EP 850 637, EP 918 053, WO 97/44004, FR 2 570 946, FR 2 285 851, DE 2 538 363, FR 2 189 006, FR 1 560 664, FR 1 540 423, FR 1 567 219, FR 1 516 943, FR 1 221 122, DE 4 220 388, DE 4 137 005, WO 01/66646, U.S. Pat. No. 5,708,151, WO 95/01772, WO 515 144, GB 1 195 386, U.S. Pat. Nos. 3,524,842, 5,879,413, EP 1 062 940, EP 1 133 976, GB 738 585, DE 2 527 638, FR 2 275 462, GB 1974-27645, Acta Histochem. (1978), 61(1), 48-52; Tsitologiya (1968), 10(3), 403-5; Zh. Obshch. Khim. (1970), 40(1), 195-202; Ann. Chim. (Rome) (1975), 65(5-6), 305-14; Journal of the Chinese Chemical Society (Taipei) (1998), 45(1), 209-211; Rev. Roum. Chim. (1988), 33(4), 377-83; Text. Res. J. (1984), 54(2), 105-7; Chim. Ind. (Milan) (1974), 56(9), 600-3; Khim. Tekhnol. (1979), 22(5), 548-53; Ger. Monatsh. Chem. (1975), 106(3), 643-8; MRL Bull. Res. Dev. (1992), 6(2), 21-7; Lihua Jianyan, Huaxue Fence (1993), 29(4), 233-4; Dyes Pigm. (1992), 19(1), 69-79; Dyes Pigm. (1989), 11(3), 163-72.

According to another preferred embodiment of the invention, the direct dye(s) a) according to the invention are cationic and chosen from hydrazono dyes.

Preferably, the cationic direct dye(s) comprise a quaternary ammonium group; more preferentially, the cationic charge is endocyclic.

These cationic radicals are, for example, a cationic radical:

bearing an exocyclic (di/tri)($C_1$-$C_8$)alkylammonium charge, or bearing an endocyclic charge, such as comprising a cationic heteroaryl group chosen from: acridinium, benzimidazolium, benzobistriazolium, benzopyrazolium, benzopyridazinium, benzoquinolium, benzothiazolium, benzotriazolium, benzoxazolium, bipyridinium, bis-tetrazolium, dihydrothiazolium, imidazopyridinium, imidazolium, indolium, isoquinolium, naphthoimidazolium, naphthoxazolium, naphthopyrazolium, oxadiazolium, oxazolium, oxazolopyridinium, oxonium, phenazinium, phenooxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

Mention may be made of the hydrazono cationic dyes of formulae (II) and (III), the azo dyes of formulae (IV) and (V) below, and also the optical and geometric isomers thereof and tautomers thereof, the organic or mineral acid or base salts thereof, and also the solvates thereof such as hydrates:

(II)

(III)

(IV)

(V)

in which formulae (II) to (V):

Het$^+$ represents a cationic heteroaryl radical, preferentially bearing an endocyclic cationic charge, such as imidazolium, indolium or pyridinium, optionally substituted, preferentially with at least one ($C_1$-$C_8$) alkyl group such as methyl;

Ar$^+$ represents an aryl radical, such as phenyl or naphthyl, having an exocyclic cationic charge, preferentially ammonium, particularly tri($C_1$-$C_8$)alkylammonium, such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar" represents an optionally substituted (hetero)aryl group, such as phenyl or pyrazolyl, which are optionally substituted, preferentially by one or more ($C_1$-$C_8$) alkyl, hydroxyl, (di)($C_1$-$C_8$)(alkyl)amino, ($C_1$-$C_8$) alkoxy or phenyl groups;

$R_a$ and $R_b$, which may be identical or different, represent a hydrogen atom or a ($C_1$-$C_8$)alkyl group, which is optionally substituted, preferentially with a hydroxyl group;

or else the $R_a$ substituent with a substituent of Het$^+$ and/or $R_b$ with a substituent of Ar form, together with the atoms that bear them, a (hetero)cycloalkyl; in particular, $R_a$ and $R_b$ represent a hydrogen atom or a ($C_1$-$C_4$) alkyl group optionally substituted with a hydroxyl group;

Q$^-$ represents an organic or mineral anionic counterion, such as a halide or an alkyl sulfate.

In particular, mention may be made of the azo and hydrazono direct dyes bearing endocyclic cationic charges, of formulae (II) to (V) as defined previously, more particularly cationic direct dyes of formulae (II) to (V) bearing endocyclic cationic charges described in patent applications WO 95/15144, WO 95/01772 and EP-714954.

Preferentially, mention may be made of the following direct dyes:

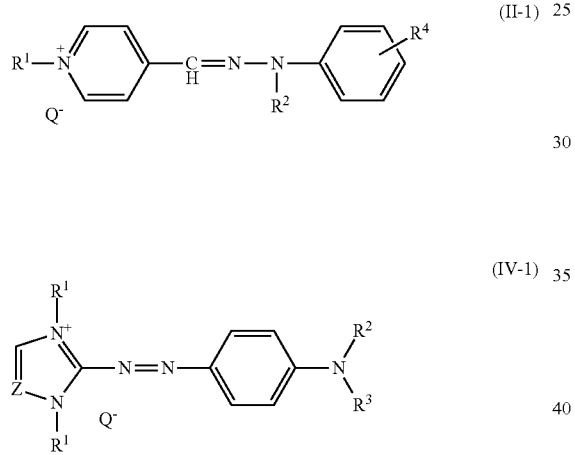

and also the organic or mineral acid or base addition salts thereof, the geometrical isomers, optical isomers and tautomers thereof, and the mesomeric forms thereof, and the solvates such as hydrates;

in which formulae (II-1) and (IV-1):

$R^1$ represents a ($C_1$-$C_4$)alkyl group such as methyl;

$R^2$ and $R^3$, which may be identical or different, represent a hydrogen atom or a ($C_1$-$C_4$)alkyl group, such as methyl; and $R^4$ represents a hydrogen atom or an electron-donating group such as optionally substituted ($C_1$-$C_8$)alkyl, optionally substituted ($C_1$-$C_8$)alkoxy, or (di)($C_1$-$C_8$)(alkyl)amino optionally substituted on the alkyl group(s) with a hydroxyl group; particularly, $R^4$ is a hydrogen atom, Z represents a CH group or a nitrogen atom, preferentially CH, Q$^-$ is an anionic counterion as defined above, in particular a halide, such as chloride, or an alkyl sulfate, such as methyl sulfate or mesityl.

In particular, the dyes of formulae (II-1) and (IV-1) are chosen from Basic Red 51, Basic Yellow 87 and Basic Orange 31 or derivatives thereof:

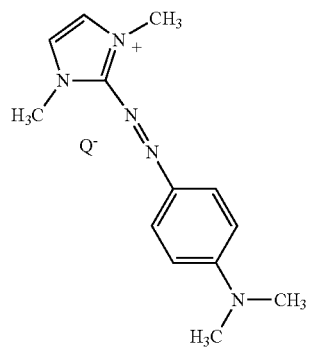

Basic Red 51

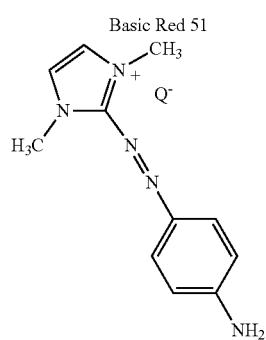

Basic Orange 31

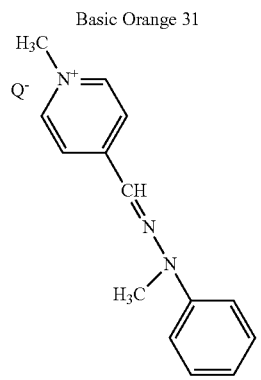

Basic Yellow 87 and also the solvates thereof such as hydrates;

with Q' being an anionic counterion as defined above, in particular a halide, such as chloride, or an alkyl sulfate, such as methyl sulfate or mesityl.

According to one variant of the invention, the cationic dye(s) a) comprise at least one quaternary ammonium radical such as those of formula (VI) below, and also the optical and geometric isomers thereof, the tautomers thereof, the organic or mineral acid or base salts thereof, and also the solvates thereof such as hydrates:

$$W^+\!-\![C(R_c)\!=\!\!C(R_d)]_m Ar; Q^- \qquad (VI)$$

in which formula (VI):

W$^+$ represents a cationic heterocyclic or heteroaryl group, particularly comprising a quaternary ammonium optionally substituted with one or more ($C_1$-$C_8$)alkyl groups, optionally substituted especially by one or more hydroxyl groups;

Ar representing an aryl group such as phenyl or naphthyl, optionally substituted preferentially with i) one or more halogen atoms such as chlorine or fluorine; ii) one or more groups $(C_1-C_8)$alkyl, preferably of $C_1-C_4$ such as methyl; iii) one or more hydroxyl groups; iv) one or more $(C_1-C_8)$alkoxy groups such as methoxy; v) one or more hydroxy$(C_1-C_8)$alkyl groups such as hydroxyethyl, vi) one or more amino groups or (di)$(C_1-C_8)$alkylamino, preferably with the $C_1-C_4$ alkyl part optionally substituted with one or more hydroxyl groups, such as (di)hydroxyethylamino, vii) with one or more acylamino groups; viii) one or more heterocycloalkyl groups such as piperazinyl, piperidyl or 5- or 6-membered heteroaryl such as pyrrolidinyl, pyridyl and imidazolinyl;

m' represents an integer between 1 and 4 inclusive, and in particular m has the value 1 or 2; more preferentially 1;

$R_c$ and $R_d$, which are identical or different, represent a hydrogen atom or an optionally substituted $(C_1-C_8)$ alkyl group, preferentially of $C_1-C_4$, or alternatively $R_c$ contiguous with $W^+$ and/or $R_d$ contiguous with Ar form, with the atoms that carry them, a (hetero)cycloalkyl; particularly, $R_c$ is contiguous with $W^+$ and they form a (hetero)cycloalkyl such as cyclohexyl;

$Q^-$ is an organic or mineral anionic counterion as defined previously.

According to one particular embodiment of the invention, the direct dye(s) a) is (are) chosen from triarylmethanes.

In particular, the triarylmethane dye(s) of the invention may be anionic, cationic or zwitterionic, preferably cationic.

Preferably, the direct dye(s) a) of the invention are chosen from the triarylmethane dyes of formula (I):

and also the organic or mineral acid or base addition salts thereof, the geometrical isomers, optical isomers and tautomers thereof, and the mesomeric forms thereof, and the solvates such as hydrates;

in which formula (I):
  A, B and C are identical or different, and represent a (hetero)aryl group such as phenyl which is optionally substituted,
  ---- represents a single bond or double bond.

The direct dyes of formula (I) can thus be catonic, anionic or zwitterionic.

According to one particularly preferred embodiment of the invention, the triaylmethane dyes are cationic.

Preferably, the triarylmethane direct dye(s) according to the invention are catonic dyes of formulae (IIa) and (II'a) below:

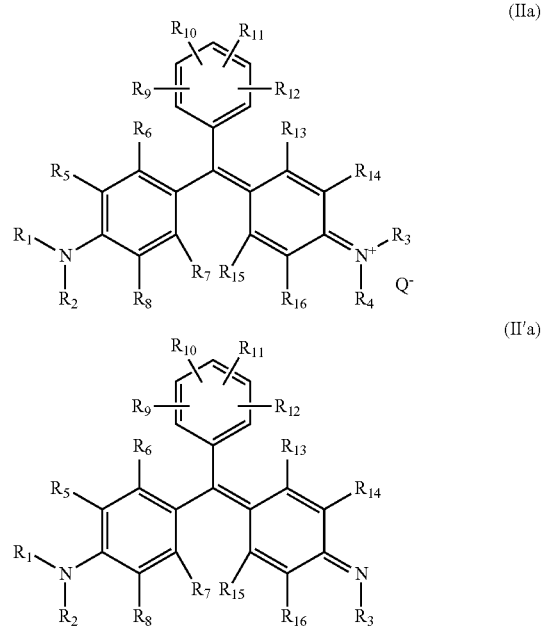

and also the organic or mineral acid or base addition salts thereof, the geometrical isomers, optical isomers and tautomers thereof, and the mesomeric forms thereof, and the solvates thereof such as hydrates:

in which formulae (IIa) and (II'a) below:
  $R_1$, $R_2$, $R_3$ and $R_4$, which may be identical or different, represent a hydrogen atom or one of the following groups: $(C_1-C_6)$alkyl which is optionally substituted, preferably with a hydroxyl group; aryl such as phenyl, aryl$(C_1-C_4)$alkyl such as benzyl, heteroaryl, heteroaryl $(C_1-C_4)$alkyl, or else two groups $R_1$, and $R_2$, and/or $R_3$ and $R_4$, borne by the same nitrogen atom form, together with the nitrogen atom which bears them, an optionally substituted heterocycloalkyl group such as morpholino, piperazino or piperidino, preferably $R_1$, $R_2$, $R_3$ and $R_4$, which may be identical or different, represent a hydrogen atom or a $(C_1-C_4)$alkyl group;
  $R_5$, $R_6$, $R_7$, $R_8$, $R_9$, $R_{10}$, $R_{11}$, $R_{12}$, $R_{13}$, $R_{14}$, $R_{15}$, and $R_{16}$, which may be identical or different, represent a hydrogen or halogen atom, or a group chosen from i) hydroxyl, ii) thiol, iii) amino iv) (di)$(C_1-C_4)$(alkyhamino, v) (di)arylamino such as (di)phenylamino, vi) nitro, vii) acylamino (—NR—C(O)R') in which the R radical is a hydrogen atom, a $C_1-C_4$ alkyl radical optionally bearing at least one hydroxyl group and the R' radical is a $C_1-C_2$ alkyl radical; viii) carbamoyl $((R)_2N-C(O)-)$ in which the R radicals, which may be identical or different, represent a hydrogen atom or a $C_1-C_4$ alkyl radical optionally bearing at least one hydroxyl group; ix) carboxylic acid or ester, (—O—C(O)R') or (—C(O)OR'), in which the R' radical is a hydrogen atom or a $C_1-C_4$ alkyl radical optionally bearing at least one hydroxyl group and the R' radical is a $C_1-C_2$ alkyl radical; x) alkyl which is optionally substituted, in particular with a hydroxyl group; xi) alkylsulfonylamino (R'SO$_2$—NR—) in which the R radical represents a hydrogen atom or a $C_1$-$C_4$ alkyl radical optionally bearing at least one hydroxyl group and the R' radical represents a $C_1$-$C_4$ alkyl radical, a phenyl radical; xii) aminosulfonyl ($(R)_2N$—$SO_2$—) in which the R radicals, which may be identical or different, represent a hydrogen atom or a $C_1$-$C_4$ alkyl radical optionally bearing at least one hydroxyl group; xiii) ($C_1$-$C_4$)alkoxy; and xiv) ($C_1$-$C_4$)alkylthio; or else two radicals borne by two contiguous carbon atoms $R_5$ and $R_6$ and/or $R_7$ and $R_8$ and/or $R_9$ and $R_{10}$ and/or $R_{11}$ and $R_{12}$ and/or $R_{13}$ and $R_{14}$ and/or $R_{15}$ and $R_{16}$ form, together with the carbon atoms which bear them, an aryl or heteroaryl, preferably benzo, 6-membered fused ring, said ring possibly also being optionally substituted, preferably an unsubstituted benzo ring;

$Q^-$ represents an anionic counterion as defined previously, for achieving electron neutrality of the molecule, preferably chosen from halides such as chloride or bromide, and phosphate;

when the cationic dye comprises one or more anionic substituents such as COOR or $SO_3R$ with R denoting a hydrogen or a cation, it is understood that there are then more cationic substituents than anionic substituents, such that the overall resulting charge of the triarylmethane structure is cationic, counterbalanced by $Q^-$.

Even more preferably the direct dye(s) a) of the invention are chosen formulae (IIa) and (II'a) such as from HC Blue 15

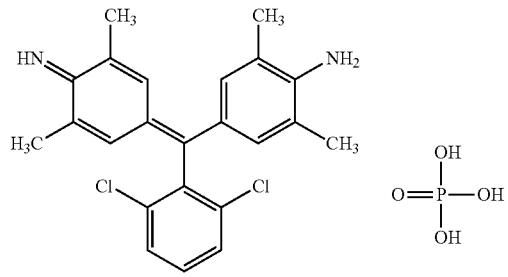 [SMILES: CC1=CC(=C(c2cc(C)c(N)c(C)c2)c2c(Cl)cccc2Cl)C=C(C)C1=N ; O=P(O)(O)O]

According to one preferred embodiment, the direct dye(s) a) is (are) chosen from the triarylmethane dyes of formula (IIa) or (II'a), in which, taken alone or separately, $R_1$, $R_2$, $R_3$ and $R_4$ represent a hydrogen atom or a ($C_1$-$C_4$)alkyl group such as methyl or ethyl;

$R_5$, $R_6$, $R_7$, $R_8$, $R_9$, $R_{10}$, $R_{11}$, $R_{12}$, $R_{13}$, $R_{14}$, $R_{15}$, and $R_{16}$ represent a hydrogen atom, a halogen atom, such as chlorine, or a ($C_1$-$C_4$)alkyl group such as methyl or ethyl, an amino group, a (di)($C_1$-$C_4$)(alkyl)amino group and, preferably, at least one of the $R_9$, $R_{10}$, $R_{11}$ or $R_{12}$ groups represents a hydrogen atom, a halogen atom (Cl), or an amino group, or a ($C_1$-$C_4$)(alkyl)amino or (di)($C_1$-$C_4$)(alkyl)amino group, preferably in the para position with respect to the phenyl group.

Preferably, the direct dye(s) of triaylmethane structure are chosen from Basic Violet 1, Basic Violet 2, Basic Violet 3, Basic Violet 4, Basic Violet 14, Basic Blue 1, Basic Blue 7, Basic Blue 26, Basic green 1, Basic Blue 77 (also called HC Blue 15), and mixtures thereof.

According to another preferred mode of the invention, the direct dye(s) a) are chosen from anionic direct dyes.

The term "anionic direct dyes" is intended to mean any direct dye comprising in its structure at least one sulfonate $SO_3^-$ group and/or at least one carboxylate group $C(O)O^-$ and optionally one or more anionic groups $G^-$ with $G^-$, which may be identical or different, representing an anionic group chosen from alkoxide $O^-$, thiolate $S^-$, carboxylate and thiocarboxylate: $C(Q)Q'^-$ with Q and Q', which may be identical or different, representing an oxygen or sulfur atom; preferably $G^-$ represents a carboxylate, i.e. Q and Q' represent an oxygen atom, and not comprising a quaternized or quaternizable cationic chromophore or a chromophore bearing a quaternized or quaternizable catonic group.

In particular, the term "anionic direct dyes" is commonly intended to mean dyes referred to as "acid" direct dyes owing to their affinity with alkaline substances. The term "anionic direct dyes" means any direct dye comprising in its structure at least one $CO_2R$ or $SO_3R$ substituent with R denoting a hydrogen atom or a cation originating from a metal or an amine, or an ammonium ion.

Preferably, the anionic direct dye(s) is (are) chosen from acidic nitro direct dyes, acidic azo dyes, acidic azine dyes, acidic triarylmethane dyes, acidic indoamine dyes, acidic anthraquinone dyes, acidic indigoids and acidic natural dyes; each of these dyes having at least one sulfonate or carboxylate group bearing a cationic counterion as defined previously; preferentially alkali metal, alkaline-earth metal or ammonium sulfonate or carboxylate.

More particularly, the dye(s) of the invention are chosen from the direct dyes of formula (A):

$$Col^{(-)}{}_m(Q^+)_n \qquad (A)$$

$Col^{(-)}{}_m$ represents the anionic part of the anionic direct dye or "acid" dye comprising in its structure at least one sulfonate group and/or at least one carboxylate group and comprising m anionic charge(s):

m and n, which may be identical or different, represent an integer between 1 and 10 inclusive;

$Q^+$, which may be identical or different, represents an organic or mineral cationic counterion preferably chosen from alkali metal or alkaline-earth metal cations such as $Na^+$ or $K^+$.

In formula (A) of the invention, the radical $Col^{(-)}m$ represents the anionic part of the "acid dyes" or of the anionic direct dyes and preferentially $Col^{(-)}m$ comprises in its structure:

at least one sulfonate group and at least one (hetero)aryl group, it being understood that at least one sulfonate group is directly connected to a (hetero)aryl group, preferentially aryl such as phenyl or benzo; and optionally one or more anionic groups $G^-$ as defined previously.

According to another preferred embodiment of the invention, $Col^{(-)}m$ comprises in its structure:

at least one carboxylate group; and at least one (hetero)aryl group, it being understood that at least one carboxylate group is directly connected to a (hetero)aryl group, preferentially aryl such as phenyl or benzo; and optionally one or more anionic groups $G^-$ as defined previously.

According to yet another preferred embodiment of the invention $Col^{(-)}{}_m$ comprises in its structure:

at least one carboxylate group, at least one sulfonate group and at least one (hetero)aryl group, it being understood that at least one sulfonate or carboxylate group is directly connected to a (hetero)aryl group, preferentially aryl such as phenyl or benzo; and optionally one or more anionic groups $G^-$ as defined previously.

According to a particular embodiment of the invention, the dyes of formula (A) are such that m is equal to n.

An advantageous variant of the invention concerns the dyes of formula (A) for which m and n are equal to 1, 2 or 3.

The preferred anionic dyes of formula (A) of the invention are chosen from acidic nitro direct dyes, acidic azo dyes, acidic azine dyes, acidic triarylmethane dyes, acidic indoamine dyes, acidic anthraquinone dyes, acidic indigoids and acidic natural dyes; each of these dyes having at least one sulfonate or carboxylate group bearing a cationic counterion as defined previously; preferentially alkali metal, alkaline-earth metal or ammonium sulfonate or carboxylate.

As dyes according to the invention, mention may be made of the dyes of formulae (VII), (VII'), (VIII), (VIII'), (IX), (IX'), (X), (X'), (XI), (XII), (XII'), (XIII), and (XIV) below:

c3a) the diaryl anionic azo dyes of formula (VII) or (VII'):

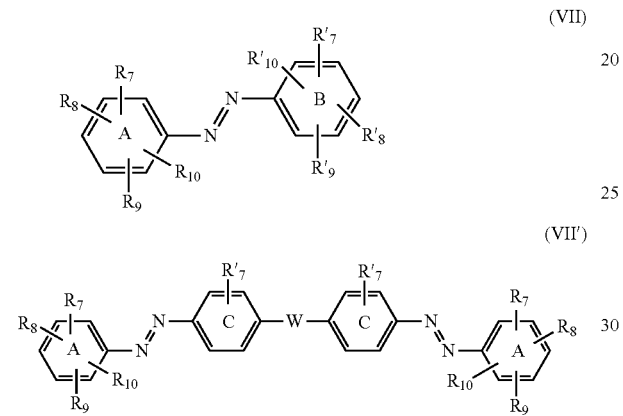

in which formulae (VII) and (VII'):

$R_7$, $R_8$, $R_9$, $R_{10}$, $R'_7$, $R'_8$, $R'_9$, and $R'_{10}$, which may be identical or different, represent a hydrogen atom or a group chosen from: i) alkyl, ii) alkoxy, iii) alkylthio, iv) hydroxyl, v) mercapto, vi) nitro, vii) $R^o$—C(X)—X'—, $R^o$—X'—C(X)—, $R^o$—X'—C(X)—X"— with $R^o$ representing a hydrogen atom or an alkyl or aryl group; X, X' and X", which may be identical or different, representing an oxygen or sulfur atom or NR with R representing a hydrogen atom or an alkyl group; viii) $(O)_2S(O^-)$—, $M^+$ with $M^+$ represents a cationic counterion as defined previously; ix) (O)CO$^-$—, $M^+$ with $M^+$ represents an organic or mineral cationic counterion preferably chosen from alkali metal or alkaline-earth metal cations such as $Na^+$ or $K^+$; x) R"—S(O)$_2$—, with R" representing a hydrogen atom, an alkyl group, an aryl, (di)(alkyl)amino or aryl(alkyl)amino group; preferentially a phenylamino or phenyl group; xi) R'"—S(O)$_2$—X'— with R'" representing an optionally substituted alkyl or aryl group, X' as defined previously; xii) (di)(alkyl)amino; xiii) aryl(alkyl)amino optionally substituted with one or more groups chosen from nitro; nitroso; $(O)_2S(O^-)$—, $M^+$ and alkoxy with $M^+$ as defined previously; xiv) optionally substituted heteroaryl; preferentially a benzo thiazolyl group; xv) cycloalkyl; especially cyclohexyl, xvi) Ar—N=N— with Ar representing an optionally substituted aryl group; preferentially a phenyl optionally substituted with one or more alkyl groups, $(O)_2S(O^-)$—, $M^+$ or phenylamino;

or alternatively two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with one or more groups chosen from i) nitro; ii) nitroso; iii) $(O)_2S(O^-)$—, $M^+$; iv) hydroxyl; v) mercapto; vi) (di)(alkyl)amino; vii) $R^o$—C(X)—X'—; viii) $R^o$—X'—C(X)—; ix) $R^o$—X'—C(X)—X"—; Ar—N=N— and xi) optionally substituted aryl(alkyl)amino; with $M^+$, $R^o$, X, X', X" and Ar as defined previously;

W represents a sigma bond σ, an oxygen or sulfur atom, or a divalent radical i) —N(R)— with R as defined previously, or ii) methylene —C($R_a$)($R_b$)— with $R_a$ and $R_b$, which may be identical or different, representing a hydrogen atom or an aryl group, or alternatively $R_a$ and $R_b$ form, together with the carbon atom that bears them, a spiro cycloalkyl; preferentially, W represents a sulfur atom or $R_a$ and $R_b$ together form a cyclohexyl;

it being understood that formulae (VII) and (VII') comprise at least one sulfonate $(O)_2S(O^-)$—, $Q^+$ or carboxylate (O)C (O$^-$)—, $Q^+$ radical on one of the rings A, A, B, B' or C with $R_1R_2R_3R_4$ as defined previously; $Q^+$ represents an organic or mineral cationic counterion preferably chosen from alkali metal or alkaline-earth metal cations such as $Na^+$ or $K^+$ preferentially alkali metal, alkaline-earth metal or ammonium sulfonate or carboxylate;

As examples of dyes of formula (II), mention may be made of: Acid Red 1, Acid Red 4, Acid Red 13, Acid Red 14, Acid Red 18, Acid Red 27, Acid Red 32, Acid Red 33, Acid Red 35, Acid Red 37, Acid Red 40, Acid Red 41, Acid Red 42, Acid Red 44, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Acid Yellow 9, Acid Yellow 36, Acid Yellow 199, Food Yellow 3; Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2;

and as examples of dyes of formula (VII'), mention may be made of: Acid Red 111, Acid Red 134, Acid yellow 38;

c3b) the pyrazolone anionic azo dyes of formulae (VIII) and

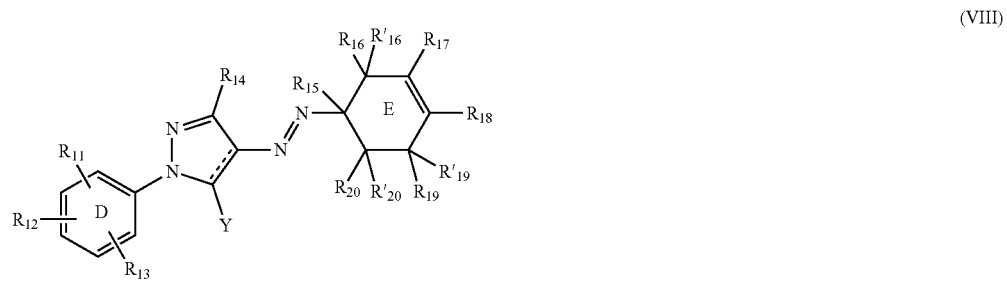

-continued

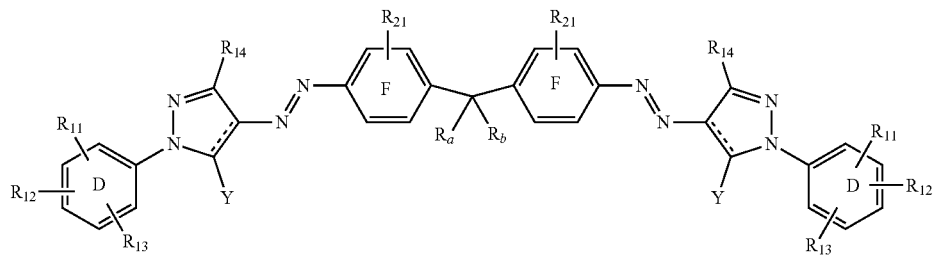
(VIII')

in which formulae (VIII) and (VIII'):
$R_{11}$, $R_{12}$ and $R_{13}$, which may be identical or different, represent a hydrogen or halogen atom, an alkyl group or —(O)$_2$S(O$^-$), M$^+$ with M$^+$ as defined previously;
$R_{14}$ represents a hydrogen atom, an alkyl group or a group —C(O)O—, M$^+$ with M$^+$ as defined previously;
$R_{15}$ represents a hydrogen atom;
$R_{16}$ represents an oxo group, in which case R'$_{16}$ is absent, or alternatively $R_{15}$ with $R_{16}$ together form a double bond;
$R_{17}$ and $R_{18}$, which may be identical or different, represent a hydrogen atom or a group chosen from:
(O)$_2$S(O$^-$)—, M$^+$ with M$^+$ as defined previously;
Ar—O—S(O)$_2^-$ with Ar representing an optionally substituted aryl group, preferentially a phenyl optionally substituted with one or more alkyl groups;
$R_{19}$ and $R_{20}$ together form either a double bond, or a benzo group D', which is optionally substituted;
R'$_{16}$, R'$_{19}$ and R'$_{20}$, which may be identical or different, represent a hydrogen atom or an alkyl or hydroxyl group;
$R_{21}$ represents a hydrogen atom or an alkyl or alkoxy group;
$R_a$ and $R_b$, which may be identical or different, are as defined previously, preferentially $R_a$ represents a hydrogen atom and $R_b$ represents an aryl group;
Y represents either a hydroxyl group or an oxo group;
- - - represents a single bond when Y is an oxo group; and represents a double bond when Y represents a hydroxyl group;
it being understood that formulae (VIII) and (VIII') comprise at least one sulfonate group (O)$_2$S(O$^-$)—, Q$^+$ on one of the rings D or E or formulae (VIII) and (VIII') comprise at least one carbon/late group (O)C(O$^-$)—, Q$^+$ with Q$^+$ as defined previously; preferentially comprise at least one sulfonate group (O)$_2$S(O$^-$)—, Q$^+$ on one of the rings D or E and more particularly sulfonate;
As examples of dyes of formula (VIII), mention may be made of: Acid Red 195, Acid Yellow 23, Acid Yellow 27, Acid Yellow 76, and as examples of dyes of formula (VIII'), mention may be made of Acid Yellow 17;
c3c) the anthraquinone dyes of formulae (IX) and (IX'):

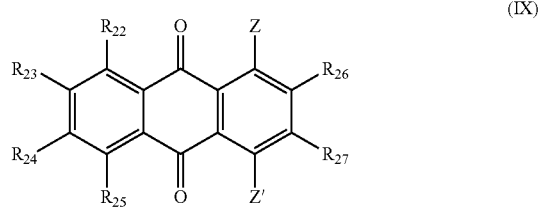
(IX)

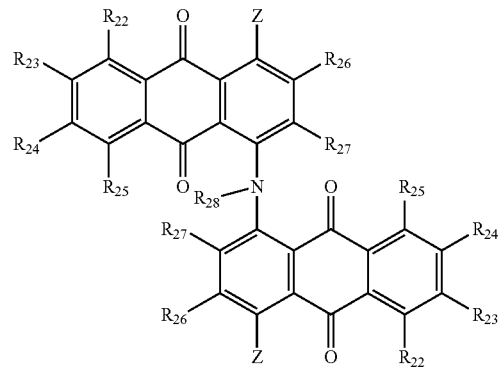
(IX')

in which formulae (IX) and (IX):
$R_{22}$, $R_{23}$, $R_{24}$, $R_{25}$, $R_{26}$ and $R_{27}$, which may be identical or different, represent a hydrogen or halogen atom or a group chosen from i) alkyl, ii) hydroxyl, iii) mercapto, iv) alkoxy, v) alkylthio, vi) aryloxy or arylthio which is optionally substituted, preferentially substituted with one or more groups chosen from alkyl and (O)$_2$S (O$^-$)—, M$^+$ with M$^+$ as defined previously, vii) aryl (alkyl)amino optionally substituted with one or more groups chosen from alkyl and (O)$_2$S(O$^-$)—, M$^+$ with M$^+$ as defined previously, viii) (di)(alkyl)amino, ix) (di)(hydroxyalkyl)amino, x) (O)$_2$S(O$^-$)—, M$^+$ with M$^+$ as defined previously;
Z' represents a hydrogen atom or a group NR$_{28}$R$_{29}$ with $R_{28}$ and $R_{29}$, which may be identical or different, representing a hydrogen atom or a group chosen from i) alkyl, ii) polyhydroxyalkyl such as hydroxyethyl, iii) aryl optionally substituted with one or more groups, particularly alkyl, such as methyl, n-dodecyl, n-butyl; (O)$_2$S(O$^-$)—, M$^+$ with M$^+$ as defined previously; R$^o$—C(X)—X'—, R$^o$—X'—C(X)—, R$^o$—X'—C(X)—X"— with R$^o$, X, X' and X" as defined previously, preferentially R$^o$ represents an alkyl group, iv) cycloakyl; especially cyclohexyl;
Z represents a group chosen from hydroxyl and NR'$_{28}$R'$_{29}$ with R'$_{28}$ and R'$_{29}$, which may be identical or different, representing the same atoms or groups as $R_{28}$ and $R_{29}$ as defined previously;
it being understood that formulae (IX) and (IX') comprise at least one sulfonate group (O)$_2$S(O$^-$)—, Q$^+$;
As examples of dyes of formula (IX), mention may be made of: Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3; and, as examples of dyes of formula (IX'), mention may be made of Acid Black 48;

c3d) the nitro dyes of formulae (X) and (X'):

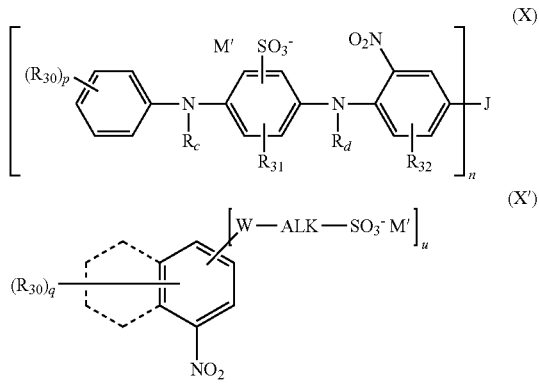

in which formulae (X) and (X'):

$R_{30}$, $R_{31}$ and $R_{32}$, which may be identical or different, represent a hydrogen or halogen atom or a group chosen from i) alkyl, ii) alkoxy optionally substituted with one or more hydroxyl groups, iii) alkylthio optionally substituted with one or more hydroxyl groups, iv) hydroxyl, mercapto, v) nitro, nitroso, vi) (poly)haloalkyl, vii) $R^o$—C(X)—X'—, $R^o$—X'—C(X)—, $R^o$—X'—C(X)—X"— with $R^o$; X, X' and X" as defined previously, viii) $(O)_2S(O^-)$—, $M^+$ with $M^+$ as defined previously, ix) $(O)CO^-$—, $M^+$ with $M^+$ as defined previously, x) (di)(alkyl)amino, xi) (di)(hydroxyalkyl)amino, xii) heterocycloalkyl such as piperidino, piperazino or morpholino; in particular, $R_{30}$, $R_{31}$ and $R_{32}$ represent a hydrogen atom;

$R_c$ and $R_d$, which may be identical or different, represent a hydrogen atom or an alkyl group;

W is as defined previously; W particularly represents a group —NH—;

ALK represents a linear or branched divalent $C_1$-$C_6$ alkylene group; in particular, ALK represents a group —$CH_2$—$CH_2$—;

n is 1 or 2;

p represents an integer between 1 and 5 inclusive;

q represents an integer between 1 and 4 inclusive;

u is 0 or 1;

when n is 1, J represents a nitro or nitroso group; particularly nitro group;

when n is 2, J represents an oxygen or sulfur atom, or a divalent radical —$S(O)_m$— with m representing an integer 1 or 2; preferentially J represents a radical —$SO_2$—;

M' is as defined previously for $M^+$;

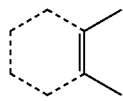

which may be present or absent, represents a benzo group optionally substituted with one or more groups $R_{30}$ as defined previously;

it being understood that formulae (X) and (X') comprise at least one sulfonate group $(O)_2S(O^-)$—, $Q^+$ or carbon/late group $(O)C(O^-)$—, $Q^+$;

As examples of dyes of formula (X), mention may be made of: Acid Brown 13 and Acid Orange 3; as examples of dyes of formula (X'), mention may be made of: Acid Yellow 1, sodium salt of 2,4-dinitro-1-naphthol-7-sulfonic acid, 2-piperidino-5-nitrobenzenesulfonic acid, 2-(4'-N,N(2"-hydroxyethyl)amino-2'-nitro)anilineethanesulfonic acid and 4-β-hydroxyethylamino-3-nitrobenzenesulfonic acid;

c3e) the triarylmethane dyes of formula (XI):

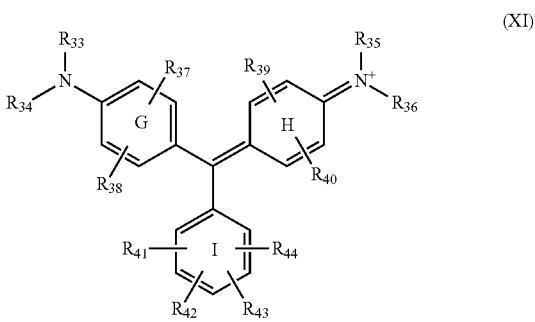

in which formula (XI):

$R_{33}$, $R_{34}$, $R_{35}$ and $R_{36}$, which may be identical or different, represent a hydrogen atom or a group chosen from alkyl, optionally substituted aryl and optionally substituted arylalkyl; particularly an alkyl group and benzyl optionally substituted with a group $(O)_mS(O^-)$—, $M^+$ with $M^+$ and m as defined previously;

$R_{37}$, $R_{38}$, $R_{39}$, $R_{40}$, $R_{41}$, $R_{42}$, $R_{43}$ and $R_{44}$, which may be identical or different, represent a hydrogen atom or a group chosen from: i) alkyl; ii) alkoxy, alkylthio; iii) (di)(alkyl)amino; iv) hydroxyl, mercapto; v) nitro, nitroso; vii) $R^o$—X'—C(X)—, $R^o$—X'—C(X)—X"— with $R^o$ representing a hydrogen atom or an alkyl or aryl group; X, X' and X", which may be identical or different, representing an oxygen or sulfur atom or NR with R representing a hydrogen atom or an alkyl group; viii) (O)2S(O—)—, M+ with M+ representing a hydrogen atom or a cationic counterion; ix) $O)CO^-$—, $M^+$ with $M^+$ as defined previously;

or alternatively two contiguous groups $R_{41}$ with $R_{42}$ or $R_{42}$ with $R_{43}$ or $R_{43}$ with $R_{44}$ together form a fused benzo group: I'; with I' optionally substituted with one or more groups chosen from i) nitro; ii) nitroso; iii) $(O)_2S(O^-)$—, $M^+$; iv) hydroxyl; v) mercapto; vi) (di)(alkyl)amino; vii) $R^o$—C(X)—X'—; viii) $R^o$—X'—C(X)—; and ix) $R^o$—X'—C(X)—X"—; with $M^+$, $R^o$, X, X' and X" as defined previously;

particularly, $R_{37}$ to $R_{40}$ represent a hydrogen atom, and $R_{41}$ to $R_{44}$, which may be identical or different, represent a hydroxyl group or $(O)_2S(O^-)$—, $M^+$; and when $R_{43}$ with $R_{44}$ together form a benzo group, it is preferentially substituted with a group $(O)_2S(O^-)$—; it being understood that at least one of the rings G, H, I or I' comprises at least one sulfonate $(O)_2S(O^-)$—, $Q^+$ or carboxylate $(O)C(O^-)$—, $Q^+$ group;

As examples of dyes of formula (XI), mention may be made of: Acid Blue 1; Acid Blue 3; Acid Blue 7, Acid Blue 9; Acid Violet 49 and Acid Green 50;

c3f) the xanthene-based dyes of formula (XII) or (XII'):

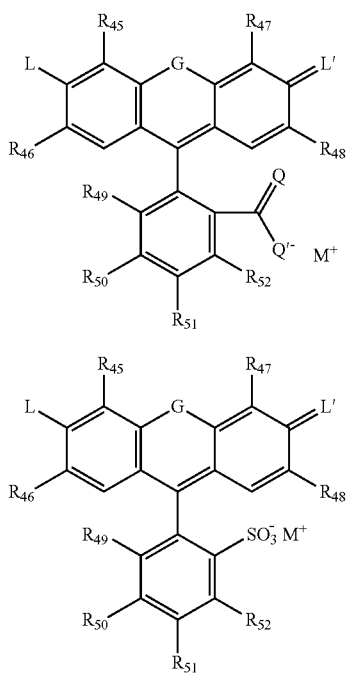

in which formula (XII) or (XII'):
- $R_{45}$, $R_{46}$, $R_{47}$ and $R_{48}$, which may be identical or different, represent a hydrogen or halogen atom;
- $R_{40}$, $R_{50}$, $R_{51}$ and $R_{52}$, which may be identical or different, represent a hydrogen or halogen atom or a group chosen from i) alkyl; ii) alkoxy, alkylthio; iii) hydroxyl, mercapto; iv) nitro, nitroso; v) $(O)_2S(O^-)-$, W with W representing a hydrogen atom or a cationic counterion; vi) $(O)CO^--$, $M^+$ with $M^+$ as defined previously;

particularly, $R_{53}$, $R_{54}$, $R_{55}$ and $R_{48}$ represent a hydrogen or halogen atom;
- G represents an oxygen or sulfur atom or a group $NR_e$ with $R_e$ as defined previously; particularly, G represents an oxygen atom;
- L represents an alkoxide $O^-$, $M^+$; a thioalkoxide $S^-$, $M^+$ or a group $NR_f$, with $R_f$ representing a hydrogen atom or an alkyl group and $M^+$ as defined previously; $M^+$ is particularly $Na^+$ or $K^+$;
- L' represents an oxygen or sulfur atom or an ammonium group: $N^+R_fR_g$, with $R_f$ and $R_g$, which may be identical or different, representing a hydrogen atom, an alkyl group or optionally substituted aryl; L' represents particularly an oxygen atom or a phenylamino group optionally substituted with one or more alkyl or $(O)_mS(O^-)-$, $M^+$ groups with m and $M^+$ as defined previously;
- Q and Q', which may be identical or different, represent an oxygen or sulfur atom; particularly Q and Q' represent an oxygen atom;
- $M^+$ is as defined previously;

it being understood that formula (XII) comprises at least one sulfonate group $(O)_2S(O^-)-$, $Q^+$ or carboxylate group $(O)C(O^-)-$, $Q^+$ with $Q^+$ as defined previously;

As examples of dyes of formula (XII), mention may be made of: Acid Yellow 73; Acid Red 51; Acid Red 87; Acid Red 92; Acid Red 95 and Acid Violet 9;

As examples of formula (XII) mention may be made of Acid Red 52;

c3g) the indigoid dyes of formula (XIII):

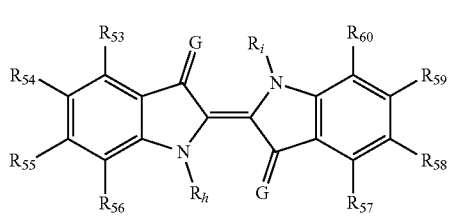

in which formula (XIII):
- $R_{53}$, $R_{54}$, $R_{55}$, $R_{56}$, $R_{57}$, $R_{58}$, $R_{59}$ and $R_{60}$, which may be identical or different, represent a hydrogen atom or a group chosen from: i) alkyl; ii) alkoxy, alkylthio; iii) hydroxyl, mercapto; iv) nitro, nitroso; v) $R^o-C(X)-X'-$, $R^o-X'-C(X)-$, $R^o-X'-C(X)-X''-$ with $R^o$ representing a hydrogen atom or an alkyl or aryl group; X, X' and X", which may be identical or different, representing an oxygen or sulfur atom or NR with R representing a hydrogen atom or an alkyl group; vi) $(O)_2S(O^-)-$, $M^+$ with $M^+$ as defined previously; vii) $(O)CO-$, M+ with M+ as defined previously;
- G represents an oxygen or sulfur atom or a group $NR_e$ with $R_e$ as defined previously; particularly, G represents an oxygen atom;
- $R_i$ and $R_h$, which may be identical or different, represent a hydrogen atom or an alkyl group;

it being understood that formula (XIII) comprises at least one sulfonate group $(O)_2S(O^-)-$, $Q^+$ or carboxylate group $(O)C(O^-)-$, $Q^+$ with $Q^+$ as defined previously;

As examples of dyes of formula (XIII), mention may be made of Acid Blue 74 and indigo carmine (or indigotine I, blue CI No. 1) is a blue dye (number E132) which is a natural extract of the indigo plant.

c3h) the quinoline-based dyes of formula (XIV):

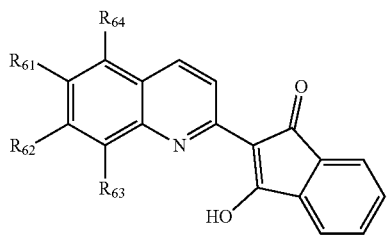

- $R_{61}$ represents a hydrogen or halogen atom or an alkyl group;
- $R_{62}$, $R_{63}$ and $R_{64}$, which may be identical or different, represent a hydrogen atom or a group $(O)_2S(O^-)-$, $M^+$ with $M^+$ as defined previously;
- or alternatively $R_{61}$ with $R_{62}$, or $R_{61}$ with $R_{64}$, together form a benzo group optionally substituted with one or more groups $(O)_2S(O^-)-$, $M^+$ with $M^+$ representing a hydrogen atom or a cationic counterion;

it being understood that formula (IX) comprises at least one sulfonate group $(O)_2S(O^-)-$, $Q^+$ with $Q^+$ as defined previously.

As examples of dyes of formula (IX), mention may be made of the ammonium salts derived from: Acid Yellow 2, Acid Yellow 3 and Acid Yellow 5.

More particularly, the dyes of formulae (VII) to (XIV) that are useful in the invention are chosen from the salts:

| | |
|---|---|
| (C.I. 45380) | Acid Red 87 (XIV) |
| (C.I. 10316) | ammonium salts of 2,4-dinitro-1-naphthol-7-sulfonic acid (X') |
| (C.I. 10383) | Acid Orange 3 (XII) |
| (C.I. 13015) | Acid Yellow 9/Food Yellow 2 (VII) |
| (C.I. 14780) | /Direct Red 45/Food Red 13 (VII) |
| (C.I. 13711) | Acid Black 52 (VII) |
| (C.I. 13065) | Acid Yellow 36 (VII) |
| (C.I. 14700) | ammonium salt of 1-hydroxy-2-(2',4'-xylyl-5-sulfonatoazo)naphthalene-4-sulfonic acid/Food Red 1 (VII) |
| (C.I. 14720) | Acid Red 14/Food Red 3/Mordant Blue 79 (VII) |
| (C.I. 14805) | ammonium salt of 4-hydroxy-3-[(2-methoxy-5-nitrophenyl)diaza]-6-(phenylamino)naphthalene-2-sulfonic acid/Acid Brown 4 (VII) |
| (C.I. 15510) | Acid Orange 7/Pigment Orange 17/Solvent Orange 49 (VII) |
| (C.I. 15985) | Food Yellow 3/Pigment Yellow 104 (VII) |
| (C.I. 16185) | Acid Red 27/Food Red 9 (VII) |
| (C.I. 16230) | Acid Orange 10/Food Orange 4 (VII) |
| (C.I. 16250) | Acid Red 44 (VII) |
| (C.I. 17200) | Acid Red 33/Food Red 12 (VII) |
| (C.I. 15685) | Acid Red 184 (VII) |
| (C.I. 19125) | Acid Violet 3 (VII) |
| (C.I. 18055) | ammonium salt of 1-hydroxy-2-(4'-acetamidophenylazo)-8-acetamidonaphthalene-3,6-disulfonic acid/Acid Violet 7/Food Red 11 (VII) |
| (C.I. 18130) | Acid Red 135 (VII) |
| (C.I. 19130) | Acid Yellow 27(VIII) |
| (C.I. 19140) | Acid Yellow 23/Food Yellow 4 (VIII) |
| (C.I. 20170) | 4'-(sulfonato-2'',4''-dimethyl)bis(2,6-phenylazo)-1,3-dihydroxybenzene/Acid Orange 24 (VII) |
| (C.I. 20470) | ammonium salt of 1-amino-2-(4'-nitrophenylazo)-7-phenylazo-8-hydroxynaphthalene-3,6-disulfonic acid/Acid Black 1 (VII) |
| (C.I. 23266) | (4-((4-methylphenyl)sulfonyloxy)phenylazo)-2,2'-dimethyl-4-((2-hydroxy-5,8-disulfonato)naphthylazo)biphenyl/Acid Red 111 (VII') |
| (C.I. 27755) | Food Black 2 (VII) |
| (C.I. 25440) | 1-(4'-sulfonatophenylazo)-4-((2''-hydroxy-3''-acetylamino-6'',8''-disulfonato)naphthylazo)-6-sulfonatonaphthalene (tetrasodium salt)/Food Black 1 (VII) |
| (C.I. 42090) | Acid Blue 9 (XI) |
| (C.I. 60730) | Acid Violet 43 (IX) |
| (C.I. 61570) | Acid Green 25 (IX) |
| (C.I. 62045) | ammonium salt of 1-amino-4-cyclohexylamino-9,10-anthraquinone-2-sulfonic acid/Acid Blue 62 (IX) |
| (C.I. 62105) | Acid Blue 78 (IX) |
| (C.I. 14710) | ammonium salt of 4-hydroxy-3-((2-methoxyphenyl)azo)-1-naphthalenesulfonic acid/Acid Red 4 (VII) 2-piperidino-5-nitrobenzenesulfonic acid (X') 2-(4'-N,N-(2''-hydroxyethyl)amino-2'-nitro)anilineethanesulfonic acid (X') 4-β-hydroxyethylamino-3-nitrobenzenesulfonic acid (X') |
| (C.I. 42640) | Acid Violet 49 (XII) |
| (C.I. 42080) | Acid Blue 7 (XI) |
| (C.I. 58005) | 1,2-dihydroxy-3-sulfoanthraquinone/Mordant Red 3 (IX) |
| (C.I. 62055) | 1-amino-9,10-dihydro-9,10-dioxo-4-(phenylamino)2-anthracenesulfonic acid/Acid Blue 25 (IX) |
| (C.I. 14710) | 4-hydroxy-3-((2-methoxyphenyl)azo)-1-naphthalenesulfonic acid/Acid Red 4 (VII) |

Most of these dyes are described in particular in the *Colour Index* published by The Society of Dyers and Colourists, P.O. Box 244, Perkin House, 82 Grattan Road, Bradford, Yorkshire, BD12 JBN England. The anionic dyes that are most particularly preferred are the dyes designated in the *Colour Index* under the code C.I. 58005 (monosodium salt of 1,2-dihydroxy-9,10-anthraquinone-3-sulfonic acid), C.I. 60730 (monosodium salt of 2-[(9,10-dihydro-4-hydroxy-9,10-dioxo-1-anthracenyl)amino]-5-methylbenzenesulfonic acid), C.I. 15510 (monosodium salt of 4-[(2-hydroxy-1-naphthalenyl)azo]benzenesulfonic acid), C.I. 15985 (disodium salt of 6-hydroxy-5-[(4-sulfophenyl)azo]-2-naphthalenesulfonic acid), C.I. 17200 (disodium salt of 5-amino-4-hydroxy-3-(phenylazo)-2,7-naphthalenedisulfonic acid), C.I. 20470 (disodium salt of 1-amino-2-(4'-nitrophenylazo)-7-phenylazo-8-hydroxy-3,6-naphthalenedisulfonic acid), C.I. 42090 (disodium salt of N-ethyl-N-[4-[[4-[ethyl(3-sulfophenyl)methyl]amino]phenyl](2-sulfophenyl)methylene]-2,5-cyclohexadien-1-ylidene]-3-sulfobenzenemethanaminium hydroxide, inner salt), C.I. 61570 (disodium salt of 2,2'-[(9,10-dihydro-9,10-dioxo-1,4-anthracenediyl)diimino]bis[5-methyl]benzenesulfonic acid).

The composition used according to the invention may of course comprise a mixture of dyes of formulae (VII), (VII'), (VIII), (VIII'), (IX), (IX'), (X), (X'), (XI), (XII), (XII'), (XIII), and (XIV) more preferably the anionic direct dye(s) according to the invention are chosen from those of formulae (XII') such as Acid Red 51.

It is also possible to use compounds corresponding to the mesomeric or tautomeric forms of structures (VII) to (XIV).

More particularly, the anionic direct dye(s) according to the invention are chosen from those of formulae (VII), (VIII), (IX), and (XIII), and mixtures thereof, According to one preferred mode of the invention, the direct dye(s) a) are azo dyes of formula (IV) or (IV-1) as defined previously.

According to another preferred mode of the invention, the direct dye(s) a) are hydrazono dyes of formula (II) or (II-1) as defined previously.

According to another preferred mode of the invention, the direct dye(s) a) are triarylmethane dyes of formula (IIa) or (II'a) as defined previously, and in particular HC-blue 15.

Very preferably the direct dyes a) of the invention are neither a direct dye bearing at least one disulfide function, nor a direct dye bearing at least one thiol function, nor a direct dye bearing at least one protected-thiol function.

Even more preferably the direct dyes a) of the invention are not fluorescent.

The composition according to the invention contains, in a cosmetic medium, a total amount of direct dye(s) a) as defined previously of preferably between 0.0001% and 30% inclusive, relative to the total weight of the composition which contains it (them).

Preferably, the total amount of direct dye(s) a) as defined previously is between 0.002% and 5% by weight inclusive, relative to the total weight of the composition which contains it (them). By way of example, the direct dye(s) is (are) in an amount of between 0.005% and 2% inclusive, relative to the total weight of the composition comprising it (them).

b) The Disulfide, Thiol or Protected-Thiol Fluorescent Dyes

The process for dyeing keratin fibres and the composition according to the present invention also use, or comprise, (b) one or more disulfide, thiol or protected-thiol fluorescent dye(s).

In particular, the disulfide, thiol or protected-thiol fluorescent dye(s) b) according to the invention is (are) dyes which absorb light in the yellow, orange and red, particularly red, range, preferably in the absorption wavelength $\lambda_{abs}$ between 400 nm and 500 nm inclusive.

Preferably, the disulfide, thiol or protected-thiol fluorescent dye(s) are chosen from those of formula (Ib):
A—$(X)_p C_{sat}$—S—U and also the organic or mineral acid or base salts thereof, the optical and geometric isomers and tautomers thereof and the solvates thereof such as hydrates, in which formula (Ib):

U represents a radical chosen from:
a) —S—$C'_{sat}$—$(X')_{p'}$-A'; and
b) —Y;

A and A' which may be identical or different, represent a radical containing at least one quaternized cationic fluorescent chromophore or at least one fluorescent chromophore bearing a quaternized or quaternizable cationic group;

Y represents i) a hydrogen atom; or ii) a thiol-function-protecting group;

X and X', which may be identical or different, represent a linear or branched, saturated or unsaturated divalent $C_1$-$C_{30}$ hydrocarbon-based chain, optionally interrupted and/or optionally terminated at one or both of its ends with one or more divalent groups or combinations thereof chosen from:

—N(R)—, —N⁺(R)(R)—, —O—, —S—, —C(O)—, —S(O)— and —SO$_2$—, with R, which may be identical or different, chosen from a hydrogen and a $C_1$-$C_4$ alkyl, hydroxyalkyl or aminoalkyl radical;

an aromatic or non-aromatic, saturated or unsaturated, fused or non-fused (hetero)cyclic radical optionally comprising one or more identical or different, optionally substituted heteroatoms;

p and p', which may be identical or different, are equal to 0 or 1;

$C_{sat}$ and $C'_{sat}$, which may be identical or different, represent an optionally substituted linear or branched, or cyclic, $C_1$-$C_{18}$ alkylene chain.

According to one particular mode of the invention, the dyes (Ib) are disufide dyes, i.e. for which U represents the following radical a) —S—$C'_{sat}$—(X')$_p$-A', and more particularly the dyes of formula (Ib) are symmetrical i.e. are such that A=A', $C_{sat}$=$C'_{sat}$, X=X' and p=p'.

According to another particular mode of the invention, the dyes of formula (Ib) bearing a thiol function are as defined previously, i.e. U representing the radical b) Y.

Another particular embodiment of the invention relates to fluorescent dyes bearing a disulfide, thiol or protected-thiol function.

According to a particular embodiment of the invention, the fluorescent dye of formula (Ib) is a thiol dye, i.e. Y represents i) a hydrogen atom.

In accordance with another particular embodiment of the invention, in the abovementioned formula (Ib), Y is a protecting group known to those skilled in the art, for instance those described in the publications "*Protective Groups in Organic Synthesis*", T. W. Greene, published by John Wiley & Sons, N Y, 1981, pages 193-217; "*Protecting Groups*", P. Kocienski, Thieme, 3rd edition, 2005, chapter 5, and Ullmann's Encyclopedia, "*Peptide Synthesis*", pages 4-5, 2005 Wiley-VCH Verlag GmbH & Co. KGaA, Weinheim 10.1002/14356007.a19 157.

In particular, Y represents a thiol-function protecting group chosen from the following radicals:

($C_1$-$C_4$)alkylcarbonyl;
($C_1$-$C_4$)alkylthiocarbonyl;
($C_1$-$C_4$)alkoxycarbonyl;
($C_1$-$C_4$)alkoxythiocarbonyl;
($C_1$-$C_4$)alkylthiothiocarbonyl;
(di)($C_1$-$C_4$)(alkyl)aminocarbonyl;
(di)($C_1$-$C_4$)(alkyl)aminothiocarbonyl;
arylcarbonyl such as phenylcarbonyl;
aryloxycarbonyl;
aryl($C_1$-$C_4$)alkcoxycarbonyl;
(di)($C_1$-$C_4$)(alkyl)aminocarbonyl such as dimethylaminocarbonyl;
($C_1$-$C_4$)(alkyl)arylaminocarbonyl;
carboxyl;

$SO_3$; M⁺ with M⁺ representing an alkali metal such as sodium or potassium, or else a counterion of the cationic chromophore A and M⁺ are absent;

optionally substituted aryl such as phenyl, dibenzosuberyl or 1,3,5-cycloheptatrienyl;

optionally substituted heteroaryl;

optionally cationic, optionally substituted heterocycloalkyl, the heterocycloalkyl group in particular represents a saturated or partially saturated 5-, 6- or 7-membered monocyclic group comprising from 1 to 4 heteroatoms chosen from oxygen, sulfur and nitrogen, such as di/tetrahydrofuranyl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidyl, morpholinyl, di/tetra/hexahydroazepinyl, di/tetrahydropyrimidinyl, these groups being optionally substituted with one or more groups such as ($C_1$-$C_4$) alkyl, oxo or thioxo; or the heterocycle represents the following group:

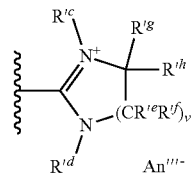

in which $R'^c$, $R'^d$, $R'^e$, $R'^f$, $R'^g$ and $R'^h$, which may be identical or different, represent a hydrogen atom or a ($C_1$-$C_4$)alkyl group, or alternatively two groups $R'^g$ with $R'^h$, and/or $R'^e$ with $R'^f$ form an oxo or thioxo group, or alternatively $R'^g$ with $R'^e$ together form a cycloalkyl; and v represents an integer between 1 and 3 inclusive; preferentially, $R'^c$ to $R'^h$ represent a hydrogen atom; and An'''⁻ represents a counterion;

—C(NR'^cR'^d)=N⁺R'^eR'^f; An'''⁻ with $R'^c$, $R'^d$, $R'^e$ and $R'^f$, which may be identical or different, representing a hydrogen atom or a ($C_1$-$C_4$)alkyl group; preferentially, $R'^c$ to $R'^f$ represent a hydrogen atom; and An'''⁻ represents a counterion;

—C(NR'^cR'^d)=NR'^e; with $R'^c$, $R'^d$ and $R'^e$ as defined previously;

optionally substituted (di)aryl($C_1$-$C_4$)alkyl such as 9-anthracenylmethyl, phenylmethyl or diphenylmethyl optionally substituted with one or more groups in particular chosen from ($C_1$-$C_4$) alkyl, ($C_1$-$C_4$) alkoxy such as methoxy, hydroxyl, alkylcarbonyl or (di)($C_1$-$C_4$)(alkyhamino such as dimethylamino;

optionally substituted (di)heteroaryl($C_1$-$C_4$)alkyl, the heteroaryl group especially being a cationic or non-cationic, 5- or 6-membered monocyclic radical comprising from 1 to 4 heteroatoms chosen from nitrogen, oxygen and sulfur, such as pyrrolyl, furyl, thiophenyl, pyridyl, pyridyl N-oxide such as 4-pyridyl or 2-pyridyl-N-oxide, pyrylium, pyridinium or triazinyl groups, optionally substituted with one or more groups such as alkyl, particularly methyl; advantageously, the (di)heteroaryl($C_1$-$C_4$)alkyl is (di)heteroarylmethyl or (di)heteroarylethyl;

$CR^1R^2R^3$ with $R^1$, $R^2$ and $R^3$, which may be identical or different, representing a halogen atom or a group chosen from:

($C_1$-$C_4$)alkyl;
($C_1$-$C_4$)alkoxy;

optionally substituted aryl such as phenyl optionally substituted with one or more groups, for instance ($C_1$-$C_4$)alkyl, ($C_1$-$C_4$)alkoxy or hydroxyl;

optionally substituted heteroaryl such as thiophenyl, furyl, pyrrolyl, pyranyl or pyridyl, optionally substituted with a ($C_1$-$C_4$)alkyl group;

$P(Z^1)R'^1R'^2R'^3$ with $R'^1$ and $R'^2$, which may be identical or different, representing a hydroxyl, ($C_1$-$C_4$)alkoxy or alkyl group, $R'^3$ representing a hydroxyl or ($C_1$-$C_4$)alkoxy group, and $Z^1$ representing an oxygen or sulfur atom;

a sterically hindered ring; and optionally substituted alkoxyalkyl, such as methoxymethyl (MOM), ethoxyethyl (EOM) and isobutoxymethyl.

In particular, the fluorescent dye(s) of formula (Ib) are such that Y represents a protective group such as:

($C_1$-$C_4$)alkylcarbonyl, for instance methylcarbonyl or ethylcarbonyl;

arylcarbonyl such as phenylcarbonyl;

($C_1$-$C_4$)alkoxycarbonyl;

aryloxycarbonyl;

aryl($C_1$-$C_4$)alkoxycarbonyl;

(di)($C_1$-$C_4$)(alkyl)aminocarbonyl such as dimethylaminocarbonyl;

($C_1$-$C_4$)(alkyl)arylaminocarbonyl;

optionally substituted aryl such as phenyl;

5- or 6-membered monocyclic heteroaryl such as imidazolyl or pyridyl;

cationic 5- or 6-membered monocyclic heteroaryl such as pyrylium, pyridinium, pyrimidinium, pyrazinium, pyridazinium, triazinium, imidazolium; these groups being optionally substituted with one or more identical or different ($C_1$-$C_4$)alkyl groups such as methyl;

cationic 8- to 11-membered bicyclic heteroaryl such as benzimidazolium or benzoxazolium; these groups being optionally substituted with one or more identical or different ($C_1$-$C_4$)alkyl groups such as methyl;

cationic heterocycle having the following formula:

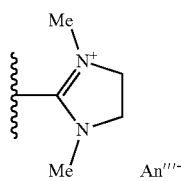 [SMILES: *C1=[N+](C)CCN1C]

—C(NH$_2$)=N$^+$H$_2$; An''''$^-$; with An''''$^-$ being an anionic counterion as defined previously;

—C(NH$_2$)=NH; and

SO$_3^-$, M$^+$ with M$^+$ representing an alkali metal such as sodium or potassium.

As indicated previously, in the fluorescent dye(s) of formula (Ib), $C_{sat}$ and $C'_{sat}$, independently of one another, represent a linear or branched or cyclic, optionally substituted $C_1$-$C_{18}$ alkylene chain.

Substituents of said $C_1$-$C_{18}$ alkylene chain that may be mentioned include the following groups: i) amino, ii) ($C_1$-$C_4$)alkylamino, iii) ($C_1$-$C_4$)dialkylamino, or the group iv) $R^a$—$Z^a$—C($Z^b$)—$Z^c$—, in which $Z^a$, $Z^b$, which may be identical or different, represent an oxygen or sulfur atom, or a group $NR^{a'}$, $Z^c$ represents a bond, an oxygen or sulfur atom or a group $NR^a$, and $R^a$ represents an alkali metal, a hydrogen atom or a $C_1$-$C_4$ alkyl group and $R^{a'}$ represents a hydrogen atom or a $C_1$-$C_4$ alkyl group; more particularly, the groups iv) are chosen from carbon/late C(O)O$^-$ or —C(O)OMetal (Metal=alkali metal), carboxyl —C(O)—OH, guanidino H$_2$H—C(NH$_2$)—NH—, amidino H$_2$H—C(NH$_2$)—, (thio)ureo H$_2$N—C(O)—NH— and H$_2$N—C(S)—NH—, aminocarbonyl-C(O)—NRa'$_2$ or aminothiocarbonyl —C(S)—NRa'$_2$; carbamoyl Ra'C(O)—NRa' or thiocarbamoyl Ra'C(S)—NRa' with Ra', which may be identical or different, representing a hydrogen atom or a ($C_1$-$C_4$) alkyl group; said substituent(s) are preferably present on the carbon in the beta or gamma position relative to the sulfur atoms of the disulfide, thiol or protected-thiol group. Preferably, the fluorescent dye(s) of formulae (Ib) are such that $C_{sat}$ and $C'_{sat}$ represent a —(CH$_2$)$_k$— chain with k being an integer between 1 and 8 inclusive.

In accordance with one particular embodiment of the invention, the fluorescent dye(s) of formulae (Ib) are such that, when p and p' are equal to 1, X and X', which may be identical or different, represent the following sequence: -(T)$_t$-(Z)$_z$-(T')$_{t'}$- said sequence being bonded in formula (Ib) symmetrically as follows: —C$_{sat}$ (or C'$_{sat}$)-(T)$_t$—(Z)$_z$-(A or A'); in which:

T and T', which may be identical or different, represent one or more radicals or combinations thereof chosen from: —O—; —S—; —N(R)—; —N$^+$(R)(R°)—; —S(O)—; —S(O)$_2$—; —C(O)—; with R, R°, which may be identical or different, representing a hydrogen atom, a $C_1$-$C_4$ alkyl radical, $C_1$-$C_4$ hydroxyalkyl radical or an aryl($C_1$-$C_4$)alkyl radical; and a cationic or non-cationic, preferentially monocyclic heterocycloalkyl or heteroaryl radical, preferentially containing two heteroatoms (more preferentially two nitrogen atoms) and preferentially being 5- to 7-membered, more preferentially imidazolium;

the indices t and t', which may be identical or different, are equal to 0 or 1;

Z represents:

—(CH$_2$)$_m$— with m an integer between 1 and 8;

—(CH$_2$CH$_2$O)$_q$— or —(OCH$_2$CH$_2$)$_q$— in which q is an integer between 1 and 5 inclusive;

an aryl, alkylaryl or arylalkyl radical in which the alkyl radical is $C_1$-$C_4$ and the aryl radical is preferably $C_6$, being optionally substituted with at least one group SO$_3$M with M representing a hydrogen atom, an alkali metal or an ammonium group substituted with one or more identical or different, linear or branched $C_1$-$C_{18}$ alkyl radicals optionally bearing at least one hydroxyl;

z is equal to 0 or 1.

Moreover, according to one particular embodiment of the invention, Z represents:

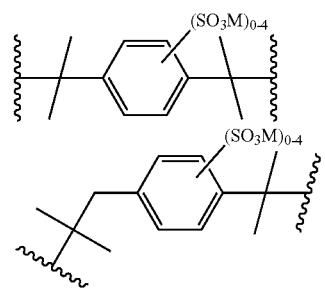

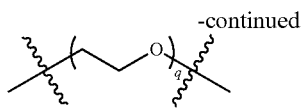

in which M represents a hydrogen atom, an alkali metal or an ammonium group or an ammonium group substituted with one or more identical or different, linear or branched $C_1$-$C_{10}$ alkyl radicals optionally bearing at least one hydroxyl; 0-4 represents an integer between 0 and 4 inclusive, and q represents an integer between 1 and 6 inclusive.

The fluorescent dye(s) of formulae (Ib) are such that A and/or A' represent a quaternized cationic fluorescent chromophore or at least one chromophore bearing a quaternized or quaternizable cationic group. According to one preferred embodiment of the invention, the dyes (Ib) according to the invention are disulfides and comprise identical quaternized cationic chromophores A and N. More particularly, the dyes of formula (Ib) according to the invention are disulfides and symmetrical, i.e. they contain a $C_2$ axis of symmetry, i.e. formula (Ib) is such that:

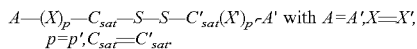

According to one variant, A and/or A' of formulae (Ib) contain at least one cationic radical borne by or included in at least one of the fluorescent chromophores.

Preferably, the cationic radical is a quaternary ammonium; more preferentially, the cationic charge is endocyclic. These cationic radicals are, for example, a cationic radical:
  bearing an exocyclic (di/tri)($C_1$-$C_8$)alkylammonium charge, or
  bearing an endocyclic charge, such as the following cationic heteroaryl groups: acridinium, benzimidazolium, benzobistriazolium, benzopyrazolium, benzopyridazinium, benzoquinolium, benzothiazolium, benzotriazolium, benzoxazolium, bipyridinium, bis-tetrazolium, dihydrothiazolium, imidazopyridinium, imidazolium, indolium, isoquinolium, naphthoimidazolium, naphthoxazolium, naphthopyrazolium, oxadiazolium, oxazolium, oxazolopyridinium, oxonium, phenazinium, phenooxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

According to one embodiment of the invention, the fluorescent dye(s) are of formula (Ib) in which A and/or A' represent(s) a chromophore chosen from those derived from acridine, acridone, benzanthrone, benzimidazole, benzimidazolone, benzindole, benzoxazole, benzopyran, benzothiazole, coumarin, difluoro{2-[(2H-pyrrol-2-ylidene-kN)methyl]-1H-pyrrolato-kN}boron (BODIPY®), diketopyrrolopyrrole, fluorindine, (poly)methine (in particular cyanin and styryl/hemicyanin), naphthalimide, naphthanilide, naphthylamine (such as dansyl), oxadiazole, oxazine, perilones, perinone, perylene, polyene/carotenoid, squarane, stilbene and xanthene fluorescent dyes; preferably, (poly)methines, such as styryl or naphthalimide fluorescent dyes, more particularly of formulae (IIb) and (IIIb) or of formulae (IVb) and (Vb) as defined below.

According to one preferred variant of the invention, the disulfide, thiol or protected-thiol fluorescent dye(s) of formula (Ib) are such that A and/or A' is (are) of formulae (IIb) and (IIIb) below:

with, in formula (IIb) or (IIIb):

$W^+$ representing a cationic heterocyclic or heteroaryl group, particularly comprising a quaternary ammonium optionally substituted with one or more ($C_1$-$C_8$)alkyl groups optionally substituted especially with one or more hydroxyl groups;

$W'^+$ representing a divalent heterocyclic or heteroaryl radical as defined for $W^+$;

Ar representing an aryl group such as phenyl or naphthyl, optionally substituted preferentially with i) one or more halogen atoms such as chlorine or fluorine; ii) one or more groups ($C_1$-$C_8$)alkyl, preferably of $C_1$-$C_4$ such as methyl; iii) one or more hydroxyl groups; iv) one or more ($C_1$-$C_8$)alkoxy groups such as methoxy; v) one or more hydroxy($C_1$-$C_8$)alkyl groups such as hydroxyethyl, vi) one or more amino groups or (di)($C_1$-$C_8$) alkylamino, preferably with the $C_1$-$C_4$ alkyl part optionally substituted with one or more hydroxyl groups, such as (di)hydroxyethylamino, vii) with one or more acylamino groups; viii) one or more heterocycloalkyl groups such as piperazinyl, piperidyl or 5- or 6-membered heteroaryl such as pyrrolidinyl, pyridyl and imidazolinyl;

Ar' is an arylene, i.e. divalent aryl radical, as defined for Ar;

m' represents an integer between 1 and 4 inclusive, and in particular m has the value 1 or 2; more preferentially 1;

$R^c$, $R^d$, which may be identical or different, represent a hydrogen atom or an optionally substituted ($C_1$-$C_8$) alkyl group, preferentially of $C_1$-$C_4$, or alternatively R' contiguous with $W^+$ or $W'^+$ and/or $R^d$ contiguous with Ar or Ar' form, with the atoms that bear them, a (hetero)cycloalkyl, particularly $R^c$ is contiguous with $W^+$ or $W'^+$ and forms a (hetero)cycloalkyl such as cyclohexyl;

$Q^-$ is an organic or mineral anionic counterion as defined previously;

(*) represents the part of the chromophore bonded to the rest of formula (Ib).

According to another variant, the disulfide, thiol or protected-thiol dye(s) of the invention are quaternized or quaternizable fluorescent dyes of formula (Ib) with A and/or A' representing a naphthalimidyl chromophore optionally bearing an exocyclic cationic charge of formula (IVb) or (Vb):

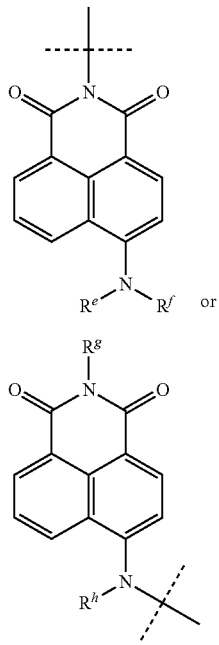

(IVb)

or (Vb)

in which formulae (IVb) and (Vb):
$R^e$, $R^f$, $R^g$, and $R^h$, which may be identical or different, represent a hydrogen atom or a $C_1$-$C_6$ alkyl group which is optionally substituted, preferentially with a di($C_1$-$C_6$)alkylamino or tri($C_1$-$C_6$)alkylammonium group such as trimethylammonium;

representing the bond which bonds the naphthalimidyl radical to the rest of the molecule via X or X', if p=1 or p'=1 or else via $C_{sat}$ or $C_{sat'}$ if p=0 or p'=0.

According to one particular embodiment of the invention, the disulfide, thiol or protected-thiol dye(s) are fluorescent dyes of formula (Ib) of the invention and are such that A and/or A' is (are) of formulae (IIb) and (IIIb) as defined previously, X and X', which may be identical or different, represent the following sequence -(T)$_t$-(Z)$_z$-(T')$_{t'}$- with p=1, z=t'=0, t=1 and T represents —N(R)—, preferably in the para position on Ar relative to the olefin function —C(R$^c$)=C(R$^d$)—. Particularly, in one variant, p=1, z=t'=0, t=1 and T represents —N(R)—, preferably in the para position on Ar relative to the styryl function —C(R$^c$)=C(R$^d$)— and T' represents a group —N(R)— or —N$^+$(R)(R$^o$)— or an imidazolium. Preferably, A and/or A' is (are) of formulae (IIb) and (IIIb) as defined previously with W$^+$ or W'$^+$ representing a group chosen from imidazolium, pyridinium, benzimidazolium, pyrazolium, benzothiazolium and quinolinium, optionally substituted with one or more $C_1$-$C_4$ alkyl radicals, which may be identical or different.

According to one particularly preferred embodiment of the invention, the disulfide, thiol or protected-thiol dye(s) of the invention are quaternized fluorescent dyes of formula (Ib) such that A and/or A' represent the chromophore (IIIb) as defined previously, m'=1, Ar representing a phenyl group substituted in the para position of the styryl group —C(R$^d$)=C(R$^c$)— with a (di)(hydroxy)($C_1$-$C_6$)(alkyhamino group such as dihydroxy($C_1$-$C_4$)alkylamino, and W'$^+$ representing an imidazolium or pyridinium group, preferentially ortho- or para-pyridinium.

According to another preferred embodiment, the disulfide, thiol or protected-thiol dye(s) are fluorescent dyes of formula (Ib) in which A and/or A' represent a styrylpyridinium group of formula below:

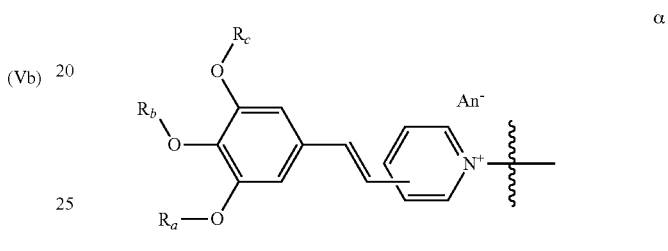

α

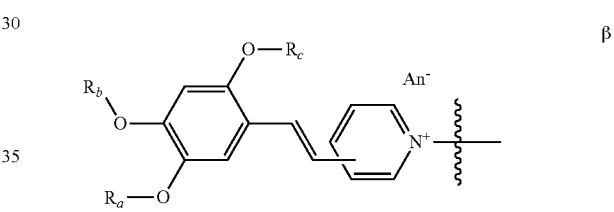

β

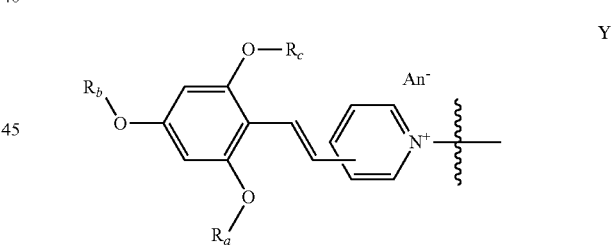

γ with
$R_a$, $R_b$ and $R_c$ representing a hydrogen atom or a ($C_1$-$C_6$) alkyl group, preferably a ($C_1$-$C_6$)alkyl group such as methyl;

representing the bond which bonds the styryl radical to the rest of the molecule and
An$^-$ represents an anionic counterion as defined previously. Preferably, A and A' represent a group β.

According to one particular embodiment of the invention, the disulfide, thiol or protected-thiol fluorescent dye(s) of formula (Ib) are chosen from the dyes of formulae (VIb) to (X'b) below:
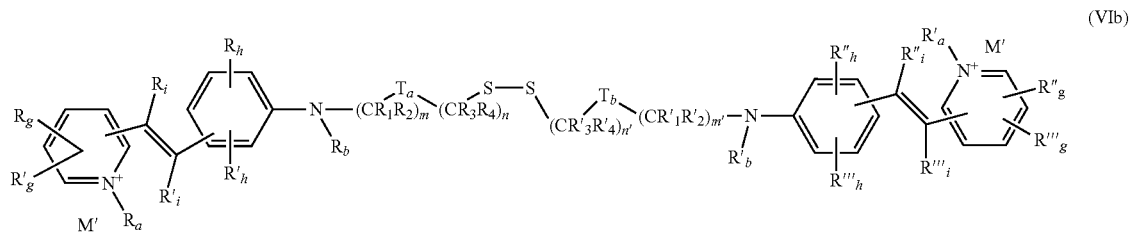
(VIb)
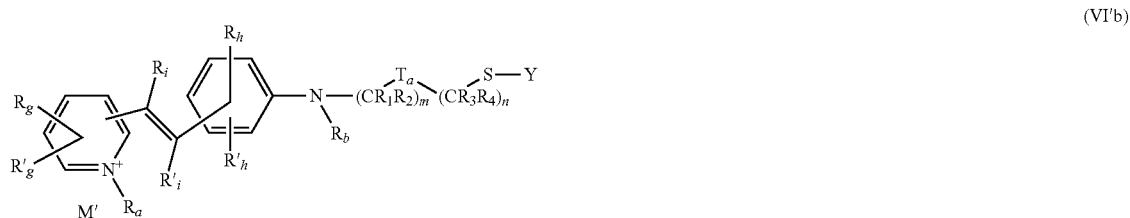
(VI'b)
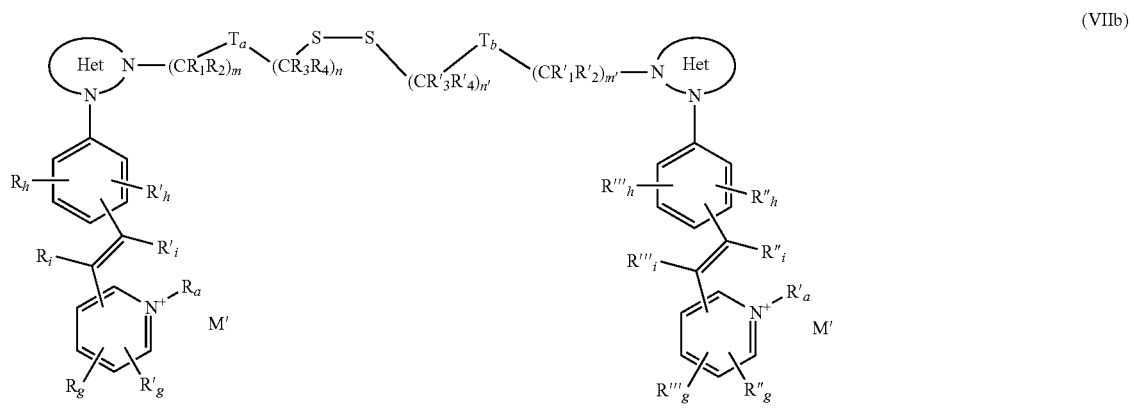
(VIIb)
(VII'b)

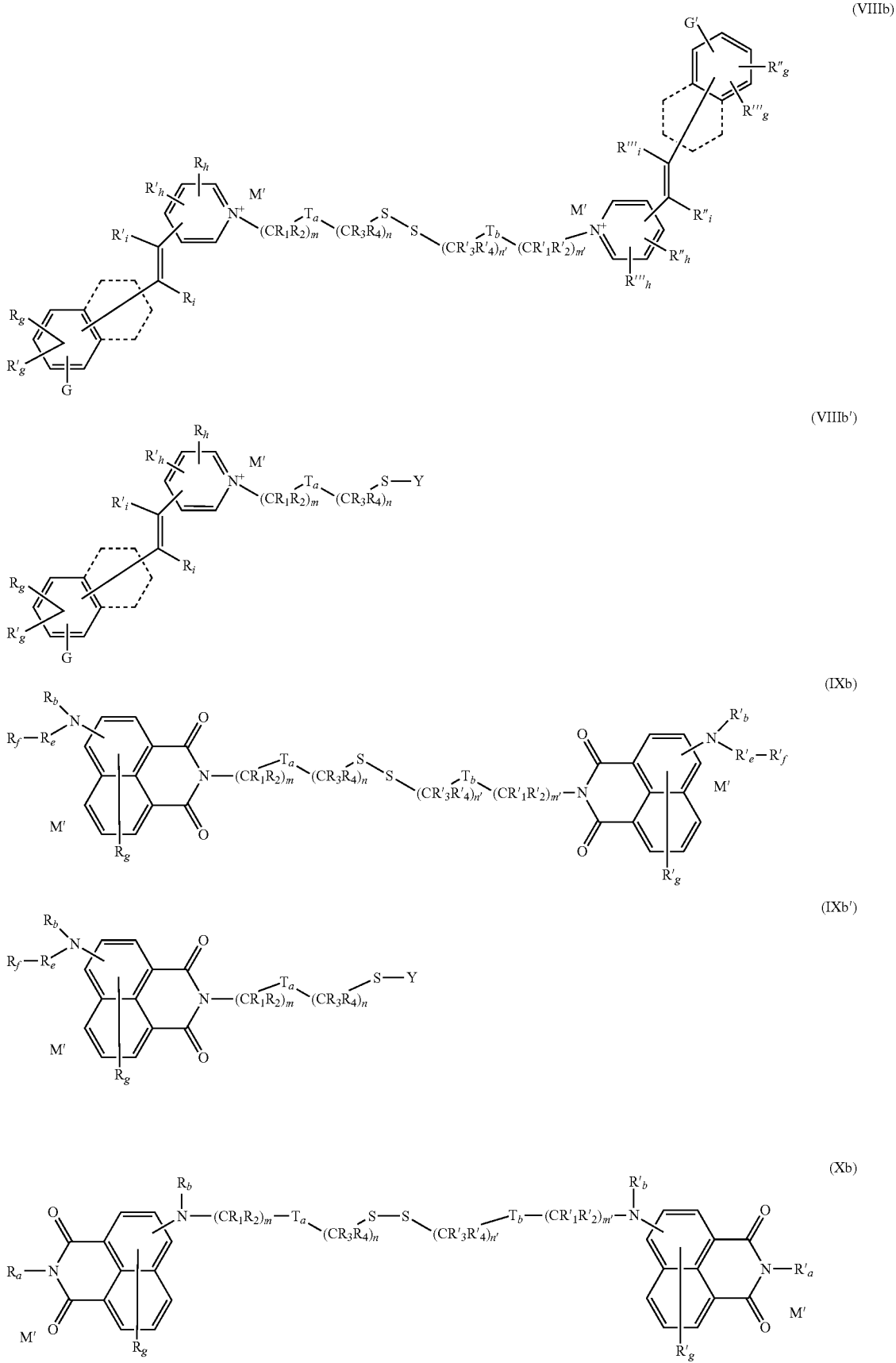

-continued

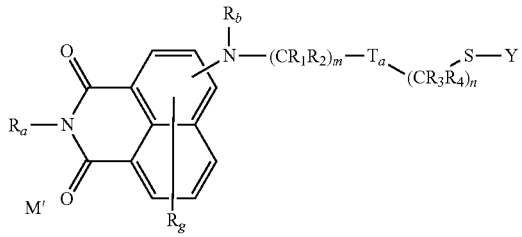

(Xb')

and also the organic or mineral acid or base salts thereof, the optical and geometric isomers and tautomers thereof, and the solvates thereof such as hydrates;
in which formulae (VIb) to (Xb'):

- G and G', which may be identical or different, represent a group $-NR_cR_d$, $-NR'_cR'_d$, or $C_1-C_6$ alkoxy which is optionally substituted, preferentially unsubstituted; preferentially, G and G' represent a group $-NR_cR_d$ and $-NR'_cR'_d$ respectively;
- $R_a$ and $R'_a$, which may be identical or different, represent an aryl($C_1-C_4$)alkyl group or a $C_1-C_6$ alkyl group optionally substituted with a hydroxyl or amino, $C_1-C_4$ alkylamino or $C_1-C_4$ dialkylamino group, said alkyl radicals possibly forming, with the nitrogen atom that bears them, a 5- to 7-membered heterocycle, optionally comprising another nitrogen or non-nitrogen heteroatom; preferentially, $R_a$ and $R'_a$ represent a $C_1-C_3$ alkyl group optionally substituted with a hydroxyl group, or a benzyl group;
- $R_b$ and $R'_b$, which may be identical or different, represent a hydrogen atom, an aryl($C_1-C_4$)alkyl group or a $C_1-C_6$ alkyl group that is optionally substituted; preferentially, $R_b$ and $R'_b$ represent a hydrogen atom or a $C_1-C_3$ alkyl or benzyl group;
- $R_c$, $R'_c$, $R_d$ and $R'_d$, which may be identical or different, represent a hydrogen atom, an aryl($C_1-C_4$)alkyl or $C_1-C_6$ alkoxy group or a $C_1-C_6$ alkyl group that is optionally substituted; $R_c$, $R'_c$, $R_d$ and $R'_d$ preferentially represent a hydrogen atom, a hydroxyl, $C_1-C_3$ alkoxy, amino or $C_1-C_3$ (di)alkylamino group, or a $C_1-C_3$ alkyl group that is optionally substituted with i) a hydroxyl group, ii) amino, iii) $C_1-C_3$ (di)alkylamino, or iv) quaternary ammonium $(R'')(R''')(R'''')N^+$—;
  - or alternatively two adjacent radicals $R_c$ and $R_d$, $R'_c$ and $R'_d$ borne by the same nitrogen atom together form a heterocyclic or heteroaryl group; preferentially, the heterocycle or heteroaryl is monocyclic and 5- to 7-membered; more preferably, the groups are chosen from imidazolyl and pyrrolidinyl;
- $R_e$ and $R'_e$, which may be identical or different, represent a linear or branched $C_1-C_6$ alkylene or $C_2-C_6$ alkenylene hydrocarbon-based chain;
- $R_f$ and $R'_f$, which may be identical or different, represent a group di($C_1-C_4$)alkylamino, $(R'')(R''')N$— or a quaternary ammonium group $(R'')(R''')(R'''')N^+$— in which $R''$, $R'''$ and $R''''$, which may be identical or different, represent a hydrogen atom or a $C_1-C_4$ alkyl group or alternatively $(R'')(R''')(R'''')N^+$— represents an optionally substituted cationic heteroaryl group, preferentially an imidazolinium group optionally substituted with a $C_1-C_3$ alkyl group;
- $R_g$, $R'_g$, $R''_g$, $R'''_g$, $R_h$, $R'_h$, $R''_h$, and $R'''_h$, which may be identical or different, represent a hydrogen atom, a halogen atom, an amino, $C_1-C_4$ alkylamino, $C_1-C_4$ dialkylamino, cyano, carboxyl, hydroxyl or trifluoromethyl group, an acylamino, $C_1-C_4$ alkoxy, (poly)hydroxy($C_2-C_4$)alkoxy, alkylcarbonyloxy, alkoxycarbonyl or alkylcarbonylamino radical, an acylamino, carbamoyl or alkylsulfonylamino radical, an aminosulfonyl radical, or a $C_1-C_{16}$ alkyl radical optionally substituted with a group chosen from $C_1-C_{12}$ alkoxy, hydroxyl, cyano, carboxyl, amino, $C_1-C_4$ alkylamino and $C_1-C_4$ dialkylamino, or alternatively the two alkyl radicals borne by the nitrogen atom of the amino group form a 5- to 7-membered heterocycle optionally comprising another heteroatom identical to or different from that of the nitrogen atom; preferentially, $R_g$, $R'_g$, $R''_g$, $R'''_g$, $R_h$, $R'_h$, $R''_h$, and $R'''_h$ represent a hydrogen or halogen atom or a $C_1-C_3$ alkyl group;
- or alternatively two groups $R_g$ and $R'_g$; $R''_g$ and $R'''_g$; $R_h$ and $R'_h$; $R''_h$ and $R'''_h$ borne by two adjacent carbon atoms together form a benzo or indeno ring, a fused heterocycloalkyl or fused heteroaryl group; the benzo, indeno, heterocycloalkyl or heteroaryl ring being optionally substituted with a halogen atom, an amino, $C_1-C_4$ alkylamino, $C_1-C_4$ dialkylamino, nitro, cyano, carboxyl, hydroxyl or trifluoromethyl group, an acylamino, $C_1-C_4$ alkoxy, (poly)hydroxy($C_2-C_4$)alkoxy, alkylcarbonyloxy, alkoxycarbonyl or alkylcarbonylamino radical, an acylamino, carbamoyl or alkylsulfonylamino radical, an aminosulfonyl radical, or a $C_1-C_{16}$ alkyl radical optionally substituted with: a group chosen from $C_1-C_{12}$ alkoxy, hydroxyl, cyano, carboxyl, amino, $C_1-C_4$ alkylamino, $C_1-C_4$ dialkylamino, or alternatively the two alkyl radicals borne by the nitrogen atom of the amino group form a 5- to 7-membered heterocycle optionally comprising another heteroatom identical to or different from that of the nitrogen atom; preferentially, $R_g$ and $R'_g$; $R''_g$ and $R'''_g$ together form a benzo group;
- or alternatively two groups $R_i$ and $R_g$; $R'''_i$ and $R'''_g$; $R'_i$ and $R'_h$; and/or $R''_i$ and $R''_h$ together form a fused (hetero)cycloalkyl, preferentially cycloalkyl such as cyclohexyl;
- or alternatively when G represents $-NR_cR_d$ and G' represents $-NR'_cR'_d$, two groups $R_c$ and $R'_g$; $R'_c$ and $R''_g$; $R_d$ and $R_g$; $R'_d$ and $R'''_g$ together form a saturated heteroaryl or heterocycle, optionally substituted with one or more $C_1-C_6$ alkyl groups, preferentially a 5- to 7-membered heterocycle containing one or two heteroatoms chosen from nitrogen and oxygen; more preferentially the heterocycle is chosen from morpholinyl, piperazinyl, piperidinyl and pyrrolidinyl groups;
- $R_i$, $R'_i$, $R''_i$, and $R'''_i$, which may be identical or different, represent a hydrogen atom or a $C_1-C_4$ alkyl group;
- $R_1$, $R_2$, $R_3$, $R_4$, $R'_1$, $R'_2$, $R'_3$, and $R'_4$, which may be identical or different, represent a hydrogen atom or a $C_1-C_4$ alkyl, $C_1-C_{12}$ alkoxy, hydroxyl, cyano, carboxy, amino, $C_1$-$C_4$ alkylamino or $C_1$-$C_4$ dialkylamino group, said alkyl radicals possibly forming, with the nitrogen atom which bears them, a 5- to 7-membered heterocycle optionally comprising another nitrogen or non-nitrogen heteroatom; preferentially, $R_1$, $R_2$, $R_3$, $R_4$, $R'_1$, $R'_3$, and $R'_4$ are hydrogen atoms, or a ($C_1$-$C_4$)alkyl or amino group; more preferentially, $R_1$, $R_2$, $R_3$, $R_4$, $R'_1$, $R'_2$, $R'_3$, and $R'_4$ represent a hydrogen atom;

$T_a$, and $T_b$, which may be identical or different, represent i) either a covalent bond s, ii) or one or more radicals or combinations thereof chosen from —$SO_2$—, —O—, —S—, —N(R)—, —$N^+$(R)($R^o$)— and —CO—, with R and $R^o$, which may be identical or different, representing a hydrogen atom, a $C_1$-$C_4$ alkyl or a $C_1$-$C_4$ hydroxyalkyl radical; or an aryl($C_1$-$C_4$)alkyl radical; preferentially, $T_a$ is identical to $T_b$ and they represent a covalent bond s or a group chosen from —N(R)—, —C(O)—N(R)—, —N(R)—C(O)—, —O—C(O)—, —C(O)—O— and —$N^+$(R)($R^o$)—, with R and $R^o$, which may be identical or different, representing a hydrogen atom or a $C_1$-$C_4$ alkyl group; more preferentially, $T_a$ and $T_b$ represent a bond s; iii) or a cationic or non-cationic, preferentially monocyclic heterocycloalkyl or heteroaryl radical, which are preferentially identical, preferentially containing two heteroatoms (more preferentially two nitrogen atoms) and preferentially being 5- to 7-membered, such as imidazolium;

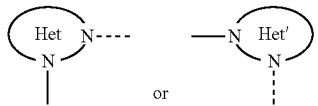

which may be identical or different, represent an optionally substituted group preferentially, the heterocycles are identical, monocyclic and saturated, and comprise in total two nitrogen atoms and from 5 to 8 ring members;

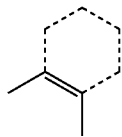

represents an aryl or heteroaryl group fused to the imidazolium or phenyl ring; or alternatively is absent from the imidazolium or phenyl ring; preferentially, when the ring is present, the ring is a benzo;

m, m', n and n', which may be identical or different, represent an integer between 0 and 6 inclusive, with m+n and m'+n', which may be identical or different, represent an integer between 1 and 10 inclusive; preferentially, m+n=m'+n'= an integer between 2 and 4 inclusive; more preferentially, m+n=m'+n'= an integer equal to 2;

Y is as defined above; in particular, Y represents a hydrogen atom or a protective group such as:
($C_1$-$C_4$)alkylcarbonyl, for instance methylcarbonyl or ethylcarbonyl;
arylcarbonyl such as phenylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl such as dimethylaminocarbonyl;
($C_1$-$C_4$)(alkyl)arylaminocarbonyl;
optionally substituted aryl such as phenyl;
5- or 6-membered monocyclic heteroaryl such as imidazolyl or pyridyl;
cationic 5- or 6-membered monocyclic heteroaryl such as pyrylium, pyridinium, pyrimidinium, pyrazinium, pyridazinium, triazinium, imidazolium; these groups being optionally substituted with one or more identical or different ($C_1$-$C_4$)alkyl groups such as methyl;
cationic 8- to 11-membered bicyclic heteroaryl such as benzimidazolium or benzoxazolium; these groups being optionally substituted with one or more identical or different ($C_1$-$C_4$)alkyl groups such as methyl;
cationic heterocycle having the following formula:

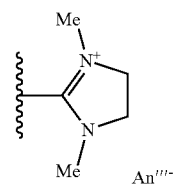 [SMILES: *C1=[N+](C)CCN1C]

—C($NH_2$)=$N^+H_2$; An'''−; with An'''− being an anionic counterion as defined previously;
—C($NH_2$)=NH;
$SO_3^-$, $M^+$ with $M^+$ representing an alkali metal such as sodium or potassium; and M' represents an anionic counterion, derived from a salt of an organic or mineral acid, or from an organic or mineral base that ensures the electrical neutrality of the molecule.

In particular, the dyes of formula (Ib) are chosen from disulfide, thiol or protected-thiol dyes bearing a naphthalidimyl chromophore, chosen from formulae (VIIIb), (VIIIb'), (IXb) and (IX'b) as defined previously.

According to one preferred mode of the invention, the dyes of formula (Ib) are chosen from disulfide, thiol or protected-thiol dyes chosen from formulae (XIb) to (XI'b) below:

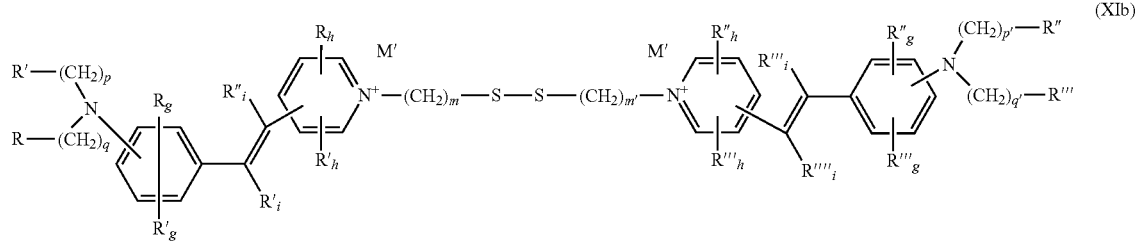

(XIb)

-continued

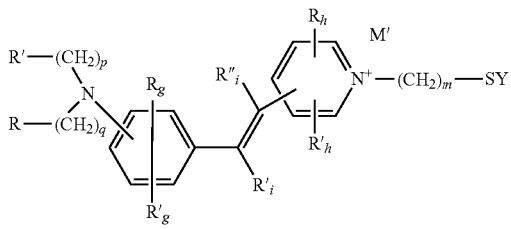

(XIb')

and also the organic or mineral acid or base salts thereof, the optical isomers thereof, the geometric isomers thereof, and the solvates thereof such as hydrates;
in which formulae (XIb) and (XI'b):

- R and R''', which may be identical or different, represent a hydroxyl group, an amino group ($NR_aR_b$) or an ammonium group ($N^+R_aR_bR_c$), $An'^-$; preferentially hydroxyl; with $R_a$, $R_b$ and $R_c$, which may be identical or different, representing a hydrogen atom or a ($C_1$-$C_4$) alkyl group;
- or alternatively two alkyl groups $R_a$ and $R_b$ of the amino or ammonium group form a 5- to 7-membered heterocycle optionally comprising another nitrogen or non-nitrogen heteroatom, such as morpholinyl, piperazinyl, piperidyl, pyrrolyl, morpholinium, piperazinium, piperidinium or pyrrolinium, and $An^-$ representing an anionic counterion;
- R' and R'', which may be identical or different, represent a hydrogen atom or a group as defined for R and R''' respectively;
- $R_g$, $R'_g$, $R''_g$, $R'''_g$, $R_h$, $R'_h$, $R''_h$ and $R'''_h$, which may be identical or different, represent a hydrogen or halogen atom, an amino, (di)($C_1$-$C_4$)alkylamino, cyano, carboxyl, hydroxyl, trifluoromethyl, acylamino, $C_1$-$C_4$ alkoxy, $C_2$-$C_4$ (poly)hydroxyalkoxy, ($C_1$-$C_4$)alkylcarbonyloxy, ($C_1$-$C_4$)alkoxycarbonyl, ($C_1$-$C_4$)alkylcarbonylamino, acylamino, carbamoyl or ($C_1$-$C_4$)alkylsulfonylamino group, an aminosulfonyl radical or a ($C_1$-$C_{16}$)alkyl radical optionally substituted with a group chosen from ($C_1$-$C_{12}$)alkoxy, hydroxyl, cyano, carboxyl, amino and (di)($C_1$-$C_4$)alkylamino, or alternatively the two alkyl radicals borne by the nitrogen atom of the amino group form a 5- to 7-membered heterocycle optionally comprising another nitrogen or non-nitrogen heteroatom; in particular, $R_g$, $R'_g$, $R''_g$, $R'''_g$, $R_h$, $R'_h$, $R''_h$ and $R'''_h$ represent a hydrogen atom or a ($C_1$-$C_4$)alkyl group;
- $R'_i$, $R''_i$, and $R'''_i$, which may be identical or different, represent a hydrogen atom or a ($C_1$-$C_4$)alkyl group; in particular $R'_i$, $R''_i$, $R'''_i$, and $R''''_i$ represent a hydrogen atom;
- m, and m', which may be identical or different, represent an integer between 1 and 10 inclusive; in particular, an integer between 2 and 4 inclusive; preferentially m and m' are equal to 2;
- p, p', q and q', which may be identical or different, represent an integer between 1 and 6 inclusive;
- M' representing an anionic counterion; and
- Y is as defined previously;

it being understood that, when the compound of formula (XIb) or (XIb') contains other cationic parts, it is associated with one or more anionic counterions making it possible to achieve electron neutrality of formula (XI) or (XIb').

According to one particular mode of the invention, the the disulfide, thiol or protected-thiol fluorescent dyes b) belong to formula (XIIb) or (XIIb') which bear an ethylene group connecting the pyridinium part to the phenyl ortho or para to the pyridinium, i.e. 2-4', 4-2', 4-4':

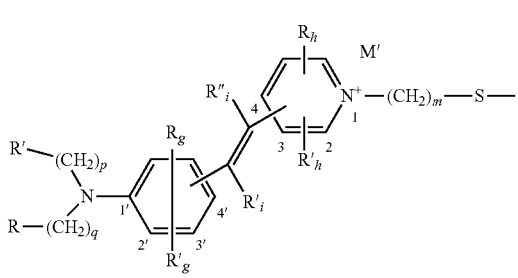

(XIIb)

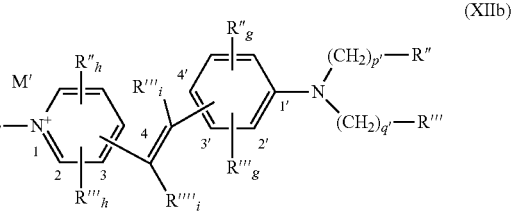

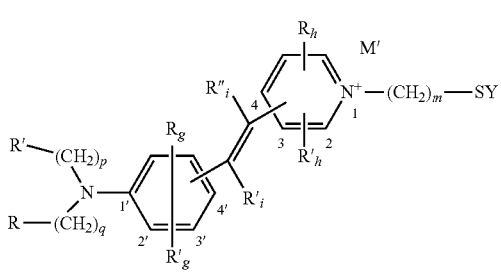

(XIIb')

and also the organic or mineral acid or base salts thereof, the optical and geometric isomers and tautomers thereof, and the solvates thereof such as hydrates;
in which formulae (XIIb) and (XIIb'), R, R', R", R''', $R_g$, $R'_g$, $R''_g$, $R'''_g$, $R_h$, $R'_h$, $R''_h$, $R'''_h$, $R'_i$, $R''_i$, $R'''_i$, $R''''_i$, m, m', p, p', q, q', Y and M' are as defined previously in formulae (XIb) and (XIb'). In particular, $R_h$ and $R''_h$ are ortho to the pyridinium group and $R'_h$ and $R'''_h$ represent a hydrogen atom. Another aspect of the invention concerns the dyes of formula (XIIb) or (XIIb') bearing groups $R_g$, $R''_g$ in position 3' and $R'_g/R'''_g$ which represent a hydrogen atom. advantageously, the dyes of formulae (XIIb) and (XIIb') possess their ethylene group in the para position with respect to the phenyl bearing the amino group: $R'(CH_2)_p$—N—$(CH_2)_q$—R and/or $R''(CH_2)_p$—N—$(CH_2)_{q'}$—R''', i.e. in position 4', preferentially bear an ethylene or styryl group linking the pyridinium part to the phenyl ortho to the pyridinium, i.e. 2-4'.
According to another particular mode of the invention, the disulfide, thiol or protected-thiol fluorescent dyes b) belong to formula (XIIIb) or (XIII'b) below:

or alternatively the groups $R_1$ and $R_2$ form, together with the nitrogen atom that bears them, a saturated heterocyclic radical substituted with at least one hydroxyl, (poly)hydroxy($C_1$-$C_4$)alkyl and/or —C(O)OR' group with R' representing a hydrogen atom, a $C_1$-$C_4$ alkyl group or a group —C(O)—O$^-$ and, in the latter case, an anionic counterion An$^-$ is absent; such as pyrrolidinyl and piperidyl;

$R_3$ represents a hydrogen atom or a group —C(O)OR" with R" representing a hydrogen atom, an alkali metal or a $C_1$-$C_6$ alkyl group or alternatively $R_3$ represents a group —C(O)—O$^-$ and, in the latter case, an anionic counterion An$^-$ is absent;

Z represents a divalent amido group —C(O)—N(R)—, —N(R)—C(O)—, or a divalent $C_1$-$C_{10}$ alkylene group interrupted with an amido group —C(O)—N(R)—, —N(R)—C(O)— such as —$(CH_2)_{n'}$—C(O)—N(R)—$(CH_2)_p$—, —$(CH_2)_{n''}$—N(R)—C(O)—$(CH_2)_p$—, with n' representing an integer between 0 and 3 inclusive; preferentially, n' is equal to 0, 2, 3; p representing an integer between 0 and 4 inclusive, n" representing an

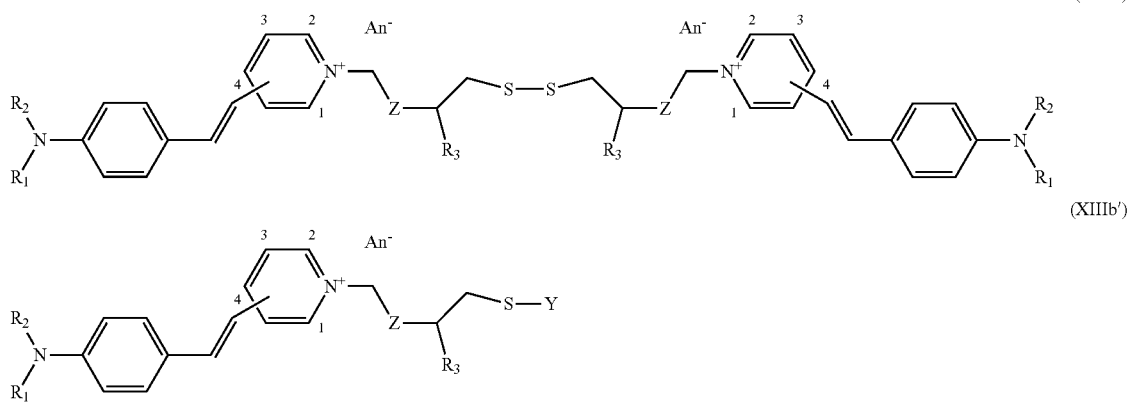

and also the organic or mineral acid or base salts thereof, the optical and geometric isomers and tautomers thereof, and the solvates thereof such as hydrates;
in which formulae (XIIIb) and/or (XIIIb'):
- $R_1$ represents a $C_1$-$C_6$ alkyl group substituted with one or more hydroxyl groups or —C(O)OR' with R' representing a hydrogen atom, a $C_1$-$C_4$ alkyl group or a group —C(O)—O$^-$ and, in the latter case, an anionic counterion An$^-$ is absent; in particular $R_1$ represents a $C_1$-$C_6$ alkyl group substituted with one or more hydroxyl groups and more specifically with only one hydroxyl group;
- $R_2$ represents a $C_1$-$C_6$ alkyl group optionally substituted with one or more hydroxyl groups;

integer between 0 and 3 inclusive and especially n'=n"=p=0 and R representing a hydrogen atom or a $C_1$-$C_6$ alkyl group;

An$^-$ represents an anionic counterion;

Y is as defined previously;

it being understood that when the compound of formula (XIIIb) or (XIIIb') contains other cationic parts, it is combined with one or more anionic counterions that afford formula (XIIIb) or (XIIIb') electrical neutrality.

According to one particular mode of the invention, the dyes of the invention belong to formula (XVIb) or (XVI''''b) below:

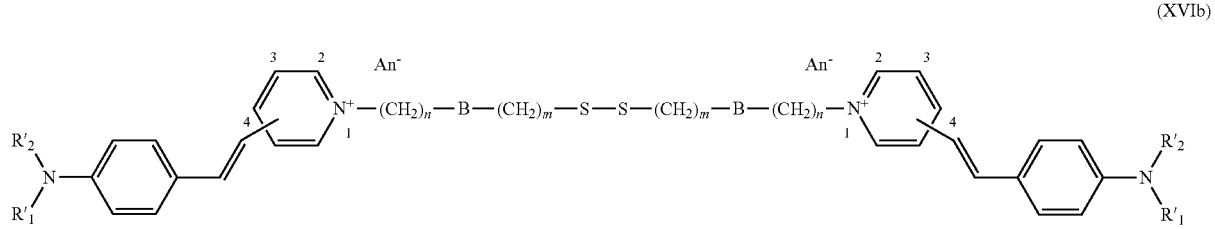

(XVI'b)

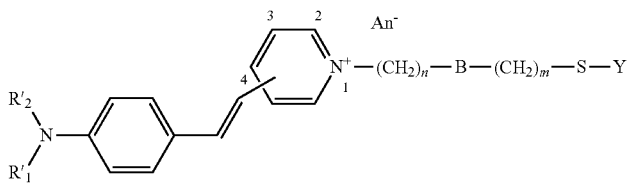

(XVI''b)

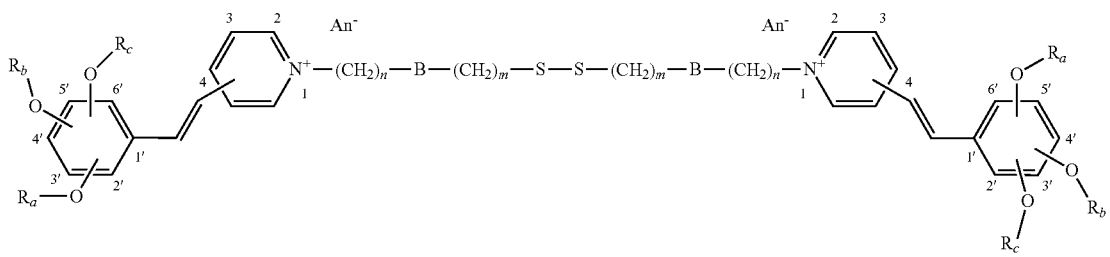

(XVI'''b)

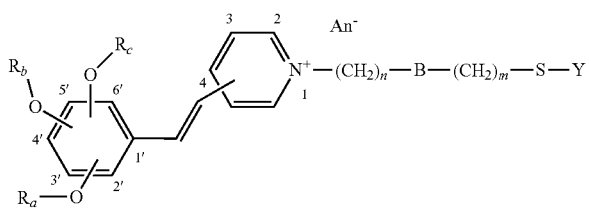

and also the organic or mineral acid or base salts thereof, the optical and geometric isomers and tautomers thereof, and the solvates thereof such as hydrates;

in which formula (XVIb) or (XVI''''b):
represents a $C_1$-$C_4$ alkyl group substituted with one or more hydroxyl groups, particularly with only one hydroxyl group, or —C(O)OR' with R' representing a hydrogen atom, a $C_1$-$C_4$ alkyl group or a group —C(O)—O⁻ and, in the latter case, an anionic counterion An⁻ is absent; preferentially, R'$_1$ represents a $C_1$-$C_4$ alkyl group substituted with a hydroxyl group;

R$_2$ represents a $C_1$-$C_4$ alkyl group optionally substituted with one or more hydroxyl groups, particularly with only one hydroxyl group;

more particularly, R'$_1$ and R'$_2$ are identical;

R$_a$, R$_b$ and R$_c$ represent a ($C_1$-$C_6$)alkyl group such as methyl, they are in particular in positions 3', 4' and 5', or 2', 4' and 5' or 2', 4' and 6', they are preferably in positions 2', 4' and 5', An⁻ represents an anionic counterion as defined previously;

B, represents a bond or a divalent amido group —C(O)—N(R)— or —N(R)—C(O)—, R represents a hydrogen atom or a ($C_1$-$C_6$)alkyl group; preferentially, represents a hydrogen atom;

n and m, which may be identical or different, represent an integer between 1 and 4 inclusive, preferentially n is equal to 3 and m is equal to 2;

Y is as defined previously;

it being understood that the bond between the pyridinium ring and the double bond of the ethylene or styryl group is located in position 2 or 4 of the pyridinium, preferentially at 4.

According to one embodiment, B represents an amido group —C(O)—N(R)— or —N(R)—C(O)—. According to another particular embodiment, B represents a bond.

According to another preferred mode of the invention, the dyes of the invention belong to formula (XIIb) or (XIIb') below:

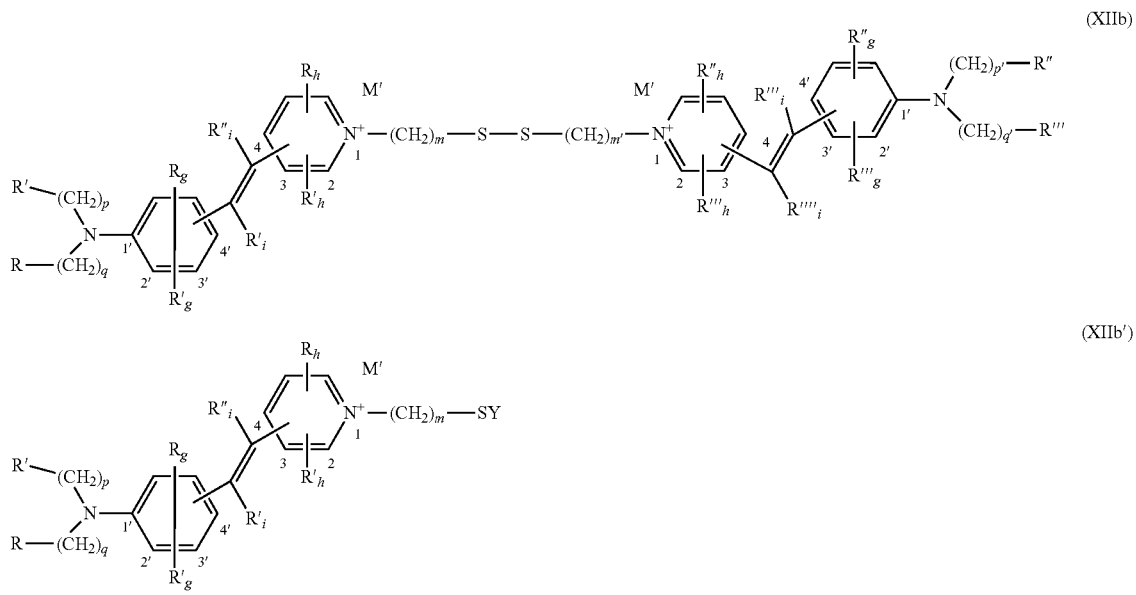

and also the organic or mineral acid or base salts thereof, the optical and geometric isomers and tautomers thereof, and the solvates thereof such as hydrates,
in which formulae (XIIb) and (XIIb'), R, R', R", R"', $R_g$, $R'_g$, $R''_g$, $R'''_g$, $R_h$, $R'_h$, $R''_h$, $R'''_h$, $R'_i$, $R''_i$, $R'''_i$, $R''''_i$, m, m', p, p', q, q', Y and M' are as defined previously in formulae (XIb) and (XIb'). In particular, $R_h$ and $R''_h$ are ortho to the pyridinium group and $R'_h$ and $R''_h$ represent a hydrogen atom. Another aspect of the invention relates to the dyes of formula (XIIb) or (XIIb') possessing groups $R_g$, $R''_g$ in the 3' position and $R'_g/R''_g$ which represent a hydrogen atom.

Advantageously, the dyes of formulae (XIIb) and (XIIb') possess their ethylene group in the para position with respect to the phenyl bearing the amino group: $R'(CH_2)_p$—N—$(CH_2)_q$—R and/or $R''(CH_2)_{p'}$—N—$(CH_2)_{q'}$—R''', i.e. in position 4', preferentially bear an ethylene or styryl group linking the pyridinium part to the phenyl ortho to the pyridinium, i.e. 2-4'.

By way of example, the disulfide, thiol and protected-thiol direct dyes of the invention b) have the following chemical structures:

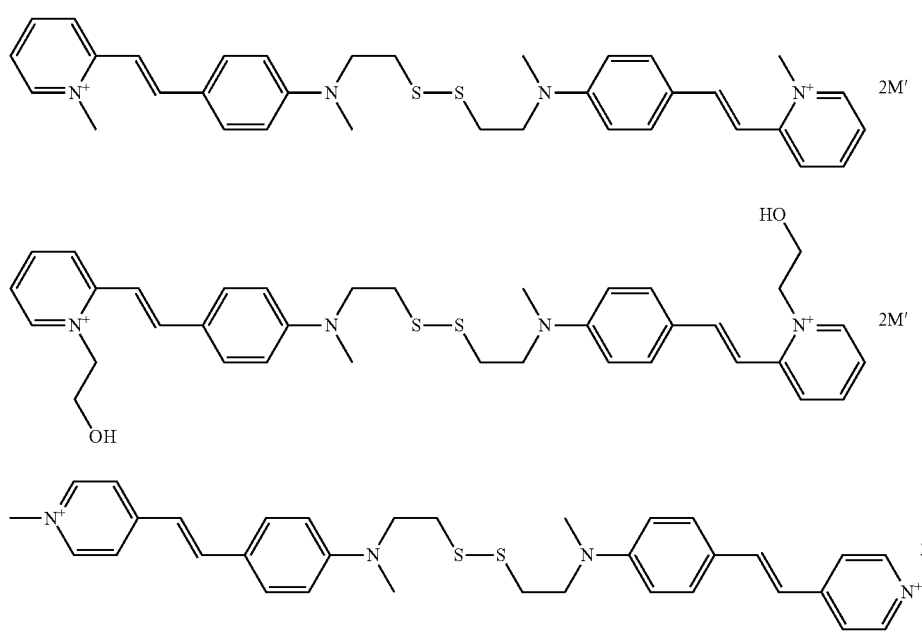

-continued
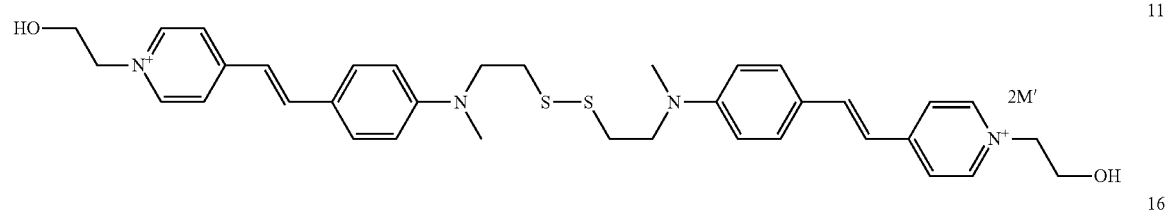
11
2M'
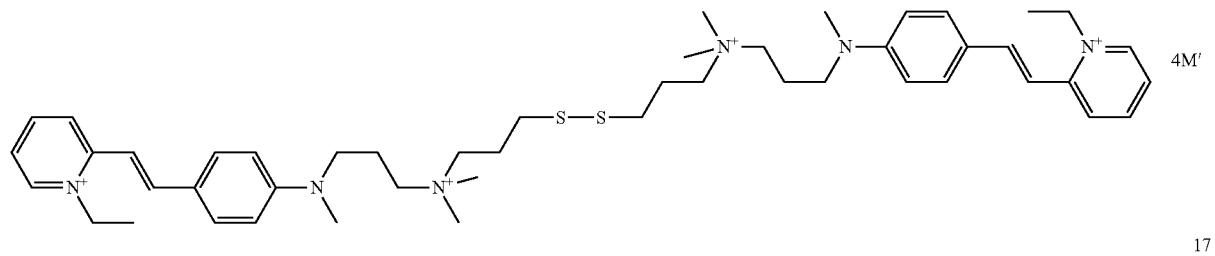
16
4M'
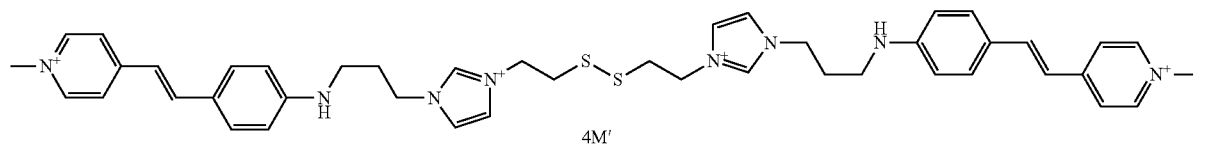
17
4M'
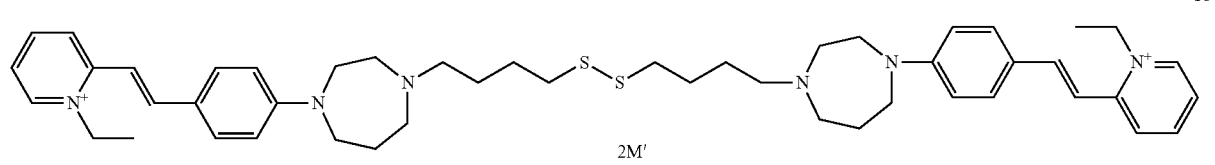
18
2M'
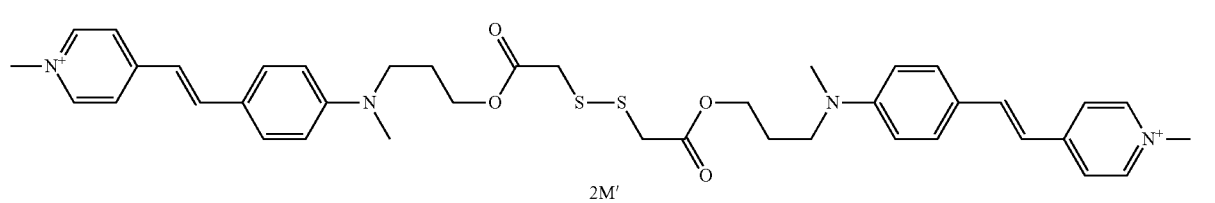
20
2M'
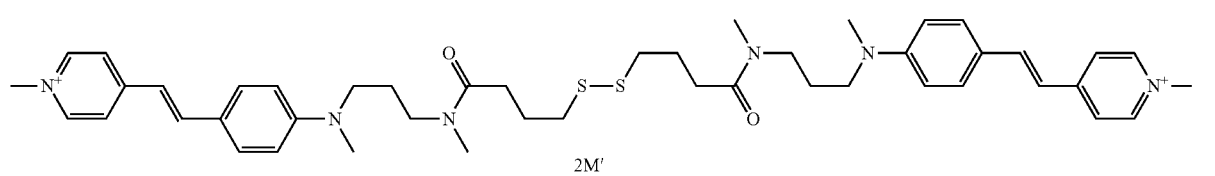
21
2M'
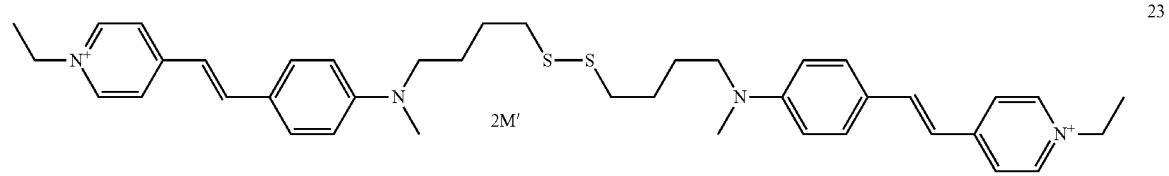
22
2M'
23

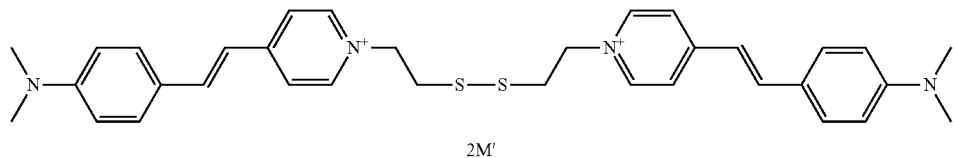
24
2M'
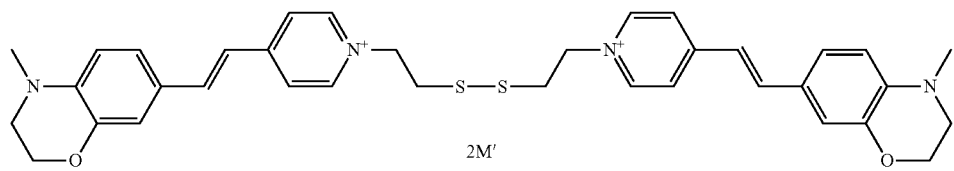
25
2M'
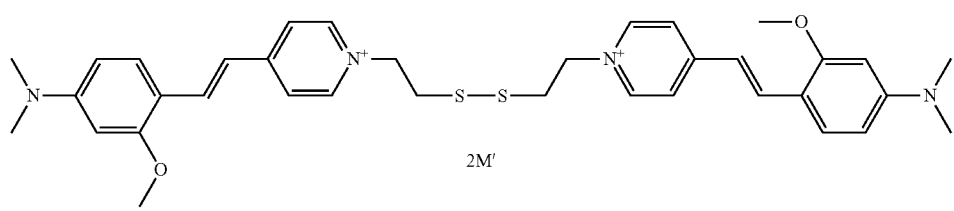
26
2M'
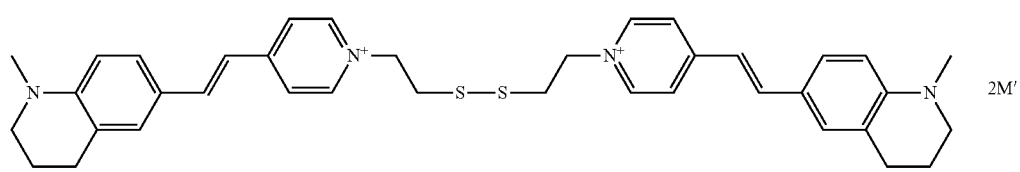
27
2M'
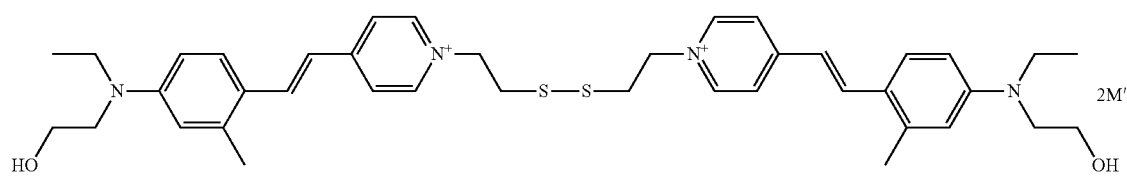
28
2M'
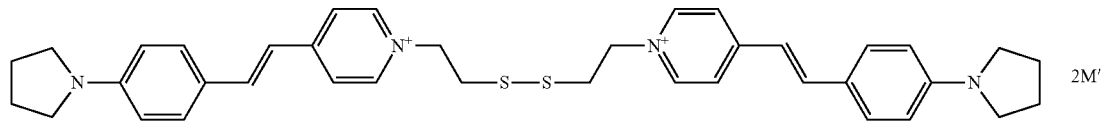
29
2M'
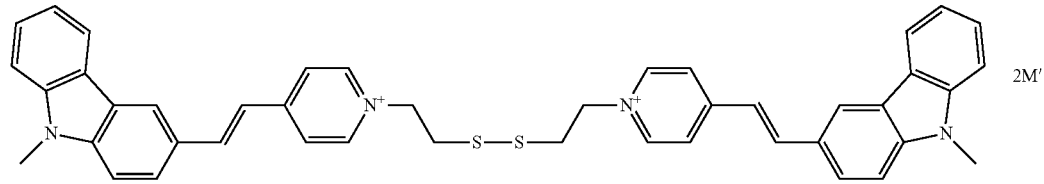
30
2M'
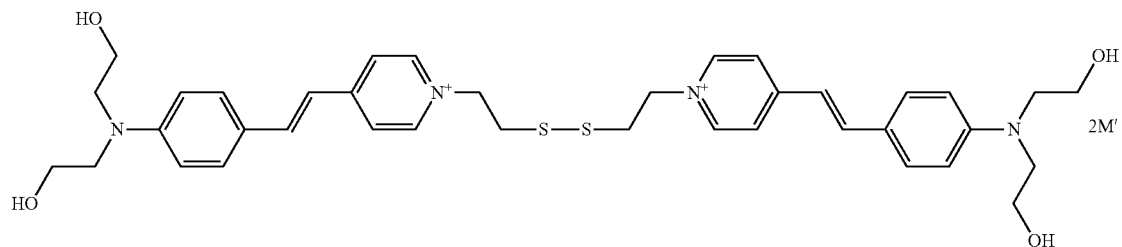
31
2M'

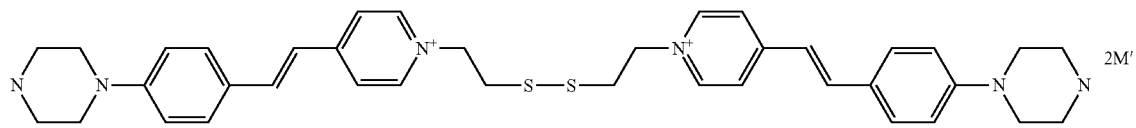
32
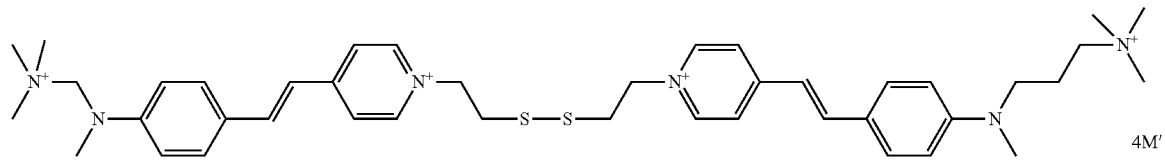
33
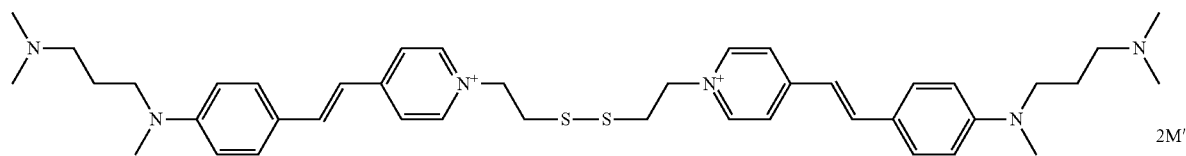
34
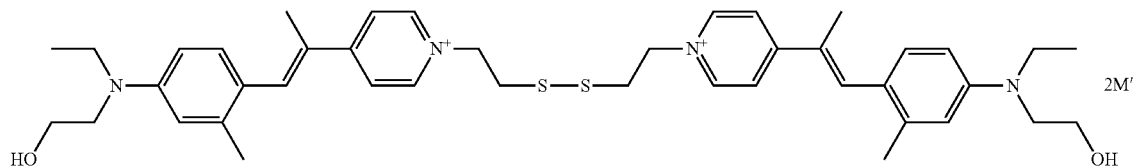
35
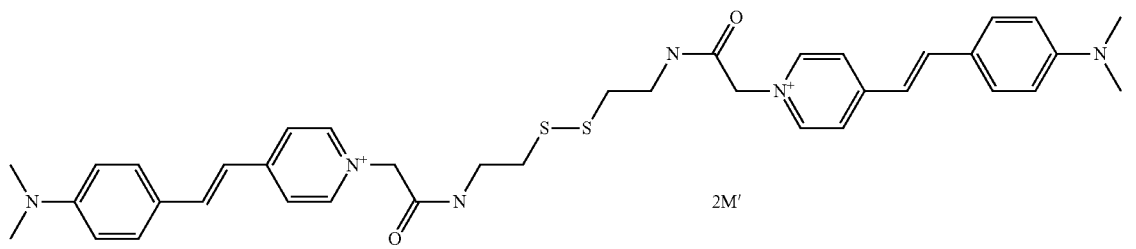
36
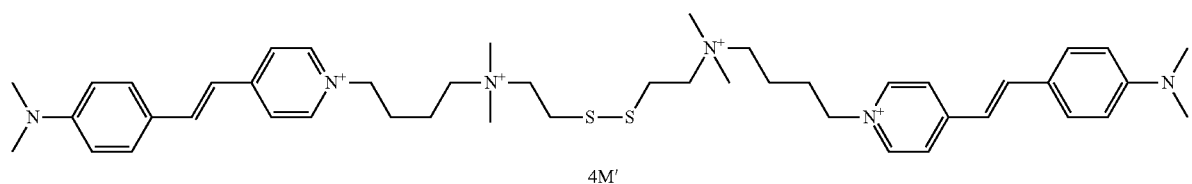
37
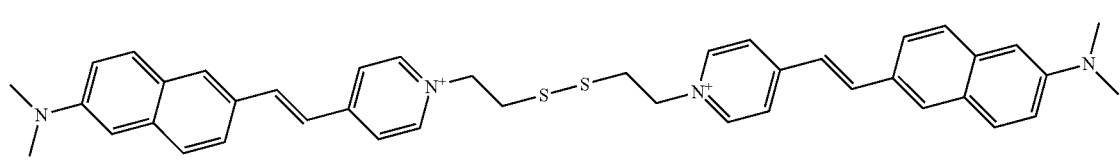
38

-continued
39
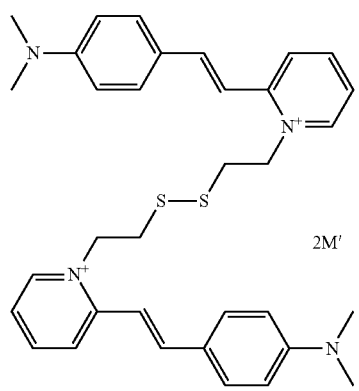
2M′
40
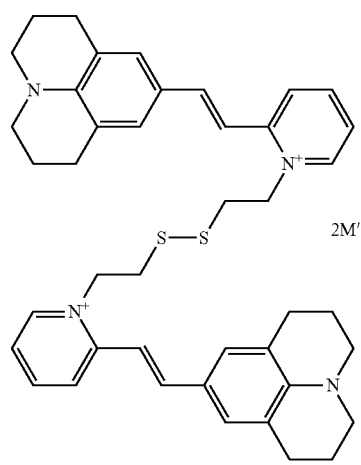
2M′
41
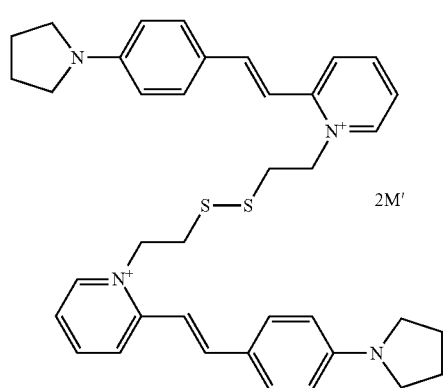
2M′
42
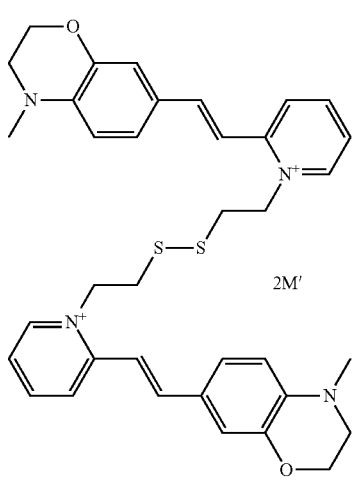
2M′
43
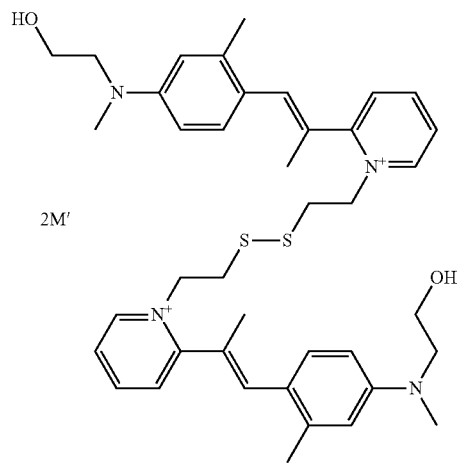
2M′
44
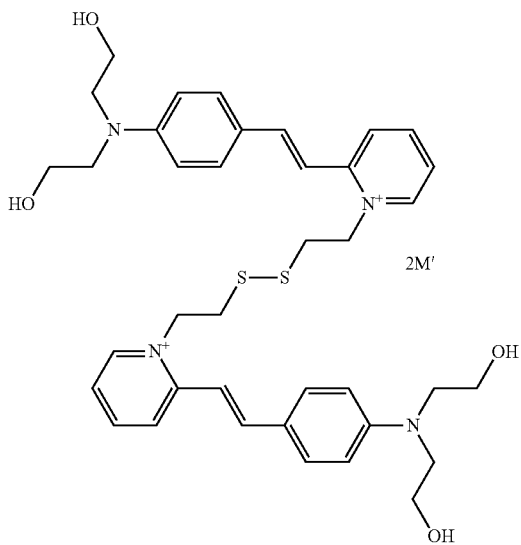
2M′

| | |
|---|---|
| 45 | 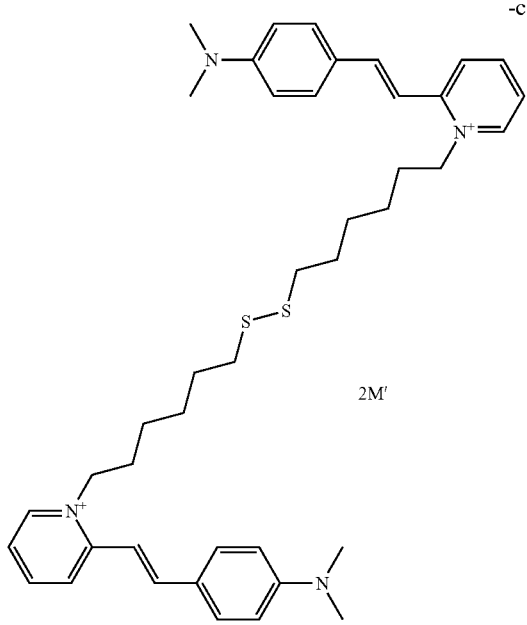 2M' |
| 46 | 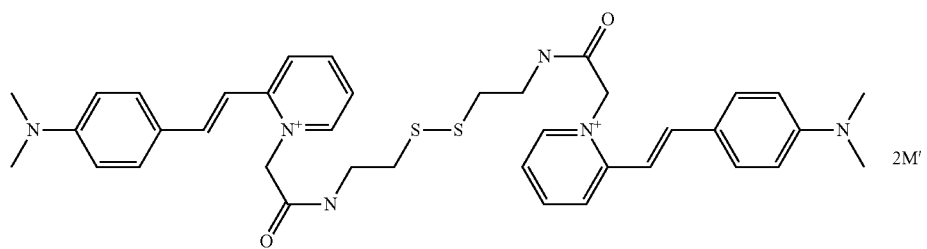 2M' |
| 47 | 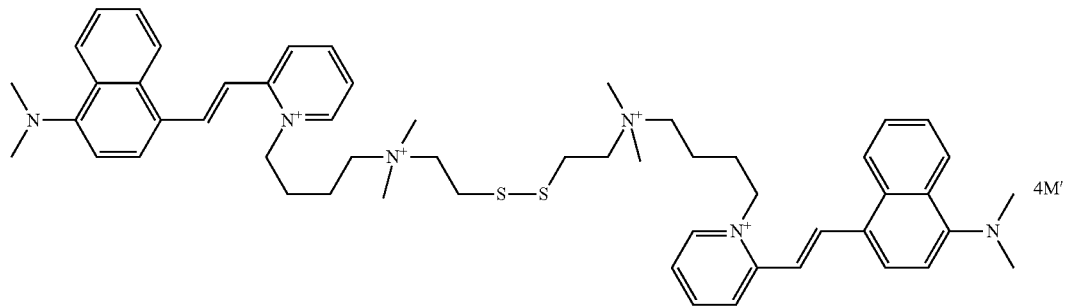 4M' |
| 48 | 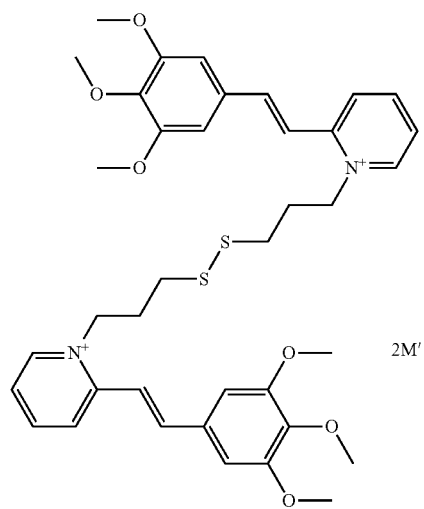 2M' |

-continued
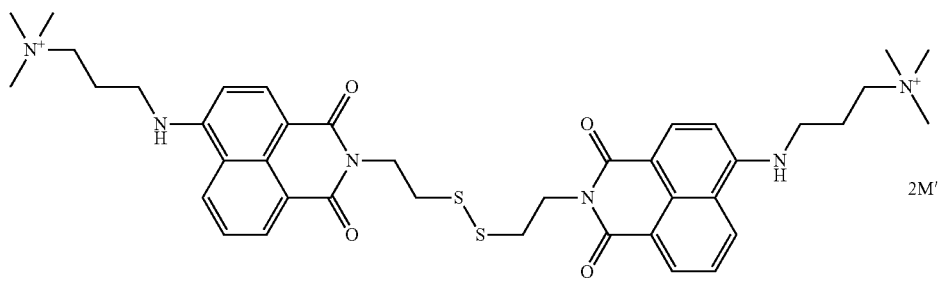
49
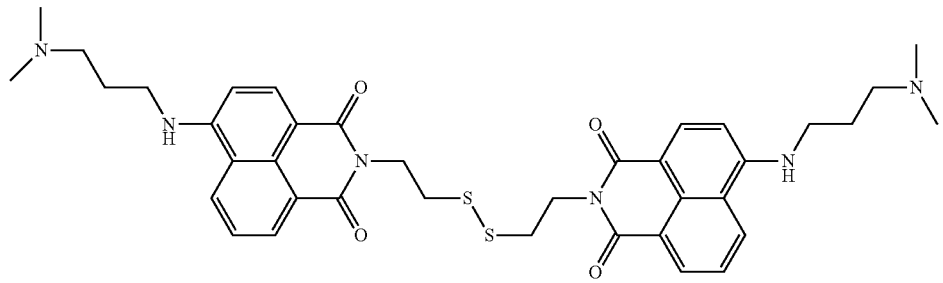
49a
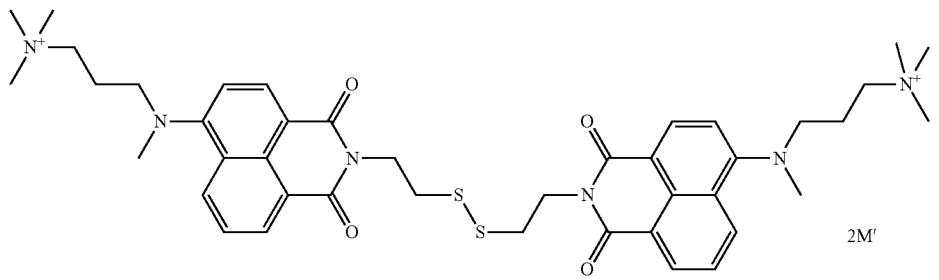
50
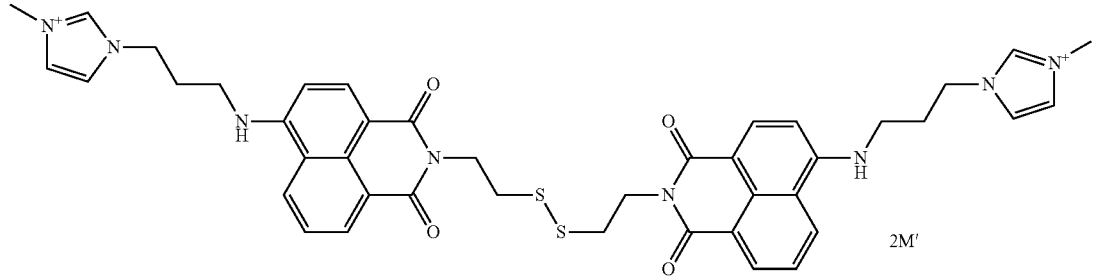
51
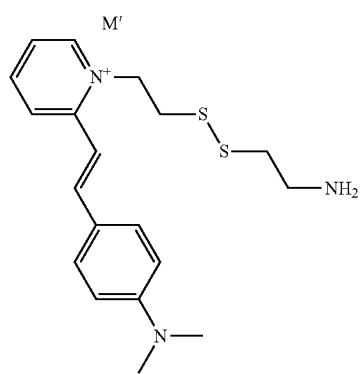
52
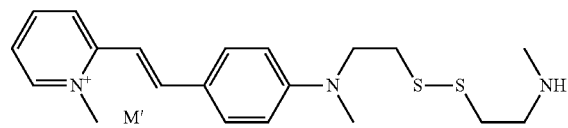
53

54
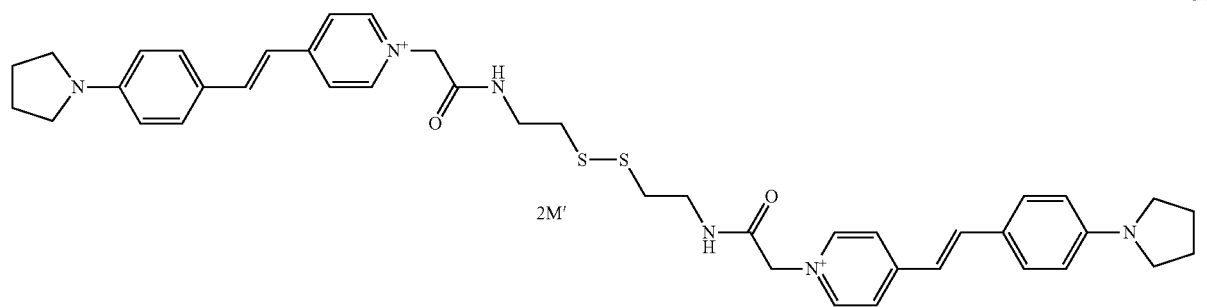
55
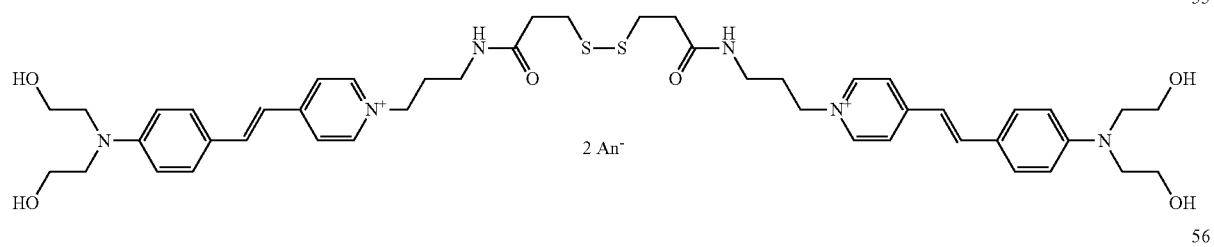
56
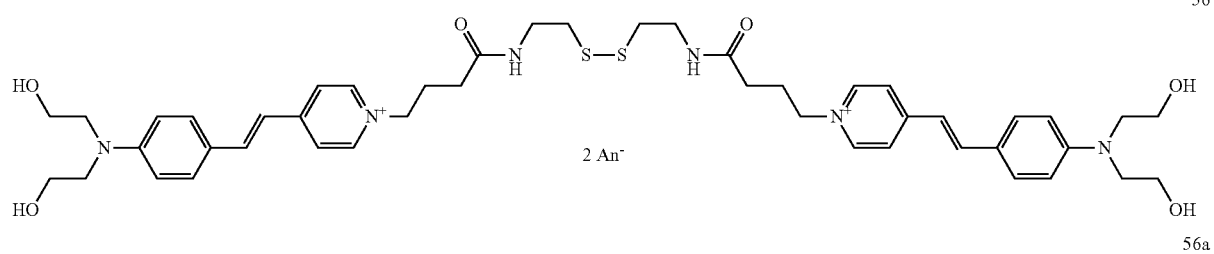
56a
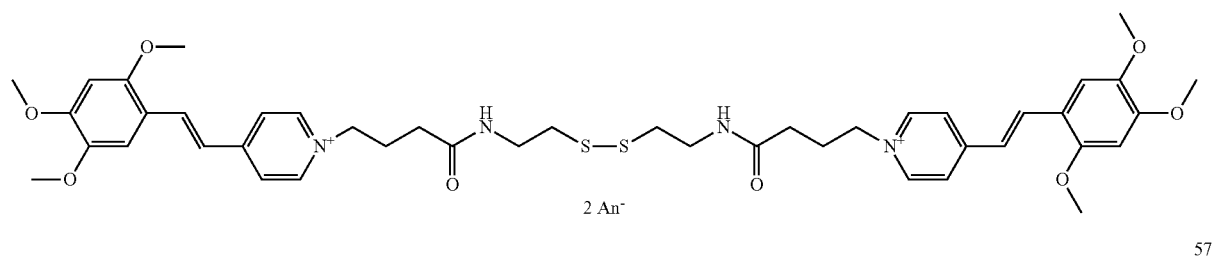
57
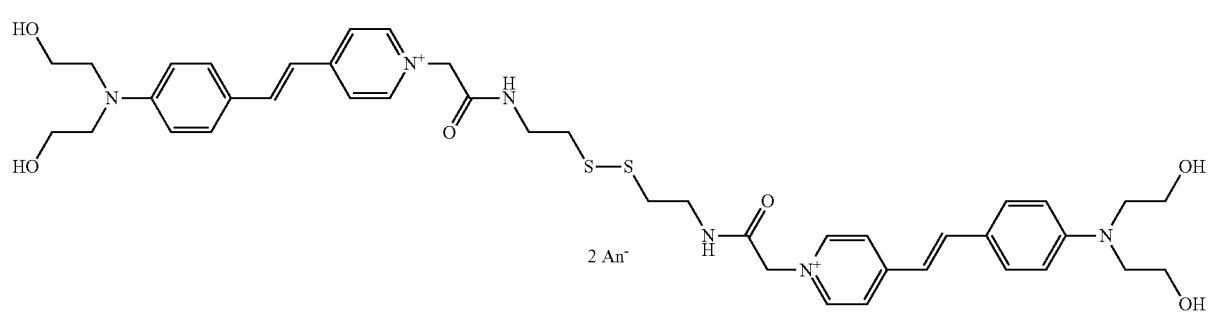
58
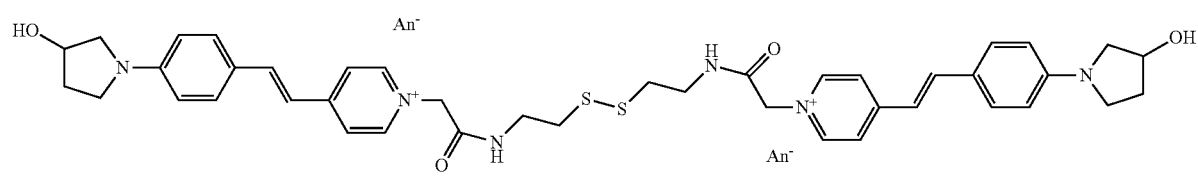

-continued
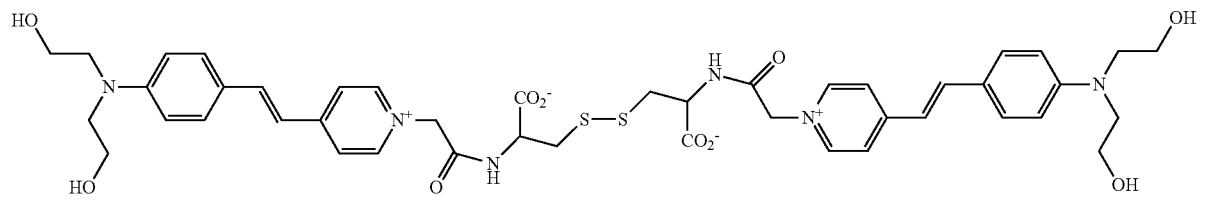
59
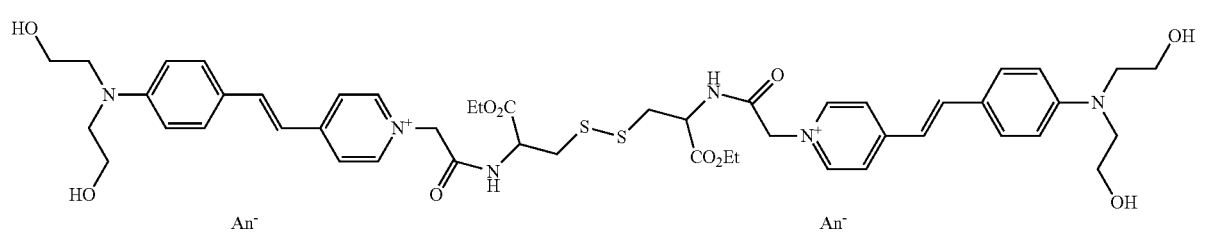
60
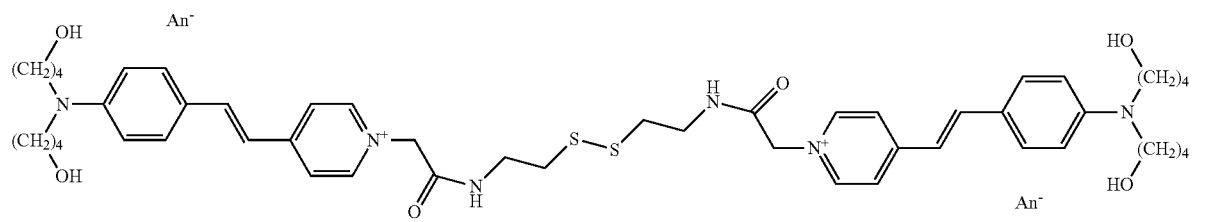
61
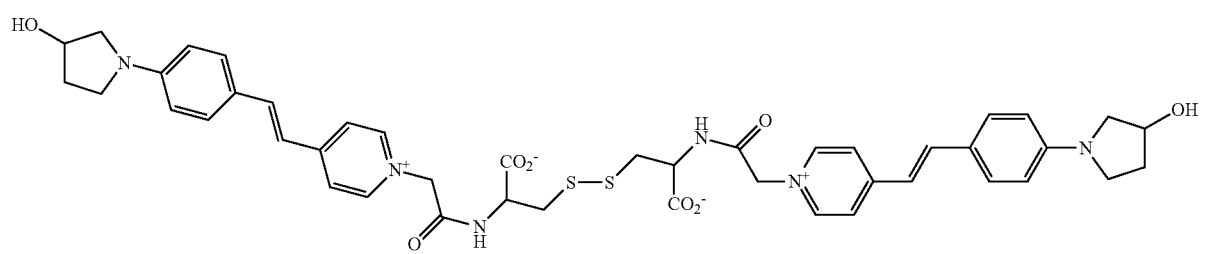
62
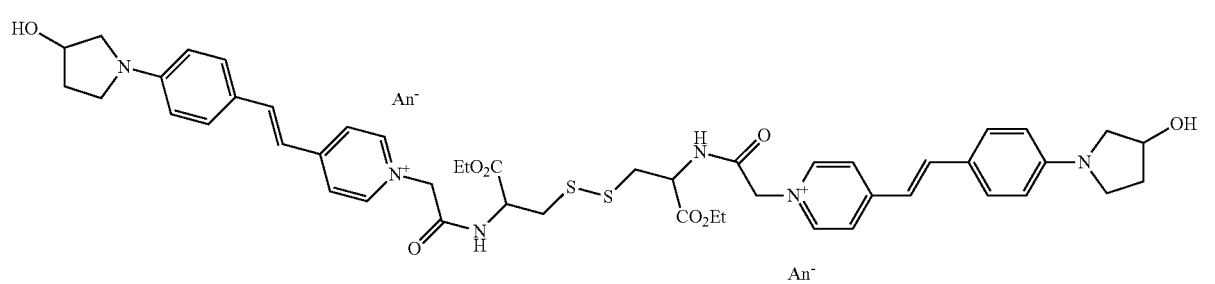
63
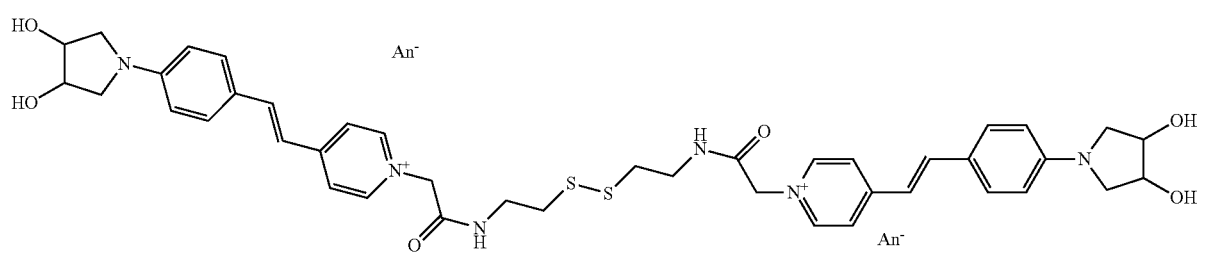
64

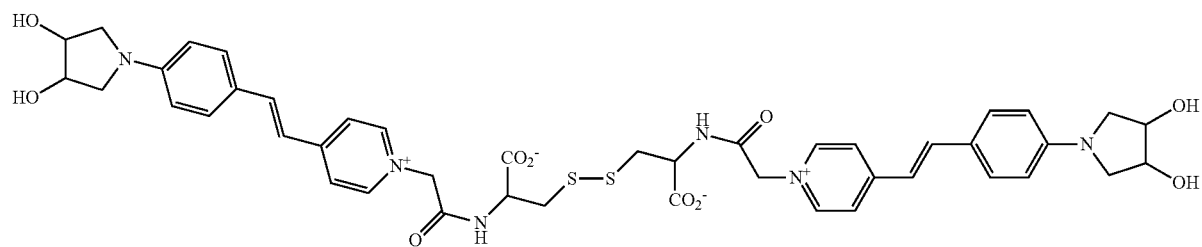
65
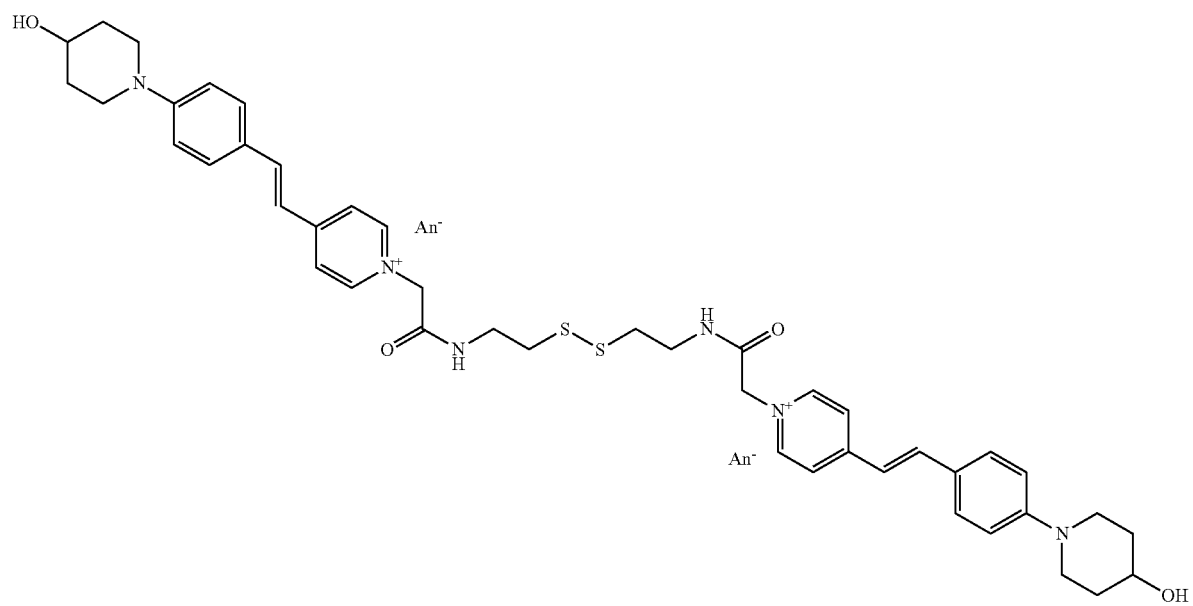
67
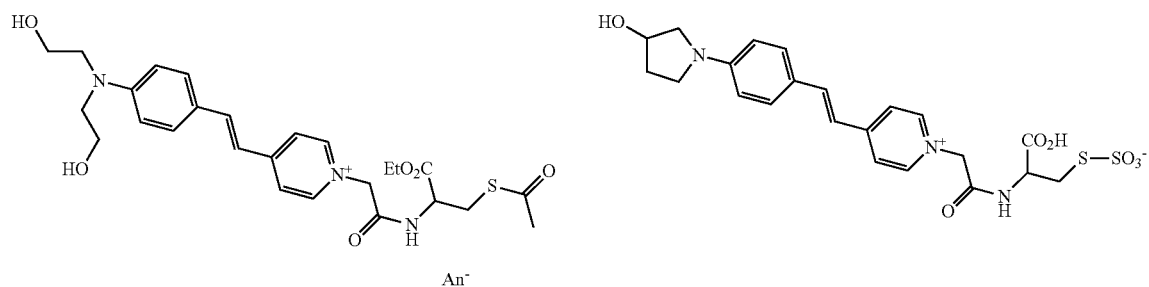
68
69
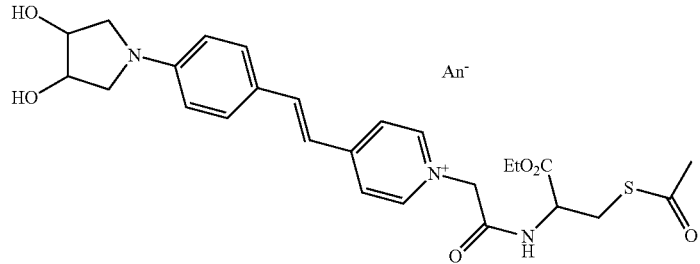
70

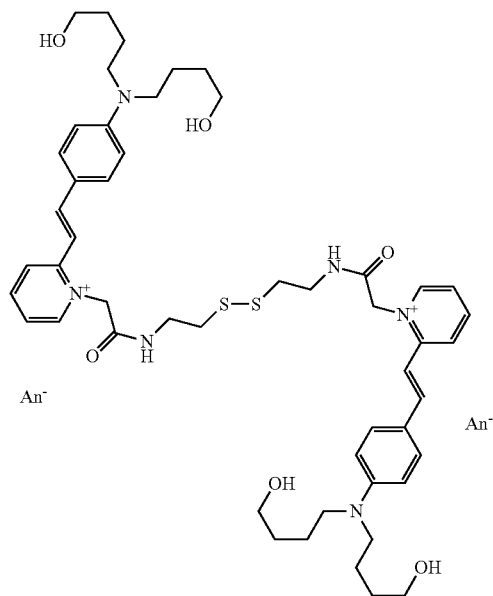
71
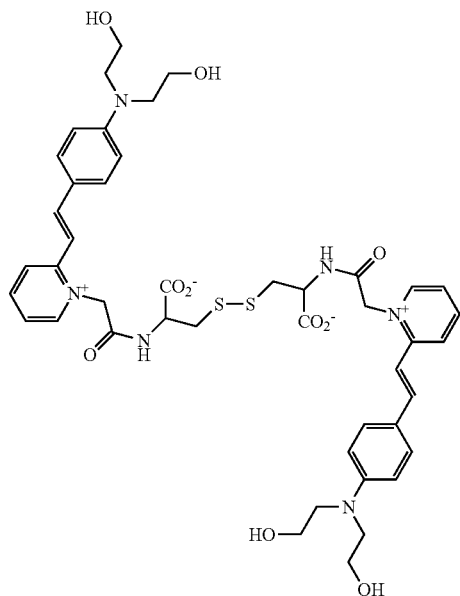
72
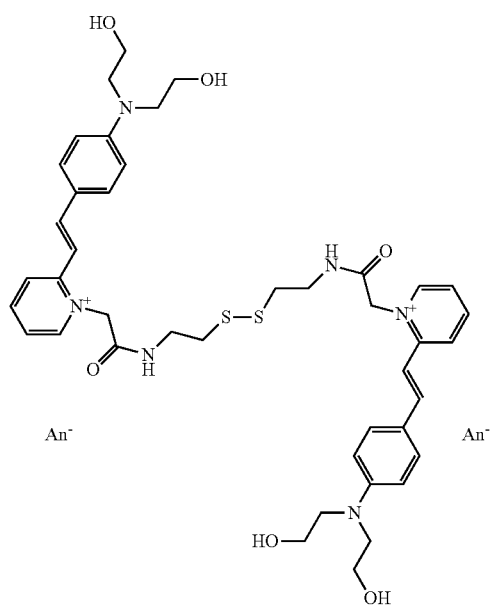
73
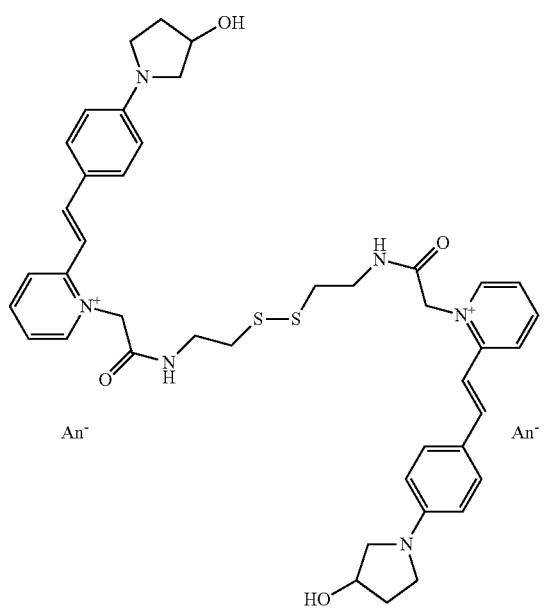
74

75
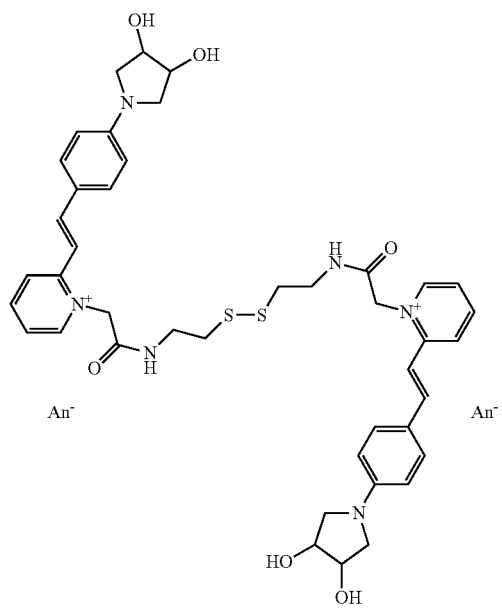
76
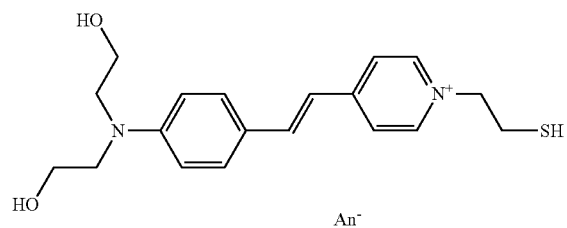
77
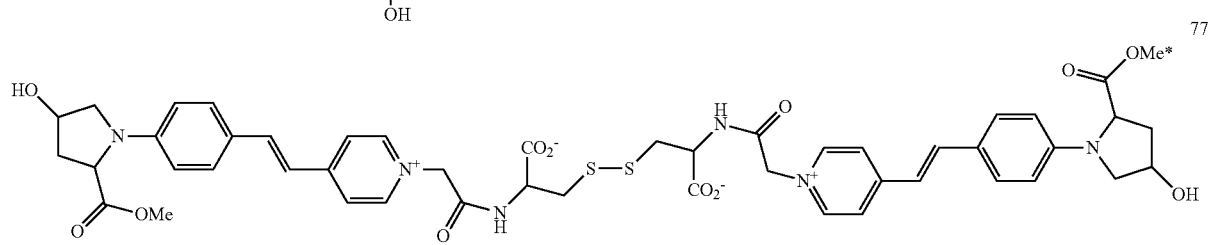
Me⁺ represents an alkali metal or ½ an alkaline-earth metal; or a methyl
78
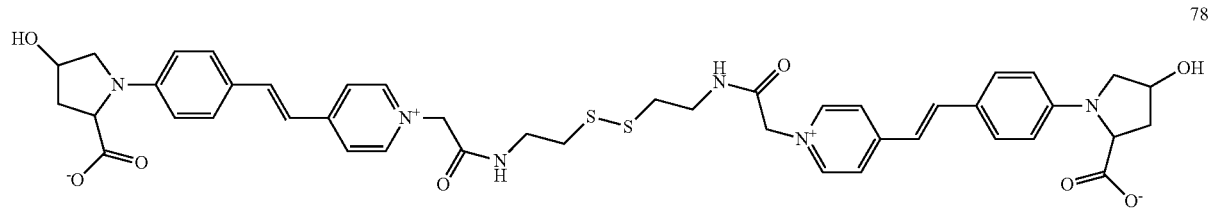
81
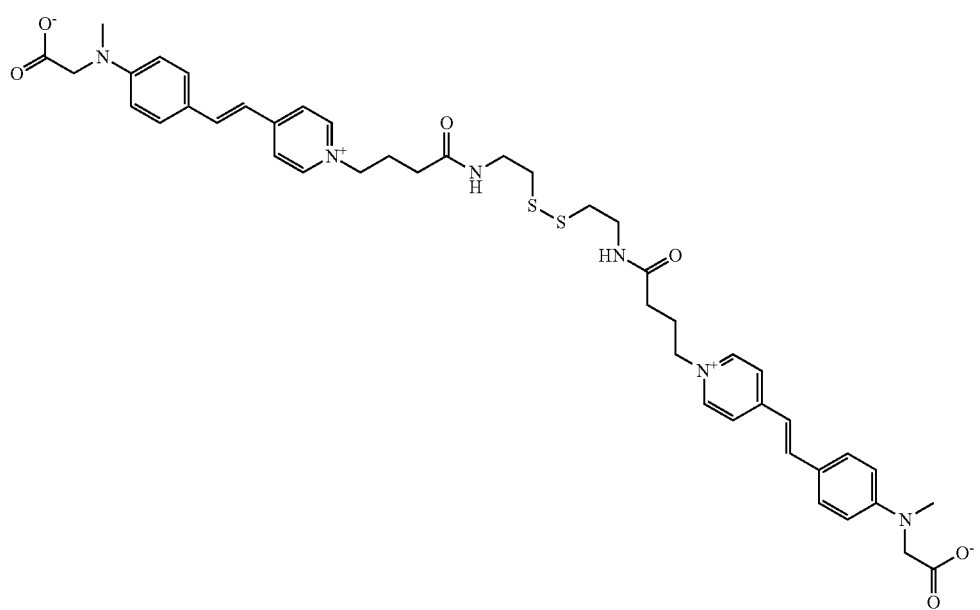

83
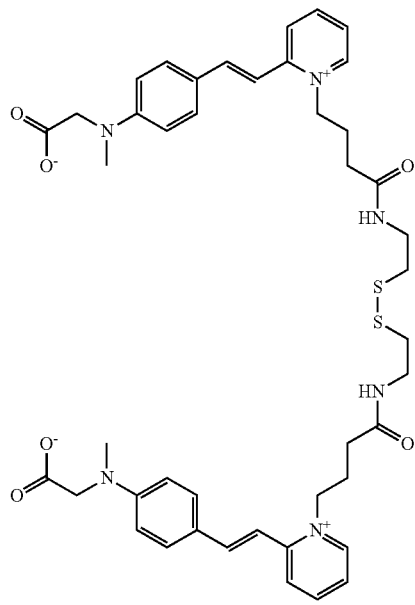
84
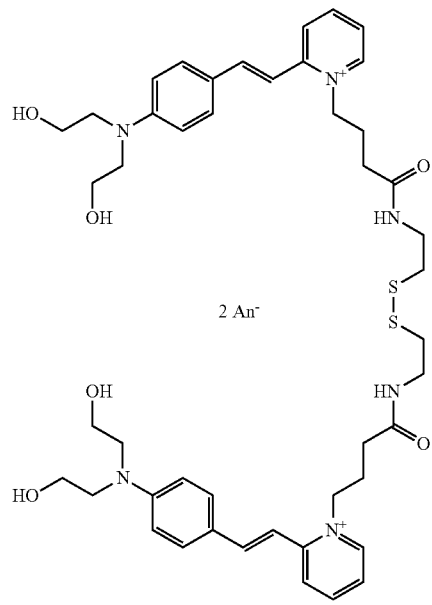
2 An⁻
86
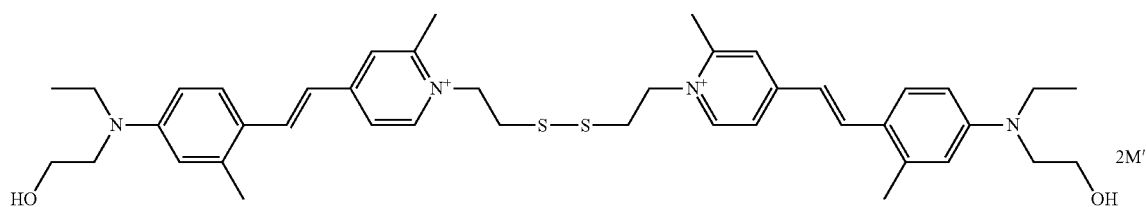
2M'
87
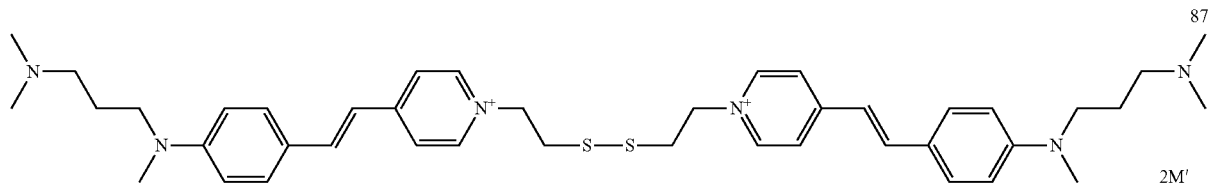
2M'
88
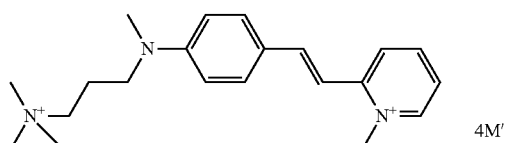
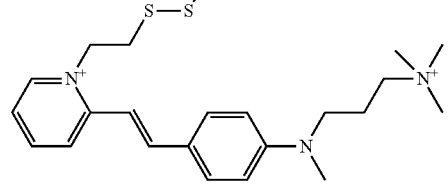
4M'
89
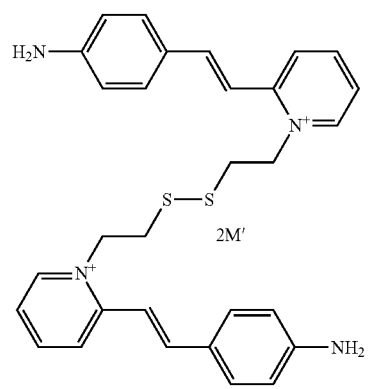
2M'

-continued
| 92 | 93 |
|---|---|
| 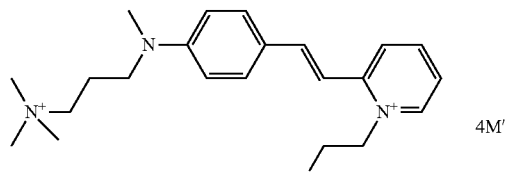 4M' | 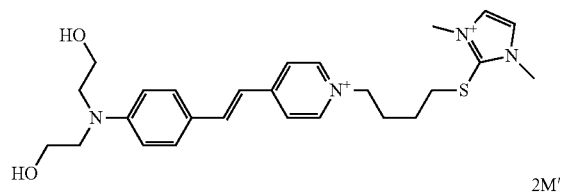 2M' |
| 94 | |
| 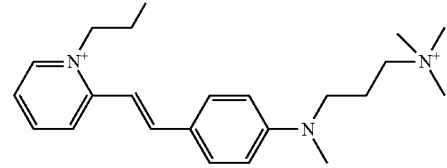 2M' | |
| 95 | |
| 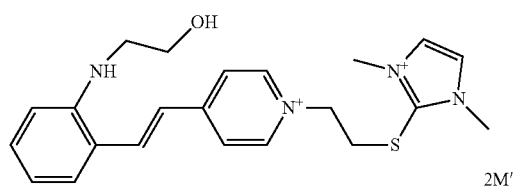 2M' | |
| 98 | 99 |
| 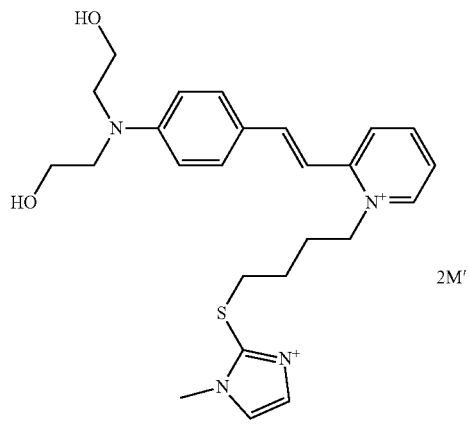 2M' | 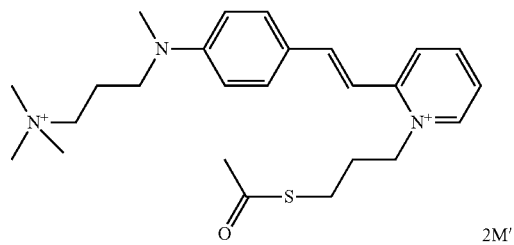 2M' |
| 100 | 101 |
| 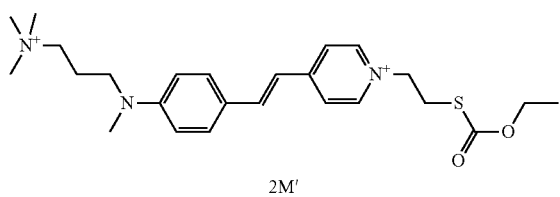 2M' | 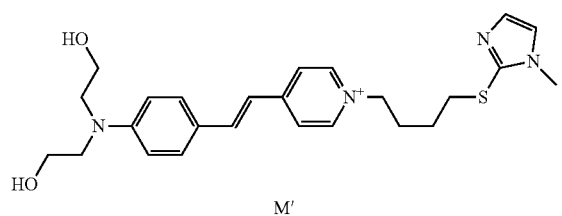 M' |

-continued
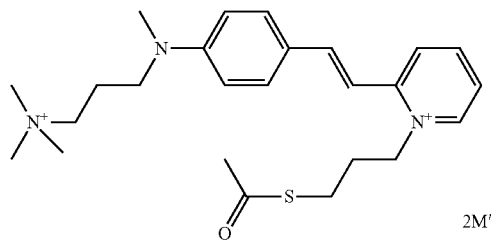
102
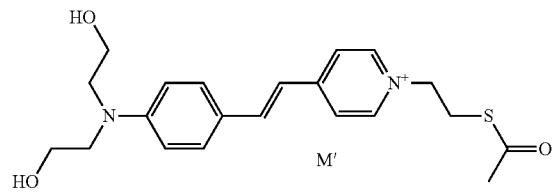
102
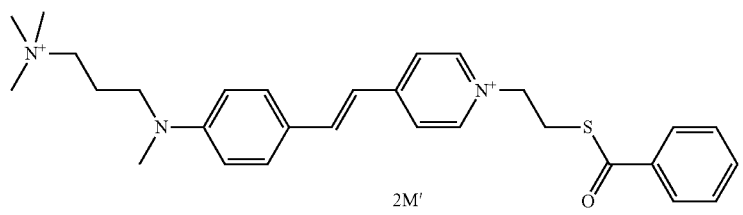
104
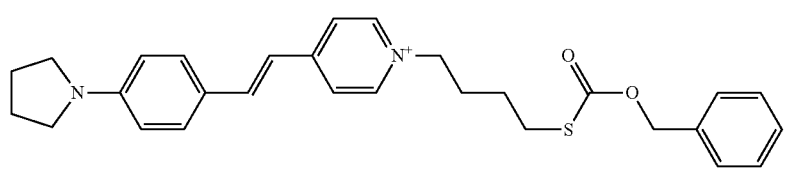
105
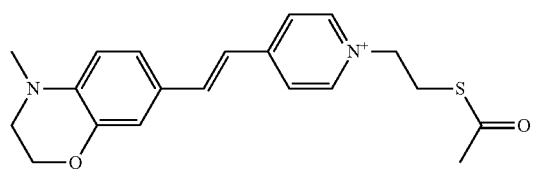
106
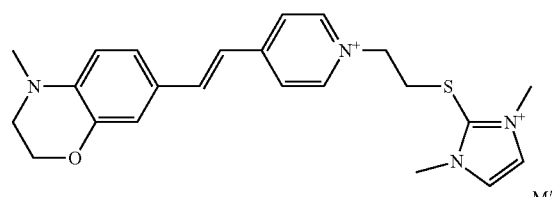
107
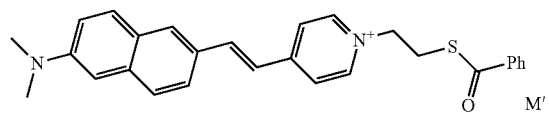
108
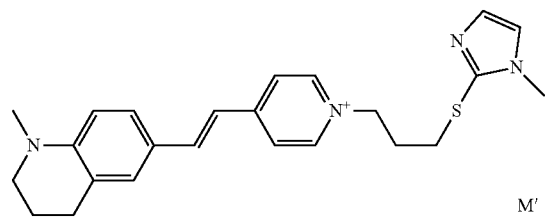
109
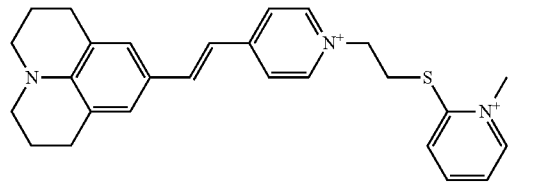
110
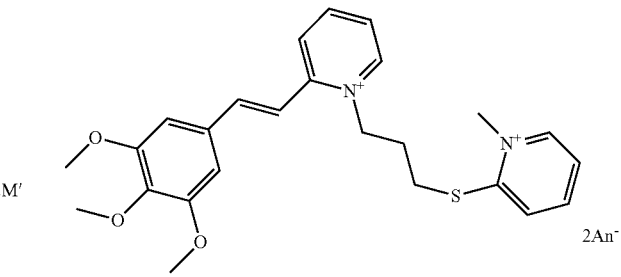
111

-continued

112
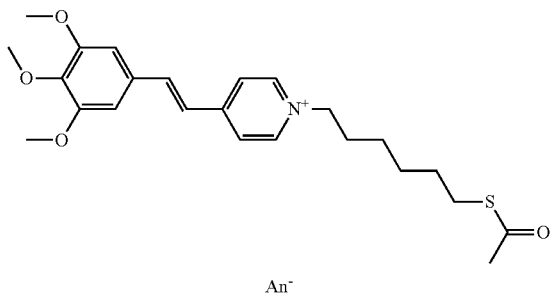
An⁻

113
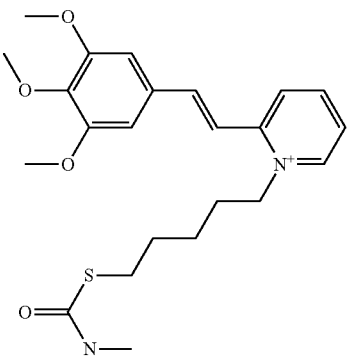
An⁻

114
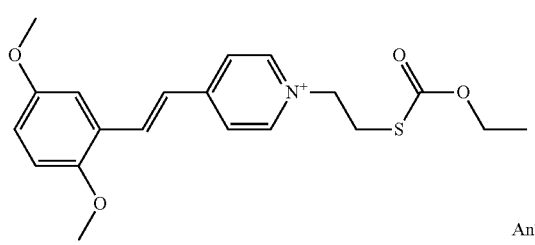
An⁻

115
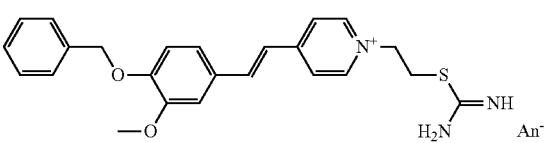
An⁻

116
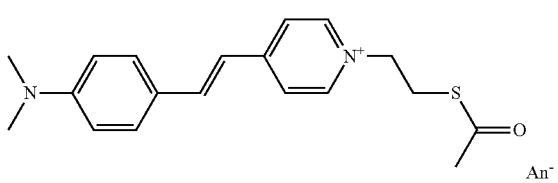
An⁻

117
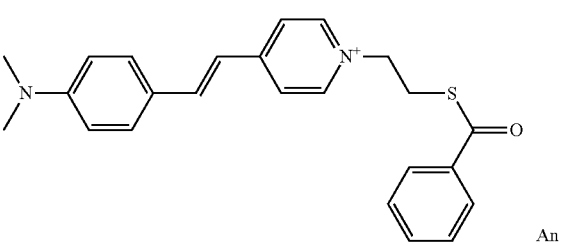
An⁻

118
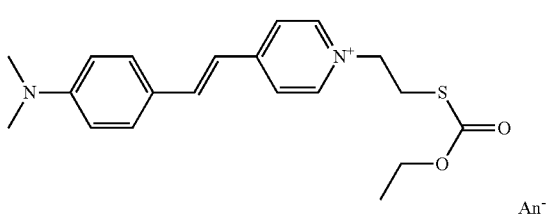
An⁻

119
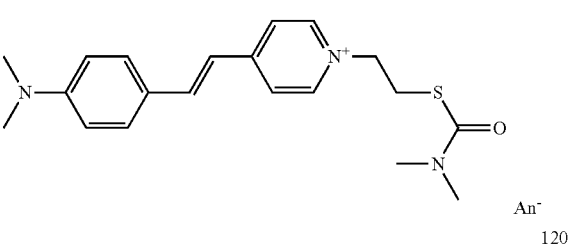
An⁻

120
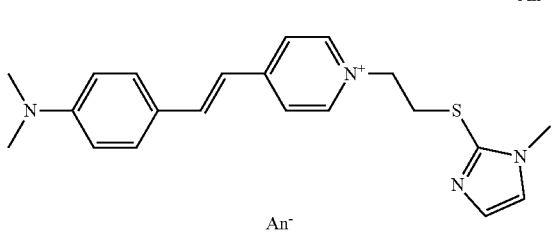
An⁻ with An⁻ and M', which may be identical or different, preferentially identical, representing anionic counterions. More particularly, the anionic counterion is chosen from halides such as chloride, alkyl sulfates such as methyl sulfate, mesylate and ½ (O=)$_2$SO$^{2-}$ or ½ SO$_4^{2-}$.

More preferentially, the disulfide, thiol or protected-thiol fluorescent dyes b) as defined previously are chosen from the compounds 31, 44, 49, 49a, 55, 56 and 56a in particular 44, 56 and 56a.

According to one particularly advantageous embodiment of the invention, the disulfide, thiol or protected-thiol fluorescent dye(s) b) are a dye comprising a "permanent" cationic charge, i.e. containing in its structure at least one quaternized nitrogen atom (ammonium) or quaternized phosphorus atom (phosphonium); preferentially quaternized nitrogen.

The composition according to the invention contains, in a cosmetic medium, a total amount of disulfide, thiol or protected-thiol fluorescent dye(s) as defined previously, in particular of formula (Ib) as defined previously, of generally between 0.001% and 30% inclusive, relative to the total weight of the composition which contains it (them).

Preferably, the total amount of disulfide, thiol or protected-thiol fluorescent dye(s) as defined previously, in particular of formula (Ib), is between 0.01% and 5% by weight inclusive, relative to the total weight of the composition. By way of example, the dye(s) is (are) in an amount of between 0.01% and 3%, better still between 0.05% and 2%, inclusive, relative to the total weight of the composition comprising it (them).

The Reducing Agents c)

The process for dyeing keratin fibres and the cosmetic composition according to the present invention also may optionally use, or comprise, c) one or more reducing agents.

The reducing agent(s) c) that are useful in the present invention are advantageously chosen from the compounds of formula (Ic) below, and also the addition salts thereof and mixtures thereof:

(Ic)

in which formula (Ic),

X represents P, S or $SO_2$, q represents an integer equal to 0 or 1, t represents an integer equal to 1 or 2, and $R_{10}$ represents a linear or branched, saturated or unsaturated $C_1$ to $C_{20}$ alkyl radical, optionally interrupted with a heteroatom, and/or optionally substituted with one or more radicals chosen from hydroxyl, halo, amine, carboxyl, (($C_1$-$C_{30}$)alkoxy)carbonyl, amido, (($C_1$-$C_{30}$)alkyl)aminocarbonyl, (($C_1$-$C_{30}$)acyl)amino, mono- or dialkylamino, and mono- or dihydroxylamino radicals.

Preferably, the reducing agent(s) of the invention are thiolated.

More particularly, the reducing agent(s) used according to the invention are chosen from organic compounds comprising one or more mercapto (—SH or —S—) groups, or disulfide (—S—S—) groups, preferably —SH groups, and at least one other function chosen from carboxylic acid, amine, amide, ester and alcohol functions and mixtures thereof.

According to one particular embodiment of the invention, the reducing agent(s) used in the invention are chosen from those of formulae i-1 and i-2, and also the organic or mineral acid or base salts thereof, optical isomers thereof and tautomers thereof, and the solvates such as hydrates:

  i-1

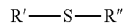  i-2 in which formulae i-1 and i-2:

R represents:
  a linear or branched ($C_1$-$C_8$)alkyl, preferably ($C_1$-$C_6$) alkyl group which is optionally substituted, preferably substituted, with one or more groups chosen from carboxy C(O)OH, (di)($C_1$-$C_4$)(alkyhamino, hydroxyl —OH, thiol —SH; and/or optionally interrupted with one or more heteroatoms or groups chosen from —O—, and —S—, —N(R'")—, C(O) or combinations thereof, such as —O—C(O)—, —C(O)—O—, —N(R'")—C(O)—, or —C(O)—N (R'")—; with R'" representing a hydrogen atom or a ($C_1$-$C_6$)alkyl group; or a (hetero)aryl group optionally substituted in particular with one or more hydroxyl, thiol or carboxy groups;

R' and R", which may be identical or different, represent a ($C_1$-$C_8$)alkyl group, preferably ($C_1$-$C_6$)alkyl group, substituted with one or more groups chosen from hydroxyl, thiol and carboxy;

or else R' and R" form, together with the sulfur atom which bears them, a 5- to 7-membered heterocyclic group, which is preferably saturated, which comprises from 1 to 3 heteroatoms, and which is optionally substituted (in particular with one or more ($C_1$-$C_6$)alkyl groups optionally substituted with one or more hydroxyl, thiol or carboxy groups), more preferentially the heterocyclic group is a dithiolane group optionally substituted with a ($C_1$-$C_6$)alkyl group optionally substituted with one or more carboxy groups.

According to one particular embodiment of the invention, the reducing agents are of formula i-1, in particular those for which R represents a linear or branched ($C_1$-$C_8$) alkyl group, preferably ($C_1$-$C_6$) alkyl group, which is substituted with one or more groups chosen from carboxy C(O)OH, amino, hydroxyl —OH and thiol —SH; and/or optionally interrupted with one or more heteroatoms or groups chosen from —O—, —N(R'")—, C(O) or combinations thereof such as —O—C(O)—, —C(O)—O—, —N(R'")—C(O)— or —C(O)—N(R'"). Preferably, R represents a linear or branched, uninterrupted ($C_1$-$C_8$)alkyl group, preferably ($C_1$-$C_6$)alkyl group.

According to another particular embodiment of the invention, the reducing agents are of formula i-1 for which R represents:
  a phenyl group optionally substituted with one or more hydroxyl, thiol or carboxy groups; or
  heteroaryl comprising from 5 to 10 ring members, which is preferably bicyclic comprising 9 or 10 ring members, comprising from 1 to 4 heteroatoms chosen from O, S or N, preferably N, optionally substituted with one or more hydroxyl or thiol groups.

According to another particular embodiment of the invention, the reducing agents are of formula i-2, in particular those for which R' and R", which may be identical or different, represent a ($C_1$-$C_8$)alkyl group, preferably ($C_1$-$C_6$) alkyl group, substituted with one or more groups chosen from hydroxyl, thiol and carboxy.

According to another particular embodiment of the invention, the reducing agents are of formula i-2, in particular those for which R' and R" form, together with the sulfur atom which bears them, a 5- to 7-membered heterocyclic group, which is preferably saturated, which comprises from 1 to 3 heteroatoms, and which is optionally substituted with one or more ($C_1$-$C_6$)alkyl groups optionally substituted with one or more hydroxyl, thiol or carboxy groups, more preferentially the heterocyclic group is a dithiolane group optionally substituted with a ($C_1$-$C_6$)alkyl group optionally substituted with one or more hydroxyl, thiol or carboxy groups.

Preferably, the reducing agent(s) c) are chosen from thioglycolic acid, thiolactic acid, glyceryl monothioglycolate, cysteamine, N-acetylcysteamine, N-propionylcysteamine, cysteine, N-acetylcysteine, thiomalic acid, pantetheine, 2,3-dimercaptosuccinic acid, N—(mercaptoalkyl)-ω-hydroxyalkylamides, N-mono- or N,N-dialkylmercapto-4-butyramides, aminomercaptoalkylamides, N-(mercaptoalkyl) succinamic acid and N-(mercaptoalkyl)succinimide derivatives, alkylamino mercaptoalkylamides, the azeotropic mixture of 2-hydroxypropyl thioglyconate and of (2-hydroxy-1-methyl)ethyl thioglycolate, mercaptoalkylaminoamides, N-mercaptoalkylalkanediamides and formamidinesulfinic acid derivatives, salts thereof, and mixtures thereof.

More particularly, the reducing agents comprising at least one mercapto or disulfide group of the invention are chosen from thioglycolic acid, thiolactic acid or 2-mercaptopropionic acid, cysteine, cysteamine, homocysteine, glutathione, thioglycerol, thiomalic acid, 3-mercaptopropionic acid, thiodiglycol, 2-mercaptoethanol, dithiothreitol, thioxanthine, thiosalicylic acid, thiodiglycolic acid, lipoic acid, N-acetylcysteine, and thioglycolic or thiolactic acid esters and amides, in particular glyceryl monothioglycolate, and mixtures of these compounds.

The thiol reducing agent(s) may be used in particular in the form of salts, in particular alkali metal salts such as sodium and potassium salts, alkaline-earth metal salts, for example magnesium and calcium salts, ammonium salts, amine salts and amino alcohol salts. Ammonium thioglycolate may thus be used as reducing agent.

Preferably, the reducing agent(s) c) are also chosen from salts such as sodium sulfite, sodium dithionite or sodium thiosulfate, and mixtures thereof.

The reducing agent(s) c) of the invention are chemical and are advantageously applied in the form of an aqueous solution of which the content of chemical reducing agents is preferably between 0.01% and 10% by weight and more preferentially between 0.1% and 5% by weight, relative to the total weight of the aqueous solution.

According to one particular embodiment of the invention, the dyeing process does not use any reducing agent. In this embodiment, the direct dye(s) a) is (are) preferably chosen from cationic direct dyes.

According to this preferred embodiment of the invention, the cosmetic composition comprising ingredients a) and b) does not comprise any reducing agent.

According to one particular embodiment of the invention, the dyeing process uses one or more reducing agent(s). In this embodiment, the direct dye(s) a) is (are) preferably chosen from anionic direct dyes.

The Oxidizing Agents d)

The process for dyeing keratin fibres and the cosmetic composition according to the present invention may also optionally use, or comprise, one or more oxidizing agents d).

The term "oxidizing agent" is intended to mean an oxidizing agent other than atmospheric oxygen.

More particularly, the oxidizing agent(s) d) are chosen from hydrogen peroxide, hydrogen peroxide-generating systems, urea peroxide, alkali metal bromates or ferricyanides, peroxygenated salts, for instance persulfates, perborates, peracids and precursors thereof and percarbonates of alkali metals or alkaline-earth metals, and mixtures thereof.

Preferably, the oxidizing agent(s) d) are chosen from hydrogen peroxide and hydrogen peroxide-generating systems.

According to a preferred embodiment, the hydrogen peroxide-generating system(s) are chosen from urea peroxide; polymeric complexes that can release hydrogen peroxide, chosen from polyvinylpyrrolidone/$H_2O_2$; oxidases; perborates; and percarbonates.

Preferably, the chemical oxidizing agent(s) d) are hydrogen peroxide, and more preferentially hydrogen peroxide in aqueous solution (aqueous hydrogen peroxide).

The oxidizing agent(s) d) are advantageously applied in the form of an aqueous solution of which the content of chemical oxidizing agents is preferably between 0.05% and 5% by weight and more preferentially between 0.1% and 2% by weight, relative to the total weight of the aqueous solution.

According to one preferred embodiment of the invention, the dyeing process does not use a chemical oxidizing agent.

According to this preferred embodiment of the invention, the cosmetic composition comprising ingredients a) and b) does not comprise any oxidizing agent.

The Cosmetic Medium and the Solvents

The direct dye(s) a), as defined previously, and b) the disulfide, thiol or protected-thiol fluorescent dye(s), as defined previously, and also, when they are present, the oxidizing agent(s) d) and/or the reducing agent(s) c), may be dissolved beforehand before being applied to the keratin fibres.

In other words, the ingredients used in the dyeing process of the present invention may be present in one or more compositions.

The composition(s) comprising the ingredients according to the present invention are cosmetic compositions, i.e. they are preferably aqueous. Besides water, they may comprise one or more organic solvents, or mixtures thereof.

Examples of organic solvents that may be mentioned include linear or branched $C_2$ to $C_4$ alkanols, such as ethanol and isopropanol; glycerol; polyols and polyol ethers, for instance 2-butoxyethanol, propylene glycol, hexylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The pH

The pH of the composition(s) used in the dyeing process of the invention and of the composition of the invention comprising ingredients a) and b) as defined previously is preferably between 2 and 12 and more preferentially between 3 and 11. It may be adjusted to the desired value by means of acidifying or alkaline agents usually used in the dyeing of keratin fibres, or alternatively using standard buffer systems.

The pH of the composition which comprises the ingredients a) and/or b) and/or c) and that of the composition(s) used in the dyeing process of the invention (in particular the composition which comprises the reducing agent(s) c) when they are present) is preferably between 2 and 11 inclusive, preferably between 2.5 and 10.5 inclusive, more preferentially between 3 and 10 inclusive.

Among the acidifying agents, mineral and organic acids as defined previously, mention may be made, by way of example, of mineral or organic acids, for instance hydrochloric acid, orthophosphoric acid or sulfuric acid, carboxylic acids, for instance acetic acid, tartaric acid, citric acid and lactic acid, and sulfonic acids.

The alkaline agent(s) may be chosen especially from mineral, organic or hybrid alkaline agents, and mixtures thereof.

The mineral alkaline agent(s) are preferably chosen from ammonia, alkaline carbonates or bicarbonates such as ammonium, sodium or potassium carbonate or bicarbonate, ammonium, sodium or potassium hydroxide, or mixtures thereof.

The organic alkaline agent(s) are preferably chosen from organic amines with a $pK_b$ at 25° C. of less than 12, preferably of less than 10 and more advantageously still of less than 6. It should be noted that it is the pKb corresponding to the function of highest basicity. In addition, the organic amines do not comprise any alkyl or alkenyl fatty chain comprising more than ten carbon atoms.

The organic alkaline agent(s) are preferably chosen from alkanolamines, in particular mono-, di- or tri-hydroxy($C_1$-$C_6$)alkylamines, such as triethanolamine, oxyethylenated and/or oxypropylenated ethylenediamines, amino acids, polyamines of formula (Ie) below, and mixtures thereof:

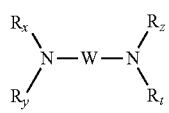

in which formula (Ie), W is a divalent $C_1$ to $C_6$ alkylene radical optionally substituted with one or more hydroxyl groups or a $C_1$ to $C_6$ alkyl radical, and/or optionally interrupted with one or more heteroatoms such as O, or $NR_u$; $R_x$, $R_y$, $R_z$, $R_t$, and $R_u$, which are identical or different, represent a hydrogen atom, a $C_1$ to $C_6$ alkyl or $C_1$ to $C_6$ hydroxyalkyl or $C_1$ to $C_6$ aminoalkyl radical.

Examples of amines of formula (Ie) that may be mentioned include 1,3-diaminopropane, 1,3-diamino-2-propanol, spermine and spermidine.

The term "alkanolamine" is intended to mean an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$ to $C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that may be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

As amino acids that may be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to the following formula (IIe) R—$CH_2$—CH($NH_2$)—C(O)—OH and also the salts thereof; in which formula (IIe), R represents a group chosen from imidazolyl, preferably imidazolyl-4-yl; aminopropyl; aminoethyl; —$(CH_2)_2$N(H)—C(O)—$NH_2$; and $(CH_2)_2$—N(H)—C(NH)—$NH_2$. The compounds corresponding to formula (IIe) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and balenine.

The organic amine may also be chosen from compounds comprising a guanidine function. As amines of this type that may be used in the present invention, besides arginine, which has already been mentioned as an amino acid, mention may be made in particular of creatine, creatinine, 1,1-dimethylguanidine, 1,1-diethylguanidine, glycocyamine, metformin, agmatine, n-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the alkaline agent(s) that are useful in the invention are chosen from aqueous ammonia, alkanolamines, amino acids in neutral or ionic form, in particular basic amino acids, and preferably corresponding to those of formula (IIe).

More preferentially, the alkaline agent(s) are chosen from aqueous ammonia, ammonium bicarbonate, ammonium hydroxide, mono-, di- or tri-hydroxy($C_1$-$C_6$)alkylamines, such as MEA, and mixtures thereof.

Forms of the Composition

The composition(s) comprising the direct dye(s) a) as defined previously, and the disulfide, thiol or protected-thiol fluorescent dye(s) b), as defined previously, may be in various presentation forms, such as in the form of liquids, lotions, creams or gels or in any other form that is suitable for dyeing keratin fibres.

It (they) may also be packaged under pressure in an aerosol container in the presence of a propellant or in a non-aerosol container and may optionally form a foam.

Additives

When the ingredients used in the dyeing process according to the present invention are present in one or more composition(s), said composition(s) may also optionally comprise one or more additives, different from the ingredients of the invention and among which mention may be made of fatty substances, cationic, anionic, non-ionic, amphoteric or zwitterionic surfactants, cationic, anionic, non-ionic or amphoteric polymers or mixtures thereof, anti-dandruff agents, anti-seborrhoea agents, agents for preventing hair loss and/or for promoting hair regrowth, vitamins and provitamins including panthenol, sunscreens, mineral or organic pigments, sequestrants, plasticizers, solubilizers, mineral or organic thickeners, especially polymeric thickeners, opacifiers or nacreous agents, antioxidants, hydroxy acids, fragrances, preservatives, pigments and ceramides.

Needless to say, those skilled in the art will take care to select this or these optional additional compound(s) such that the advantageous properties intrinsically associated with the composition(s) in accordance with the invention are not, or are not substantially, adversely affected by the envisaged addition(s).

The above additives may generally be present in an amount, for each of them, of between 0 and 20% by weight relative to the total weight of the composition comprising them.

The Dyeing Process

The process for dyeing keratin materials, in particular keratin fibres, in particular human keratin fibres such as the hair, according to the present invention comprises the application to said keratin fibres of the following ingredients:
- a) one or more direct dye(s) as defined previously, and
- b) one or more disulfide, thiol or protected-thiol fluorescent dye(s) as defined previously;

it being understood that the direct dye(s) a) (ingredients a)) or the disulfide, thiol or protected-thiol fluorescent dye(s) (ingredients (b)) is (are) applied to said keratin materials jointly or sequentially and that the direct dye(s) a is (are) different from disulfide, thiol or protected-thiol fluorescent direct dye(s) b).

In other words, the dyeing process according to the present invention may be performed in one or more steps.

According to one particularly preferred embodiment, the direct dye(s) a) and the disulfide, thiol or protected-thiol fluorescent dye(s) b), as defined previously, are applied jointly (or together), i.e. simultaneously, to the keratin materials. According to this embodiment, the dyeing process is performed in one step.

According to this one-step embodiment, the process comprises a step of applying to said keratin materials a cosmetic composition according to the invention which comprises one or more preferably ionic, more preferentially cationic or anionic, direct dyes a) as defined previously, and one or more disulfide, thiol or protected-thiol fluorescent dyes b) as defined previously.

According to another particularly preferred embodiment, the direct dye(s) a), as defined previously, and the disulfide, thiol or protected-thiol fluorescent dye(s) b), as defined previously, are applied to said keratin materials sequentially, i.e. successively. According to this other embodiment, the dyeing process is performed in at least two steps.

According to a first embodiment in at least two steps, the disulfide, thiol or protected-thiol fluorescent dye(s) b), as defined previously, is (are) applied to the keratin materials after the direct dye(s) a) as defined previously. In other words, the disulfide, thiol or protected-thiol fluorescent dye(s) b), as defined previously, is (are) applied after the direct dye(s) a) as defined previously.

According to this first embodiment, the process for dyeing keratin materials comprises at least the following two successive steps:
- a first step of applying to said keratin materials a cosmetic composition comprising one or more direct dye(s) a) as defined previously, followed by
- a second step of applying to said keratin materials a cosmetic composition which comprises one or more disulfide, thiol or protected-thiol fluorescent dye(s) b) as defined previously.

According to one preferred embodiment in at least two steps, the direct dye(s) a), as defined previously, is (are) applied to the keratin materials after the fluorescent dye(s) b) as defined previously. In other words, the direct dye(s) a), as defined previously, is (are) applied after the disulfide, thiol or protected-thiol fluorescent dye(s) b) as defined previously.

According to this preferred embodiment, the process for dyeing keratin materials comprises at least the following two successive steps:
- a first step of applying to said keratin materials a cosmetic composition comprising one or more disulfide, thiol or protected-thiol fluorescent dye(s) b) as defined previously, followed by
- a second step of applying to said keratin materials a cosmetic composition comprising one or more direct dye(s) a) as defined previously.

The keratin fibres, in particular human keratin fibres such as the hair, which are treated with the process of the invention, can be treated with one or more reducing agents c) as defined previously.

The step of treating with one or more reducing agents c) as defined previously can be carried out before the step(s) of treating with the direct dye(s) a) and the disulfide, thiol or protected-thiol fluorescent dye(s) b). Preferably, the keratin fibres are rinsed with water after the step of treating with the reducing agent(s) c).

According to one particular embodiment of the invention, the keratin fibres, in particular human keratin fibres such as the hair, of the process of the invention, are pretreated with a detergent composition, i.e. a composition comprising at least one anionic surfactant and/or at least one amphoteric compound.

The clean hair may be wet or dry before the application of the dyes a) and/or b).

According to one particular embodiment of the process of the invention, the direct dye(s) a), as defined previously, and the disulfide, thiol or protected-thiol fluorescent dye(s) b), as defined previously, are applied jointly to the keratin materials; preferably, the process comprises a step of applying to the keratin fibres a cosmetic composition which comprises one or more direct dye(s) a), as defined previously, and one or more disulfide, thiol or protected-thiol fluorescent dye(s) b) as defined previously.

Preferably, the ingredients a) and b) are applied to the keratin materials in a bath ratio that may range from 0.1 to 10 and more particularly from 0.2 to 8. For the purposes of the present invention, the term "bath ratio" is intended to mean the ratio between the total weight of composition comprising the ingredient a) or b) and the total weight of keratin fibres to be treated.

When the dyeing process is performed in one step, ingredients a) and b) are advantageously left to stand on the keratin materials for a time ranging from 1 to 90 minutes and more preferentially for a time ranging from 5 to 60 minutes, better still from 10 to 30 minutes.

When the dyeing process is performed in at least two steps, each of the ingredients a) and b) may be advantageously left to stand on the keratin materials for a time ranging from 1 to 60 minutes and more preferentially for a time ranging from 5 to 50 minutes.

On conclusion of the dyeing process according to the invention, in one or at least two steps, the keratin fibres are advantageously rinsed with water. They may optionally be washed with a shampoo, followed by rinsing with water, before being dried or left to dry.

When the dyeing process is performed in at least two steps, the keratin materials are advantageously rinsed with water between each step. In other words, the dyeing process may comprise an intermediate rinsing step between the application of the first ingredient and the application of the second ingredient. During this intermediate rinsing step, the keratin materials may optionally be washed with a shampoo, followed by rinsing with water, before being dried or left to dry.

The dyeing process according to the present invention may be performed at ambient temperature (25° C.) or with heating.

According to one particular embodiment, the process of the invention also comprises the application to said keratin materials of one or more reducing agents c), as defined previously, said reducing agent(s) c) possibly being applied before, at the same time as or after the application of the direct dye(s) a) as defined previously and/or the application of the disulfide, thiol or protected-thiol fluorescent dye(s) b) as defined previously; or alternatively, said reducing agent(s) c) is (are) present with the direct dye(s) a) as defined previously, and/or the disulfide, thiol or protected-thiol fluorescent dye(s) b) as defined previously; preferably, said reducing agent(s) are chosen from i) the reducing agents of formula (Ic) as defined previously, ii) thioglycolic acid, iii) thiolactic acid, iv) glyceryl monothioglycolate, v) cysteamine, vi) N-acetylcysteamine, vii) N-propionylcysteamine, viii) cysteine, ix) N-acetylcysteine, x) thiomalic acid, xi) pantetheine, xii) 2,3-dimercaptosuccinic acid, xiii) N-(mercaptoalkyl)-ω-hydroxyalkylamides, xiv) N-mono or N,N-dialkylmercapto-4-butyramides, xv) aminomercaptoalkylamides, xvi) N-(mercaptoalkyl)succinamic acid derivatives, xvii) N-(mercaptoalkyl)succinimide acid derivatives, xviii) alkylaminomercaptoalkylamides, ix) the azeotropic mixture of 2-hydroxypropyl thioglyconate and of (2-hydroxy-1-methyl)ethyl thioglycolate, x) mercaptoalkylaminoamides, xi) N-mercaptoalkylalkanediamides, xii) formamidine-sulfinic acid derivatives, addition salts thereof and mixtures thereof; preferably, the reducing agent(s) c) is (are) in the presence of the direct dye(s) a) as defined above, and of the disulfide, thiol or protected-thiol fluorescent dye(s) b) as defined previously, or alternatively the reducing agent(s) c) are applied at the same time as the dye(s) a) as defined previously, and of the disulfide, thiol or protected-thiol fluorescent dye(s) b) as defined previously.

When they are present, the reducing agent(s) c) may therefore be applied separately or jointly with one of the ingredients a) or b). Preferably, when they are present, the reducing agent(s) c) are applied jointly with the ingredient a) and optionally with the ingredient b).

According to one advantageous variant of the invention, the composition comprising at least one direct dye a) as defined previously and at least one reducing agent c) as defined previously is mixed with the composition comprising at least one disulfide fluorescent direct dye b) as defined previously, before the application to the keratin fibres. Preferably, the preparation is carried out from 1 second to 20 minutes before the application to said fibres, more preferentially between 10 seconds and 5 minutes before the application to said fibres.

Preferentially, the reducing agent is in a cosmetic composition comprising at least two alkaline agents different from one another; in particular, one of the alkaline agents is a bicarbonate, more particularly an ammonium bicarbonate; preferentially, the bicarbonate is in the reducing composition comprising thioglycolic acid (TGA) as reducing agent. When they are present, the oxidizing agent(s) may be applied separately or together with one of the ingredients a) or b). Preferably, when they are present, the oxidizing agent(s) are applied after application of ingredients a) and b).

According to a particular embodiment, the process for dyeing keratin fibres according to the present invention comprises the following successive steps:
  a first step of applying to said keratin materials a cosmetic composition comprising one or more direct dyes a) as defined previously, followed by
  a second step of applying to said keratin materials a cosmetic composition comprising one or more disulfide, thiol or protected-thiol fluorescent dye(s) b), as defined previously, and one or more reducing agents c), as defined previously.

According to a particular embodiment of the dyeing process of the invention, no step of said process involves an oxidizing agent.

According to another advantageous embodiment of the dyeing process of the invention, no step of said process involves a reducing agent.

The dyeing process according to the present invention may be applied to keratin materials which are wet or dry, in particular keratin fibres which are wet or dry, and preferably dry.

According to one particular embodiment of the invention, the process of the invention implements a step 1) of applying at least one activator, i.e. a reducing composition preferably comprising thioglycolic acid (TGA) as reducing agent, optionally followed by rinsing, then 2) the application of a dye composition comprising one or more disulfide, fluorescent dyes b) as defined previously and one or more direct dyes a) as defined previously, followed by a leave-on time and then rinsing, then 3) the application of a composition containing at least one oxidizing agent, preferably hydrogen peroxide $H_2O_2$ or a bromate.

According to one particular embodiment of the invention, the dyeing process of the invention is such that, taken together or separately:
  (1) the reducing composition (TGA) contains at least 2 alkaline agents different from one another, as defined previously; preferably, one of the alkaline agents is ammonium bicarbonate;
  (2) the leave-on time on the hair (of the mixture) is greater than or equal to 10 minutes;
  (3) before application of the mixture, an optional detergent pretreatment with a composition comprising at least one anionic and/or amphoteric surfactant is carried out; the clean hair may be wet or dry before application of the mixture;
  (4) optionally, the process implements a finishing step with a post-treatment using a composition comprising at least one oxidizing agent as defined previously, preferably aqueous hydrogen peroxide or a bromate derivative.

The Multi-Compartment Device

The present invention also relates to a multi-compartment device comprising a first compartment containing one or more direct dyes a), as defined previously, and a second compartment containing one or more disulfide, thiol or protected-thiol fluorescent dyes b), as defined previously, optionally a third compartment comprising one or more reducing agents c), as defined previously, and optionally another compartment comprising one or more oxidizing agents d) as defined previously, it being understood that the direct dyes a) and b) are different from one another.

The present invention also relates to a multi-compartment device comprising a first compartment containing one or more direct dyes a), as defined previously, and one or more disulfide, thiol or protected-thiol fluorescent dyes b), as defined previously, optionally a second compartment comprising one or more reducing agents c), as defined previously, and optionally another compartment comprising one or more oxidizing agents d) as defined previously, it being understood that the direct dyes a) and b) are different from one another.

Use

A subject of the present invention is also the use of one or more fluorescent direct dye(s) b), as defined previously, combined with one or more direct dye(s) a), as defined previously, that are different from b), for very chromatic, particularly visible dyeing of keratin fibres, in particular human keratin fibres such as the hair, without using an additional dye different from a) or b).

A subject of the present invention is also the use of one or more fluorescent direct dye(s) b) as defined previously, combined with one or more direct dye(s) a) as defined previously, for dyeing and/or lightening keratin fibres, in particular human keratin fibres such as the hair, with a tone depth of less than 6, preferably less than or equal to 4, without using an additional dye different from a) or b).

The examples that follow serve to illustrate the invention without, however, being limiting in nature.

EXAMPLES

In the examples that follow, all the amounts are given as weight percentages relative to the total weight of the composition, unless otherwise indicated.

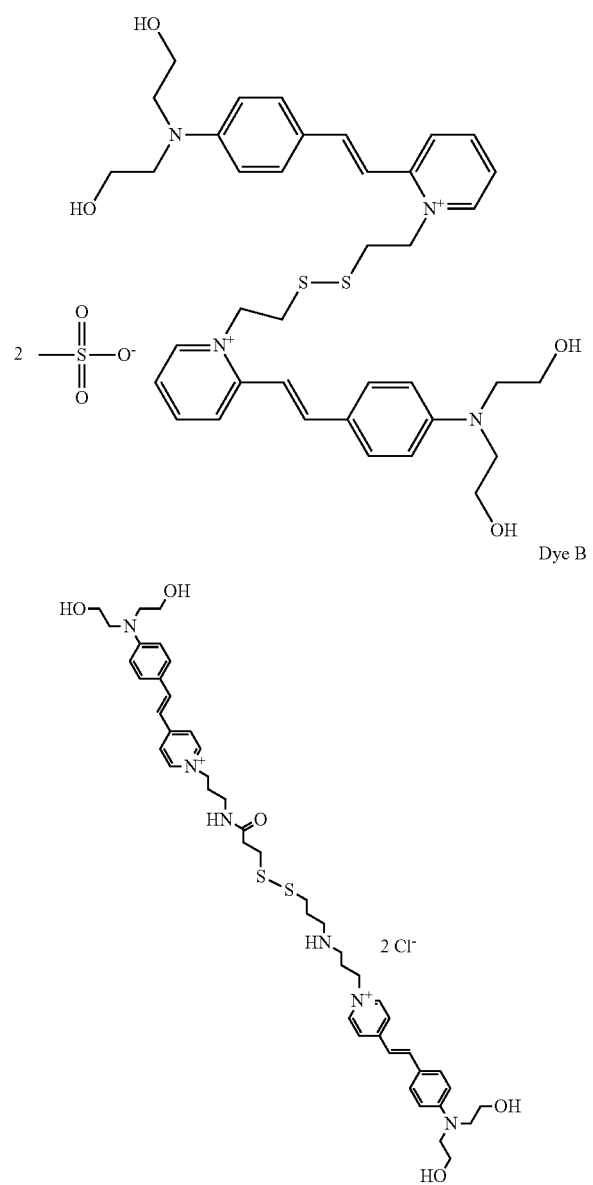

Dye A

Dye B

The following compositions were prepared, the amounts are expressed in % by weight.

| Ingredients | A1 (invention) | B1 (comparative) | A2 (invention) | B2 (comparative) |
|---|---|---|---|---|
| Basic Orange 31 (BO31) | 0.01 | 0.2 | — | — |
| Disulfide dye A | 0.19 | — | — | — |
| Basic Red 51 (BR51) | — | — | 0.01 | 0.3 |
| Disulfide dye B | — | — | 0.29 | — |
| Cetrimonium chloride | 0.02 | 0.02 | 0.02 | 0.02 |
| Behentrimonium chloride | 2.05 | 2.05 | 2.05 | 2.05 |
| Cetyl alcohol | 1 | 1 | 1 | 1 |
| Hydroxypropyltrimonium guar chloride | 0.1 | 0.1 | 0.1 | 0.1 |
| Isopropyl alcohol or isopropanol | 0.5 | 0.5 | 0.5 | 0.5 |
| Cetearyl alcohol | 3.75 | 3.75 | 3.75 | 3.75 |
| Amodimethicone | 1.15 | 1.15 | 1.15 | 1.15 |
| Hydroxyethylcelluose | 0.2 | 0.2 | 0.2 | 0.2 |
| Trideceth-6 | 0.1 | 0.1 | 0.1 | 0.1 |
| Preservatives | qs | qs | qs | qs |
| pH agent | qs pH = 3.5 | qs pH = 3.5 | qs pH = 3.5 | qs pH = 3.5 |
| Water | qs 100 | qs 100 | qs 100 | qs 100 |

The compositions above were applied to locks of light (bleached) hair at a rate of 5 g of composition per 1 g of lock.

After a leave-on time of 10 min on a thermostated plate at 27° C., the hair is rinsed and dried.

Spectrocolorimetric Results

The colour of the locks was evaluated in the L*a*b* system, using a Minolta® CM 3600D spectrocolorimeter, (Illuminant D65).

In this L*a*b* system, L* represents the lightness, a* indicates the green/red colour axis and b* indicates the blue/yellow colour axis. The higher the value of L, the lighter or less intense the colour. Conversely, the lower the value of L, the darker or more intense the colour. The higher the value of a*, the redder the shade, and the higher the value of b*, the yellower the shade.

The chromaticity is calculated according to the following formula:

$$C^* = \sqrt{(a^*)^2 + (b^*)^2}$$

The higher the value of the chromaticity C*, the more chromatic the colour of the treated keratin fibres.

| Composition | a* | b* | C* |
|---|---|---|---|
| A1 (invention) | 52.04 | 53.66 | 74.76 |
| A2 (comparative) | 49.26 | 34.29 | 60.02 |
| B1 (invention) | 50.22 | 33.94 | 60.62 |
| B2 (comparative) | 37.69 | 14.61 | 40.42 |

The compositions according to the invention A1 and A2 comprising the direct dye+disulfide dye combination produce values of C* which are higher, and therefore at a significantly greater chromaticity, compared with the comparative compositions B1 and B2, respectively comprising only the direct dyes.

Fastness with respect to washing: the locks treated with the compositions A1 and A2 were then subjected to a challenge of 5 successive shampooing operations (shp). The fastness with respect to washing is represented by the colour difference ΔE between the locks dyed before and then after the 5-shampooing-operation challenge, according to the following equation:

$$\Delta E = \sqrt{(L^* - L_o^*)^2 + (a^* - a_o^*)^2 + (b^* - b_o^*)^2}$$

In this equation, $L^*$, $a^*$ and $b^*$ represent the values measured after shampooing challenge on the dyed locks, and $L_o^*$, $a_o^*$ and $b_o^*$ represent the values measured before shampooing challenge on the dyed locks.

The lower the ΔE value, the better the colour-fastness of the hair with respect to washing.

| Method | $L^*$ | $a^*$ | $b^*$ | ΔE |
|---|---|---|---|---|
| A1 before shp | 49.25 | 52.04 | 53.66 | — |
| A1 after shp | 54.28 | 47.16 | 60.35 | 9.69 |
| A2 before shp | 36.80 | 49.26 | 34.29 | — |
| A2 after shp | 46.02 | 48.56 | 43.11 | 12.78 |

The composition A1 according to the invention exhibits a lower ΔE value, and therefore better fastness with respect to washing, compared with the comparative composition.

Other Examples

The amounts of the compositions in the tables below are indicated by weight of active material (g per 100 g unless otherwise mentioned).

| | | HC Blue 15 | | Acid dye | |
|---|---|---|---|---|---|
| Ingredients | | A3 (invention) | B3 (comparative) | A4 (invention) | B4 (comparative) |
| HC Blue 15 (structure shown) | | 0.01 | 0.2 | — | — |
| Acid Red 52 (structure shown) | | — | — | 0.01 | 0.3 |
| Dye A | | 0.19 | — | — | — |
| Dye B | | — | — | 0.29 | — |
| Behentrimonium chloride | | 2.05 | 2.05 | 2.05 | 2.05 |
| Isopropylic alcohol or isopropanol | | 0.5 | 0.5 | 0.5 | 0.5 |
| Cetyl alcohol | | 1 | 1 | 1 | 1 |
| Hydroxy-propyltrimonium chloride guar | | 0.1 | 0.1 | 0.1 | 0.1 |
| Cetearyl alcohol | | 3.75 | 3.75 | 3.75 | 3.75 |
| Amodimehicone | | 1.15 | 1.15 | 1.15 | 1.15 |
| Trideceth-6 | | 0.1 | 0.1 | 0.1 | 0.1 |

-continued

| | HC Blue 15 | | Acid dye | |
| Ingredients | A3 (invention) | B3 (comparative) | A4 (invention) | B4 (comparative) |
|---|---|---|---|---|
| Cetrimonium chloride | 0.02 | 0.02 | 0.02 | 0.02 |
| Hydroxyéthylcelluose | 0.2 | 0.2 | 0.2 | 0.2 |
| Preservatives | Qs | Qs | Qs | Qs |
| Alkaline agent (NaOH) | Qs pH = 3.5 | Qs pH = 3.5 | Qs pH = 3.5 | Qs pH = 3.5 |
| Water | Qs 100 | Qs 100 | Qs 100 | Qs 100 |

The compositions above were applied to locks of light (bleached) hair at a rate of 5 g of composition per 1 g of lock.

After a leave-on time of 10 min on a thermostated plate at 27° C., the hair is rinsed and dried.

Spectrocolorimetric Results

The colour of the locks was evaluated in the L*a*b* system, using a Minolta® CM 3600D spectrocolorimeter, (Illuminant D65).

| Composition | a* | b* | C* |
|---|---|---|---|
| A3 (invention) | 19.88 | 29.36 | 35.46 |
| B3 (comparative) | 2.79 | −32.69 | 32.81 |
| A4 (invention) | 60.24 | 47.95 | 76.99 |
| B4 (comparative) | 11.81 | 28.75 | 31.08 |

The compositions according to the invention A3 and A4 comprising the direct dye+disulfide dye combination produce values of C* which are higher, and therefore at a significantly greater chromaticity, compared with the comparative compositions B3 and B4, respectively comprising only the direct dyes.

The invention claimed is:

1. A process for dyeing keratin fibers, comprising applying to the keratin fibers:
   a) at least one direct dye; and
   b) at least one disulfide, thiol, or protected-thiol direct fluorescent dyes;
   wherein
   the at least one direct dye and the at least one disulfide, thiol, or protected-thiol fluorescent dyes are applied to the keratin fibers jointly in the same composition or separate compositions, or sequentially in separate compositions, and
   the at least one direct dye is different from the at least one disulfide, thiol, or protected-thiol direct fluorescent dye; and
   the at least one direct dye is comprised in a cosmetic composition, and is present in a total amount ranging from 0.0001% to 30%, relative to the total weight of the cosmetic composition in which it is present.

2. The process according to claim 1, wherein the at least one direct dye a) is ionic or zwitterionic.

3. The process according to claim 1, wherein the at least one direct dye is chosen from acridines; acridones; anthranthrones; anthrapyrimidines; anthraquinones; azines; (poly)azos, hydrazonos or hydrazones; azomethines; benzanthrones; benzimidazoles; benzimidazolones; benzindoles; benzoxazoles; benzopyrans; benzothiazoles; benzoquinones; bisazines; bis-isoindolines; carboxanilides; coumarins; cyanines; diazines; diketopyrrolopyrroles; dioxazines; diphenylamines; diphenylmethanes; dithiazines; flavonoids; fluorindines; formazans; indamines; indanthrones; indigoids; pseudoindigoids; indophenols; indoanilines; isoindolines; isoindolinones; isoviolanthrones; lactones; (poly)methines; naphthalimides; naphthanilides; naphtholactams; naphthoquinones; nitros; oxadiazoles; oxazines; perilones; perinones; perylenes; phenazines; phenoxazines; phenothiazines; phthalocyanines; polyenes/carotenoids; porphyrins; pyranthrones; pyrazolanthrones; pyrazolones; pyrimidinoanthrones; pyronines; quinacridones; quinolines; quinophthalones; squaranes; tetrazoliums; thiazines; thioindigos; thiopyronines; triarylmethanes; xanthenes; or combinations thereof.

4. The process according to claim 1, wherein the at least one direct dye is chosen from the following direct dyes:
   the hydrazono cationic dyes of formulae (II) and (III) below, the azo dyes of formulae (IV) and (V) below, or optical and geometric isomers thereof and tautomers thereof, salts of organic or mineral acids or bases thereof, solvates thereof, or combinations thereof:

$$\text{Het}^+ - C(R_a) = N - N(R_b) - Ar, Q^- \tag{II}$$

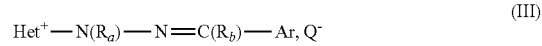

$$\text{Het}^+ - N(R_a) - N = C(R_b) - Ar, Q^- \tag{III}$$

$$\text{Het}^+ - N = N - Ar, Q^- \tag{IV}$$

$$Ar^+ - N = N - Ar'', Q^- \tag{V}$$

wherein:
  Het+ represents a cationic heteroaryl radical which is optionally substituted;
  Ar+ represents an aryl radical having an exocyclic cationic charge;
  Ar represents an aryl group which is optionally substituted;
  Ar" represents an optionally substituted (hetero)aryl group;
  $R_a$ and $R_b$, which may be identical or different, represent a hydrogen atom or a ($C_1$-$C_8$)alkyl group, which is optionally substituted;
  or Ra with a substituent of Het+ or Rb with a substituent of Ar form, together with the atoms that bear them, a (hetero)cycloalkyl; and
  Q⁻ represents an organic or mineral anionic counterion; and
anionic, cationic or zwitterionic chosen from those of formula (I):

(I)

or organic or mineral acid or base addition salts thereof, geometrical isomers, optical isomers or tautomers thereof, or the mesomeric forms thereof, or solvates; wherein:

A, B and C, which may be identical or different, represent a (hetero)aryl group which is optionally substituted, and ---- represents a single bond or double bond.

5. The process according to claim 1, wherein the at least one direct dye is chosen from anionic dyes selected from those of formulae (VII), (VII'), (VIII), (VIII'), (IX), (IX'), (X), (X'), (XI), (XII), (XII'), (XIII), and (XIV) below:

c3a) the diaryl anionic azo dyes of formula (VII) or (VII'):

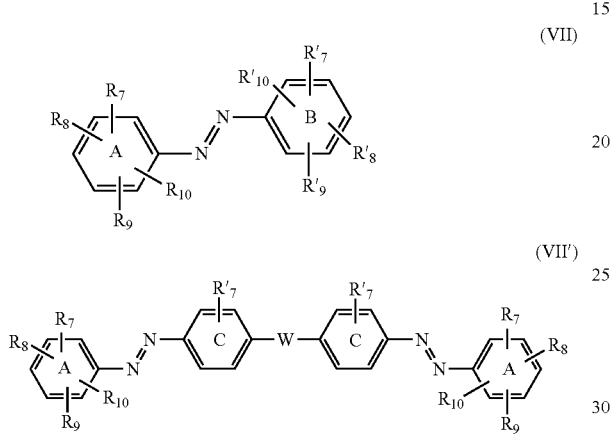

wherein:

$R_7$, $R_8$, $R_9$, $R_{10}$, $R'_7$, $R'_8$, $R'_9$, and $R'_{10}$, which may be identical or different, represent a hydrogen atom or a group chosen from: i) alkyl, ii) alkoxy, iii) alkylthio, iv) hydroxyl, v) mercapto, vi) nitro, vii) $R^o$—C(X)—X'—, $R^o$—X'—C(X)—, $R^o$—X'—C(X)—X"—, wherein $R^o$ represents a hydrogen atom or an alkyl or aryl group; wherein X, X' and X", which may be identical or different, represent an oxygen or sulfur atom or NR with R representing a hydrogen atom or an alkyl group; viii) $(O)_2S(O^-)$—, $M^+$ wherein $M^+$ represents a cationic counterion; ix) (O)CO$^-$—, $M^+$, wherein $M^+$ represents an organic or mineral cationic counterion; xi) R'''—S$(O)_2$—X'— wherein R''' represents an optionally substituted alkyl or aryl group, X' as defined previously; xii) (di)(alkyl)amino; xiii) aryl(alkyl)amino optionally substituted with one or more groups chosen from nitro; nitroso; $(O)_2S(O^-)$—; xiv) optionally substituted heteroaryl; xv) cycloalkyl; xvi) Ar—N=N— wherein Ar represents an optionally substituted aryl group;

or alternatively two contiguous groups $R_7$ with $R_8$ or $R_8$ with $R_9$ or $R_9$ with $R_{10}$ which together form a fused benzo group A'; and $R'_7$ with $R'_8$ or $R'_8$ with $R'_9$ or $R'_9$ with $R'_{10}$ which together form a fused benzo group B'; with A' and B' optionally substituted with one or more groups chosen from i) nitro; ii) nitroso; iii) $(O)_2S(O^-)$—, $M^+$; iv) hydroxyl; v) mercapto; vi) (di)(alkyl)amino; vii) $R^o$—C(X)—X'—; viii) $R^o$—X'—C(X)—; ix) $R^o$—X'—C(X)—X"—; x) Ar—N=N— and xi) optionally substituted aryl(alkyl)amino; with $M^+R^o$, X, X', X" and Ar as defined previously;

W represents a sigma bond σ, an oxygen or sulfur atom, or a divalent radical i)—N(R)— with R as defined previously, or ii) methylene —C(R$_a$)(R$_b$)— with R$_a$ and R$_b$, which may be identical or different, representing a hydrogen atom or an aryl group, or alternatively R$_a$ and R$_b$ form, together with the carbon atom that bears them, a spiro cycloalkyl;

wherein formulae (VII) and (VII') comprise at least one sulfonate $(O)_2S(O^-)$—, $Q^+$or carboxylate $(O)C(O^-)$—, $Q^+$ radical on one of the rings A, or A', B, B' or C with $R_1R_2R_3R_4$ as defined previously; $Q^+$ represents an organic or mineral cationic counterion$^+$;

c3b) the pyrazolone anionic azo dyes of formulae (VIII) and (VIII'):

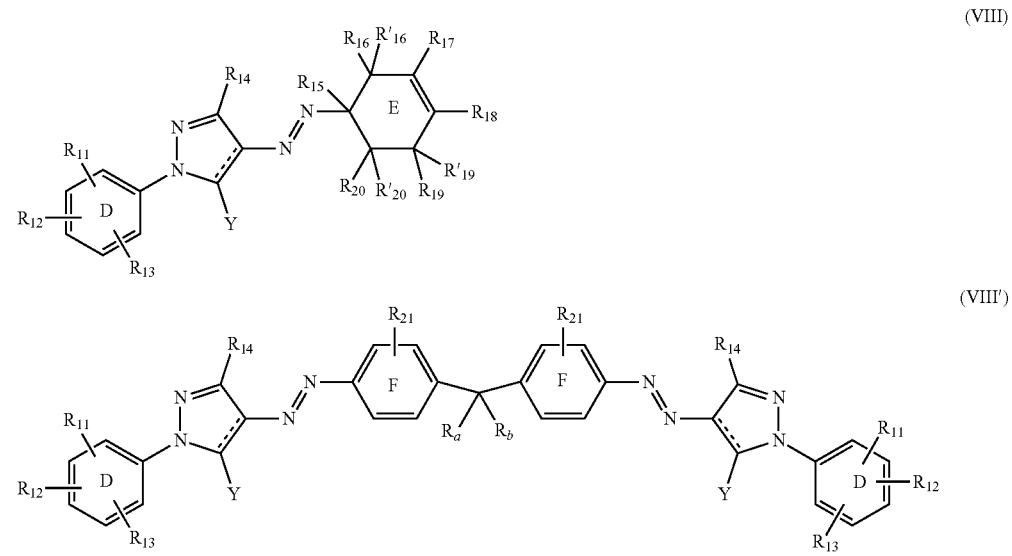

wherein:

$R_{11}$, $R_{12}$ and $R_{13}$, which may be identical or different, represent a hydrogen or halogen atom, an alkyl group or —$(O)_2S(O^-)$, $M^+$ with $M^+$ as defined previously;

$R_{14}$ represents a hydrogen atom, an alkyl group or a group —C(O)O—, $M^+$ with $M^+$ as defined previously;

$R_{15}$ represents a hydrogen atom;

$R_{16}$ represents an oxo group, wherein $R'_{16}$ is absent, or alternatively $R_{15}$ with $R_{16}$ together form a double bond;

$R_{17}$ and $R_{18}$, which may be identical or different, represent a hydrogen atom or a group chosen from:
(O)$_2$S(O$^-$)—, M$^+$ with M$^+$ as defined previously;
Ar—O—S(O)$_2$— wherein Ar represents an optionally substituted aryl group;

$R_{19}$ and $R_{20}$ together form either a double bond, or a benzo group D', which is optionally substituted;

$R'_{16}$, $R'_{19}$ and $R'_{20}$, which may be identical or different, represent a hydrogen atom or an alkyl or hydroxyl group;

$R_{21}$ represents a hydrogen atom or an alkyl or alkoxy group;

$R_a$ and $R_b$, which may be identical or different, are as defined previously;

Y represents a hydroxyl group or an oxo group;

- - - represents a single bond when Y is an oxo group; and represents a double bond when Y represents a hydroxyl group;

wherein formulae (VIII) and (VIII') comprise at least one sulfonate group (O)$_2$S(O$^-$)—, Q$^+$ on one of the rings D or E or formulae (VIII) and (VIII') comprise at least one carboxylate group (O)C(O$^-$)—, Q$^+$ with Q$^+$ as defined previously;

c3c) the anthraquinone dyes of formulae (IX) and (IX'):

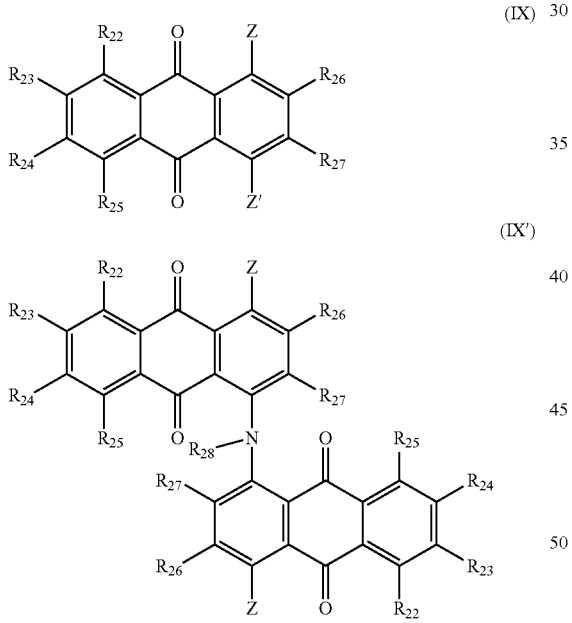

wherein:
$R_{22}$, $R_{23}$, $R_{24}$, $R_{25}$, $R_{26}$ and $R_{27}$, which may be identical or different, represent a hydrogen or halogen atom or a group chosen from i) alkyl, ii) hydroxyl, iii) mercapto, iv) alkoxy, v) alkylthio, vi) aryloxy or arylthio, which is optionally substituted, vii) aryl(alkyl)amino optionally substituted with one or more groups chosen from alkyl and (O)$_2$S(O$^-$)—, viii) (di)(alkyl)amino, ix) (di)(hydroxyalkyl)amino, x) (O)$_2$S(O$^-$)—;

Z' represents a hydrogen atom or a group NR$_{28}$R$_{29}$ wherein R$_{28}$ and R$_{29}$, which may be identical or different, represent a hydrogen atom or a group chosen from i) alkyl, ii) polyhydroxyalkyl, iii) aryl optionally substituted with one or more groups; R$^o$—C(X)—X'—, R$^o$—X'—C(X)—, R$^o$—X'—C(X)—X''—, iv) cycloalkyl;

Z represents a group chosen from hydroxyl and NR'$_{28}$R'$_{29}$ wherein R'$_{28}$ and R'$_{29}$, which may be identical or different, represent the same atoms or groups as R$_{28}$ and R$_{29}$;

wherein formulae (IX) and (IX') comprise at least one sulfonate group (O)$_2$S(O$^-$)—, Q$^+$;

c3d) the nitro dyes of formulae (X) and (X'):

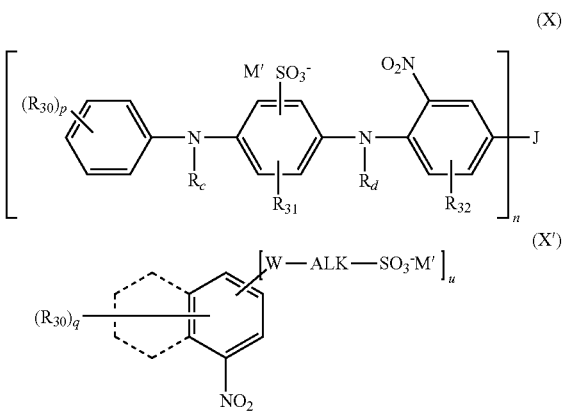

wherein:
$R_{30}$, $R_{31}$ and $R_{32}$, which may be identical or different, represent a hydrogen or halogen atom or a group chosen from i) alkyl, ii) alkoxy optionally substituted with one or more hydroxyl groups, iii) alkylthio optionally substituted with one or more hydroxyl groups, iv) hydroxyl or mercapto, v) nitro or nitroso, vi) (poly)haloalkyl, vii) R$^o$—C(X)—X'—, R$^o$—X'—C(X)—, R$^o$—X'—C(X)—X''— with R$^o$; X, X' and X'' as defined previously, viii) (O)$_2$S(O$^-$)—, ix) (O)CO$^-$—, x) (di)(alkyl)amino, xi) (di)(hydroxyalkyl)amino, xii) heterocycloalkyl; wherein R$_{30}$, R$_{31}$ and R$_{32}$ represent a hydrogen atom;

R$_c$ and R$_d$, which may be identical or different, represent a hydrogen atom or an alkyl group;

W is as defined previously;

ALK represents a linear or branched divalent $C_1$-$C_6$ alkylene group;

n is 1 or 2;

p represents an integer between 1 and 5 inclusive;

q represents an integer between 1 and 4 inclusive;

u is 0 or 1;

when n is 1, J represents a nitro or nitroso group;

when n is 2, J represents an oxygen or sulfur atom, or a divalent radical —S(O)m— wherein m represents an integer 1 or 2;

M' is as defined previously for M$^+$;

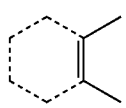

which may be present or absent, represents a benzo group optionally substituted with one or more groups R$_{30}$;

wherein formulae (X) and (X') comprise at least one sulfonate group (O)$_2$S(O$^-$)—, Q$^+$ or carboxylate group (O)C(O$^-$)—, Q$^+$;

c3e) the triarylmethane dyes of formula (XI):

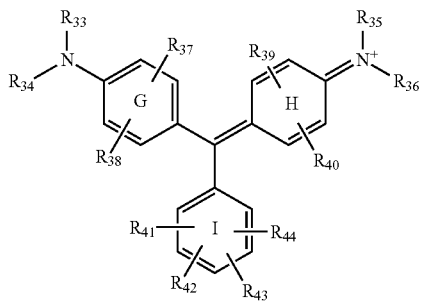

(XI)

wherein:
- $R_{33}$, $R_{34}$, $R_{35}$ and $R_{36}$, which may be identical or different, represent a hydrogen atom or a group chosen from alkyl, optionally substituted aryl or optionally substituted arylalkyl;
- $R_{37}$, $R_{38}$, $R_{39}$, $R_{40}$, $R_{41}$, $R_{42}$, $R_{43}$ and $R_{44}$, which may be identical or different, represent a hydrogen atom or a group chosen from: i) alkyl; ii) alkoxy, alkylthio; iii) (di)(alkyl)amino; iv) hydroxyl or mercapto; v) nitro or nitroso; vii) $R°$—C(X)—X'—, $R°$—X'—C(X)—, $R°$—X'—C(X)—X"— wherein $R°$ represents a hydrogen atom or an alkyl or aryl group; wherein X, X' and X", which may be identical or different, represent an oxygen or sulfur atom or NR wherein R represents a hydrogen atom or an alkyl group; viii) $(O)_2S(O^-)$—, $M^+$ wherein $M^+$ represents a hydrogen atom or a cationic counterion; ix) O)CO^-—, $M^+$ with $M^+$ as defined previously;
- or alternatively two contiguous groups $R_{41}$ with $R_{42}$ or $R_{42}$ with $R_{43}$ or $R_{43}$ with $R_{44}$ which together form a fused benzo group: I'; with I' optionally substituted with one or more groups chosen from i) nitro; ii) nitroso; iii) $(O)_2S(O^-)$—, $M^+$; iv) hydroxyl; v) mercapto; vi) (di)(alkyl)amino; vii) $R°$—C(X)—X'—; viii) $R°$—X'—C(X)—; and ix) $R°$—X'—C(X)—X"—;
- wherein at least one of the rings G, H, I or I' comprises at least one sulfonate $(O)_2S(O^-)$—, $Q^+$ or carboxylate $(O)C(O^-)$—;

c3f) the xanthene-based dyes of formula (XII) or (XII'):

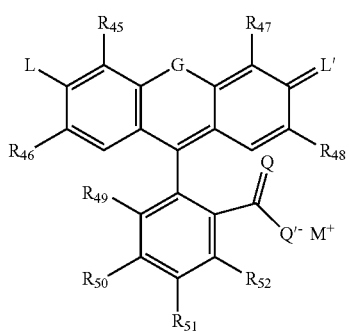

(XII)

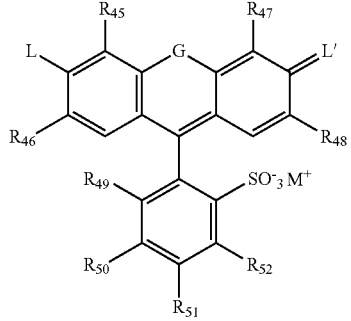

(XII')

- $R_{45}$, $R_{46}$, $R_{47}$ and $R_{48}$, which may be identical or different, represent a hydrogen or halogen atom;
- $R_{49}$, $R_{50}$, $R_{51}$ and $R_{52}$, which may be identical or different, represent a hydrogen or halogen atom or a group chosen from i) alkyl; ii) alkoxy, alkylthio; iii) hydroxyl, mercapto; iv) nitro, nitroso; v) $(O)_2S(O^-)$—, $M^+$ wherein $M^+$ represents a hydrogen atom or a cationic counterion; or vi) (O)CO^-—;
- G represents an oxygen or sulfur atom or a group $NR_e$;
- L represents an alkoxide $O^-$, $M^+$; a thioalkoxide $S^-$, $M^+$ or a group $NR_f$, with $R_f$ representing a hydrogen atom or an alkyl group;
- L' represents an oxygen or sulfur atom or an ammonium group: $N^+R_fR_g$, with $R_f$ and $R_g$, which may be identical or different, representing a hydrogen atom, an alkyl group or optionally substituted aryl; and
- Q and Q', which may be identical or different, represent an oxygen or sulfur atom;
- wherein formula (XII) comprises at least one sulfonate group $(O)_2S(O^-)$—, $Q^+$ or carboxylate group $(O)C(O^-)$—;

c3g) the indigoid dyes of formula (XIII):

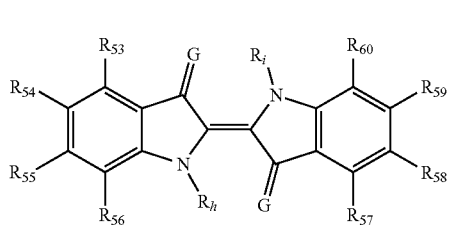

(XIII)

wherein:
- $R_{53}$, $R_{54}$, $R_{55}$, $R_{56}$, $R_{57}$, $R_{58}$, $R_{59}$ and $R_{60}$, which may be identical or different, represent a hydrogen atom or a group chosen from: i) alkyl; ii) alkoxy, alkylthio; iii) hydroxyl or mercapto; iv) nitro or nitroso; v) $R°$—C(X)—X'—, $R°$—X'—C(X)—, $R°$—X'—C(X)—X"— with $R°$ representing a hydrogen atom or an alkyl or aryl group; X, X' and X", which may be identical or different, representing an oxygen or sulfur atom or NR with R representing a hydrogen atom or an alkyl group; vi) $(O)_2S(O^-)$—, $M^+$ with $M^+$ as defined previously; vii) (O)CO—, M+ with M+ as defined previously;
- G represents an oxygen or sulfur atom or a group $NR_e$ with $R_e$ as defined previously;
- $R_i$ and $R_h$, which may be identical or different, represent a hydrogen atom or an alkyl group;

wherein formula (XIII) comprises at least one sulfonate group (O)$_2$S(O$^-$)—, Q$^+$ or carboxylate group (O)C(O$^-$)—, Q$^+$ with Q$^+$ as defined previously;

c3h) the quinoline-based dyes of formula (XIV):

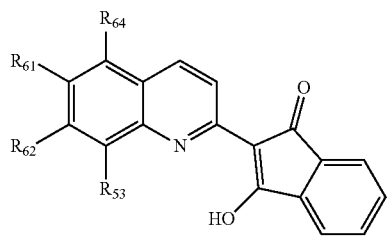

(XIV)

wherein:
$R_{61}$ represents a hydrogen or halogen atom or an alkyl group;
$R_{62}$, $R_{63}$ and $R_{64}$, which may be identical or different, represent a hydrogen atom or a group (O)$_2$S(O$^-$)—, M$^+$ with M$^+$ as defined previously;
or alternatively $R_{61}$ with $R_{62}$, or $R_{61}$ with $R_{64}$, together form a benzo group optionally substituted with one or more groups (O)$_2$S(O$^-$)—, M$^+$ with M$^+$ representing a hydrogen atom or a cationic counterion;
wherein formula (IX) comprises at least one sulfonate group (O)$_2$S(O—)-, Q$^+$ with Q$^+$ as defined previously.

6. The process according to claim 1, wherein the at least one direct dye is not a direct dye bearing at least one disulfide function, is not a direct dye bearing at least one thiol function, and is not a direct dye bearing at least one protected-thiol function.

7. The process according to claim 1, wherein the at least one disulfide, thiol or protected-thiol dye is chosen from dyes which absorb light in the yellow, orange, and red range.

8. The process according to claim 1, wherein the at least one disulfide, thiol or protected-thiol fluorescent dye is chosen from those of formula (Ib): A-(X)$_p$—C$_{sat}$—S—U, organic or mineral acid or base salts thereof, optical or geometric isomers or tautomers thereof, or solvates thereof,
wherein:
U represents a radical chosen from:
   a) —S—C'$_{sat}$—(X)$_p$'-A'; and
   b) —Y;
A and A', which may be identical or different, represent a radical containing at least one quaternized cationic fluorescent chromophore or at least one fluorescent chromophore bearing a quaternized or quaternizable cationic group;
Y represents i) a hydrogen atom, or ii) a thiol-function-protecting group;
X and X', which may be identical or different, represent a linear or branched, saturated or unsaturated divalent C$_1$-C$_{30}$ hydrocarbon-based chain, optionally interrupted and/or optionally terminated at one or both of its ends with one or more divalent groups or combinations thereof chosen from:
   —N(R)—, —N$^+$(R)(R)—, —O—, —S—, —C(O)—, —S(O)— and —SO$_2$—, with R, which may be identical or different, chosen from a hydrogen and a C$_1$-C$_4$ alkyl, hydroxyalkyl, or aminoalkyl radical;
an aromatic or non-aromatic, saturated or unsaturated, fused or non-fused (hetero)cyclic radical optionally comprising one or more identical or different, optionally substituted heteroatoms;
p and p', which may be identical or different, are equal to 0 or 1;
C$_{sat}$ and C'$_{sat}$, which may be identical or different, represent an optionally substituted linear or branched, or cyclic, C$_1$-C$_{18}$ alkylene chain.

9. The process according to claim 1, wherein the at least one disulfide, thiol or protected-thiol fluorescent dye is chosen from the dyes having the following chemical structures:

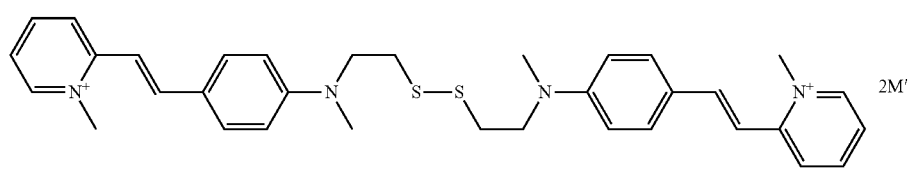

8

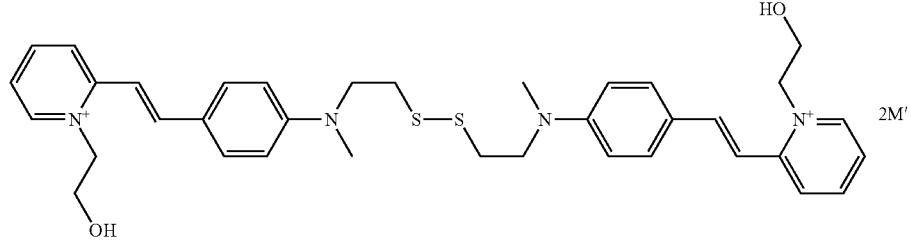

9

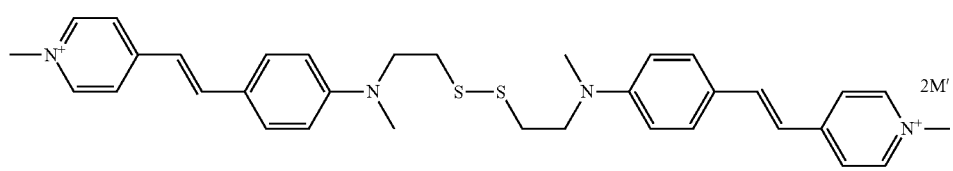

10

-continued
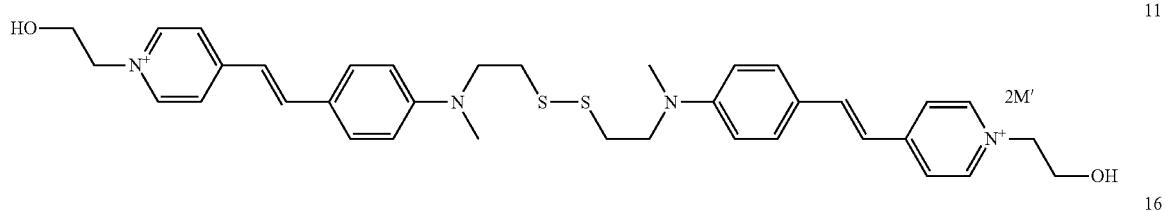
11
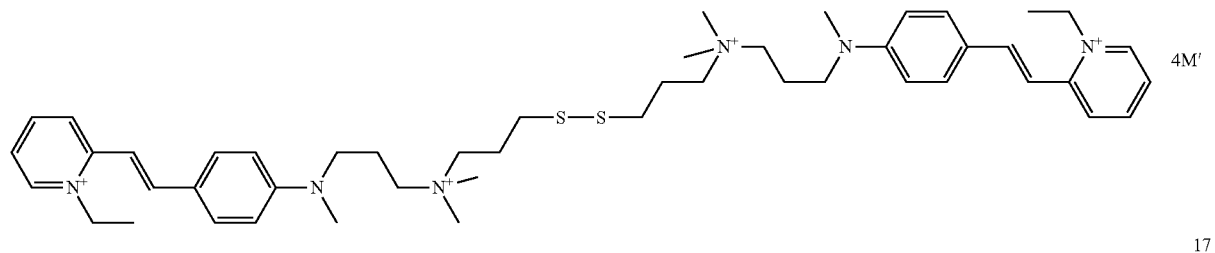
16
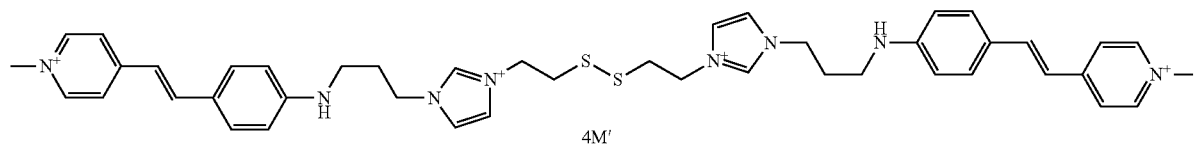
17
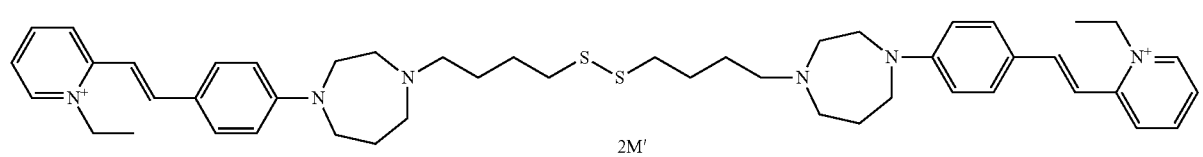
18
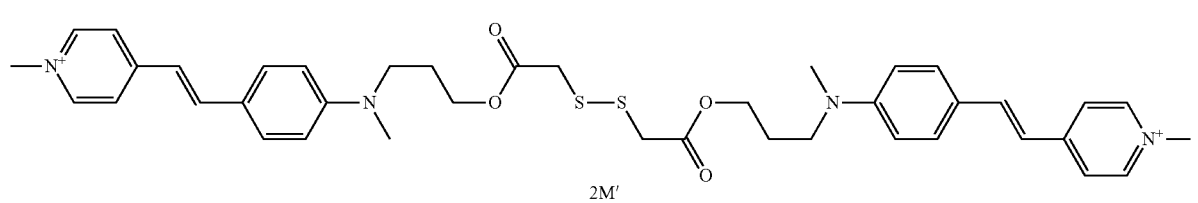
20
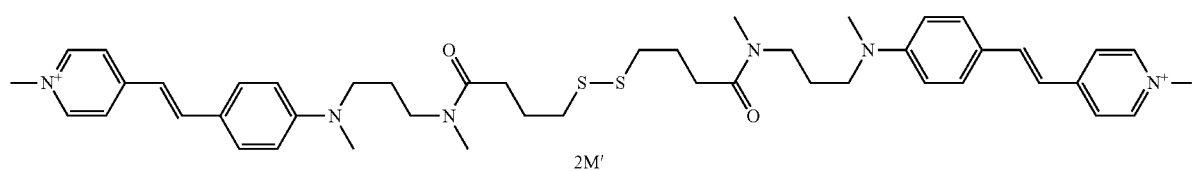
21
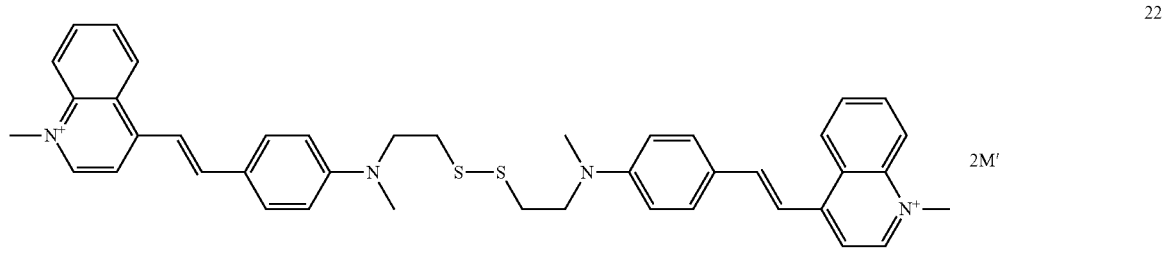
22
23

-continued
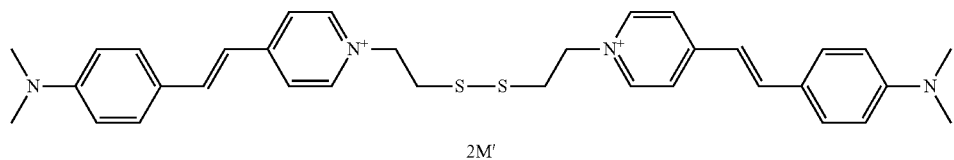
24
2M'
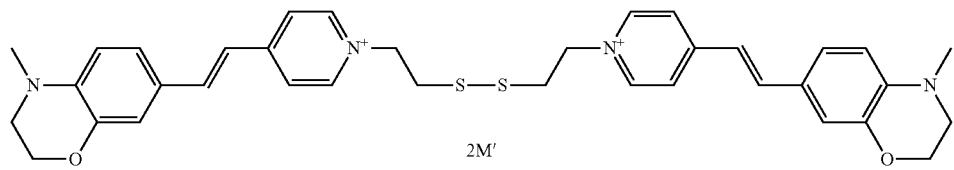
25
2M'
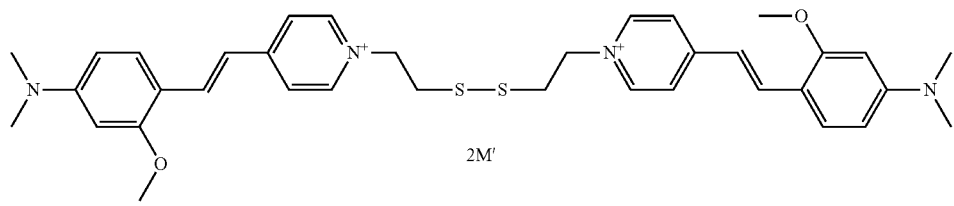
26
2M'
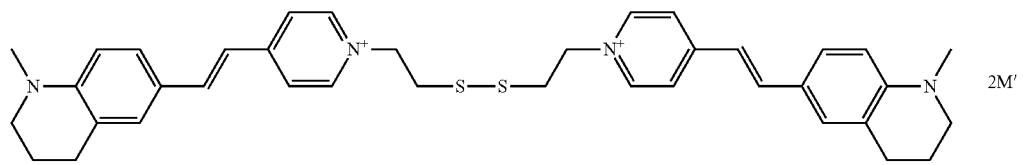
27
2M'
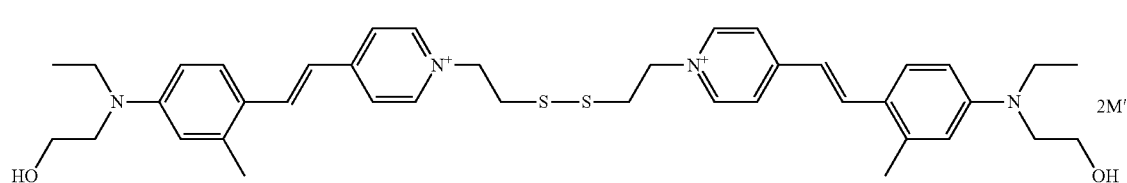
28
2M'
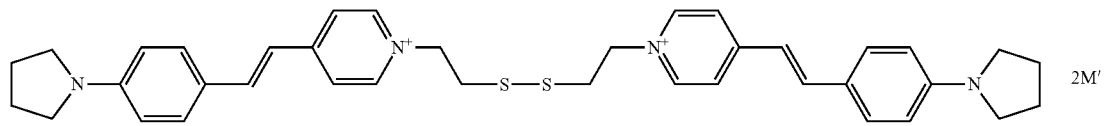
29
2M'
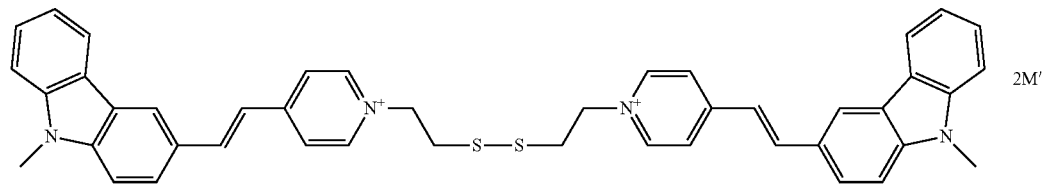
30
2M'
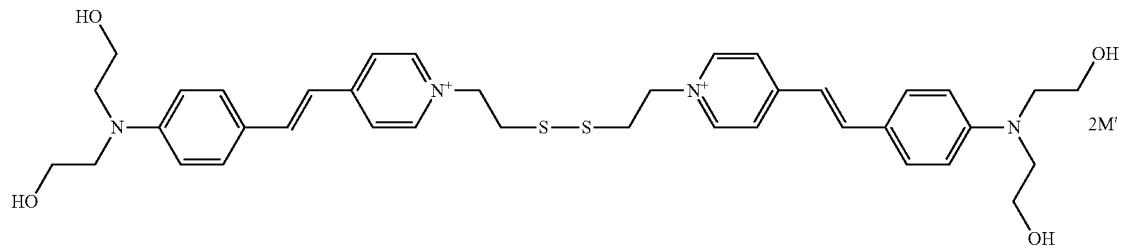
31
2M'

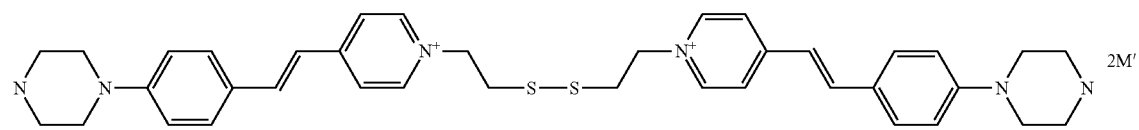
32 2M′
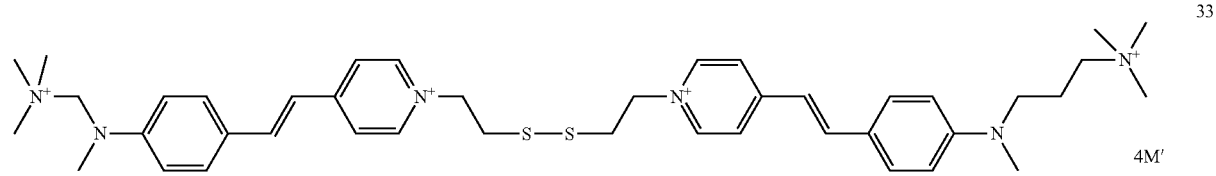
33 4M′
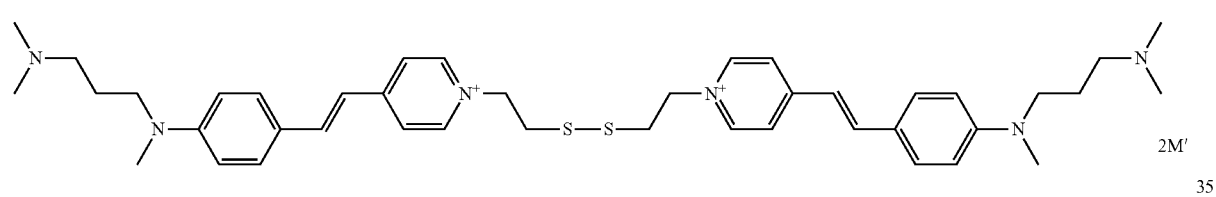
34 2M′
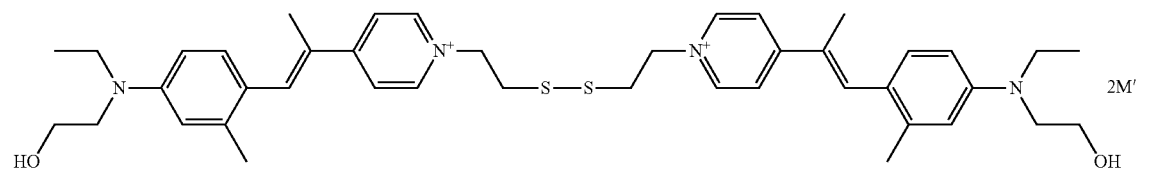
35 2M′
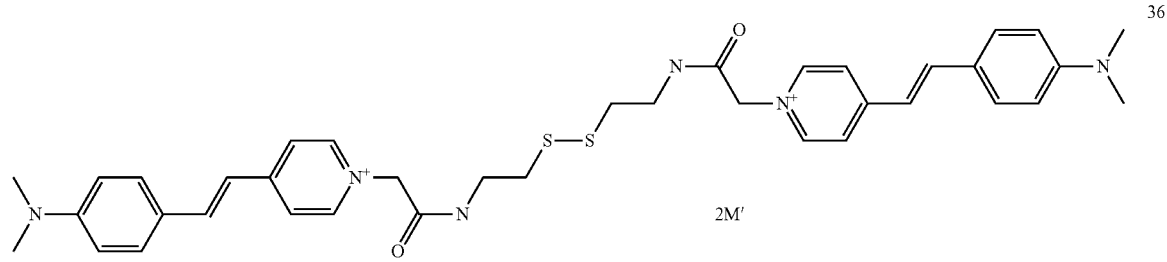
36 2M′
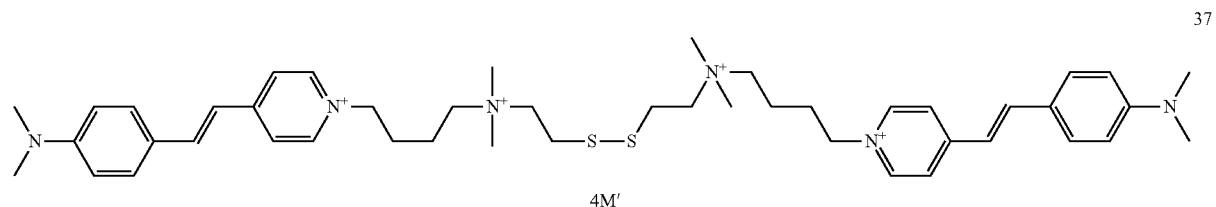
37 4M′
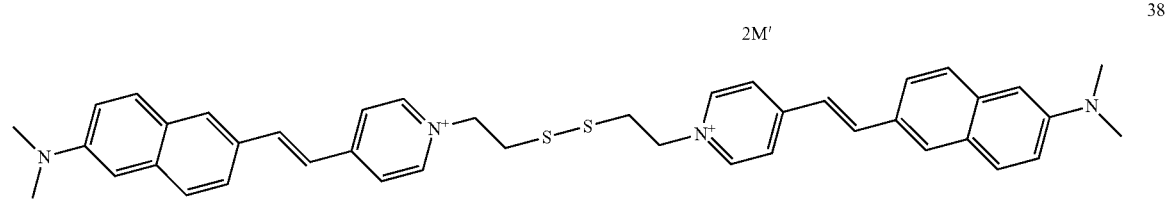
38 2M′

-continued
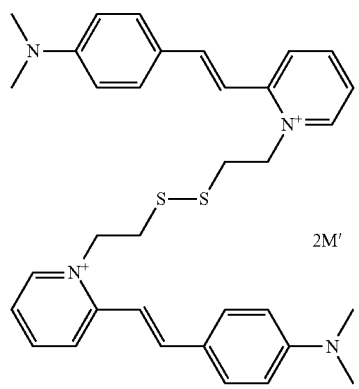
39
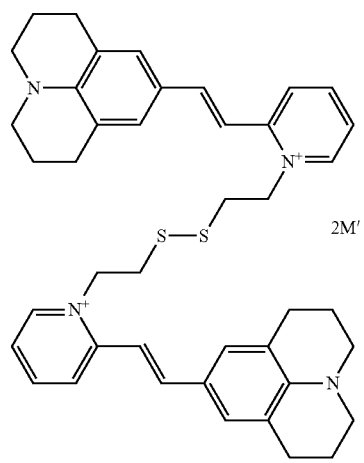
40
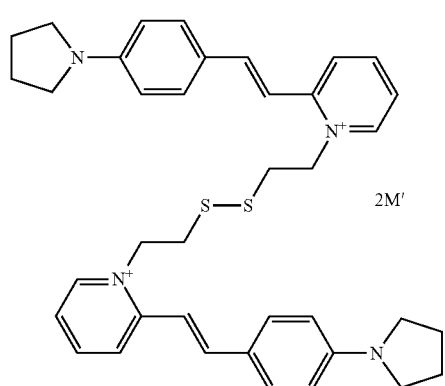
41
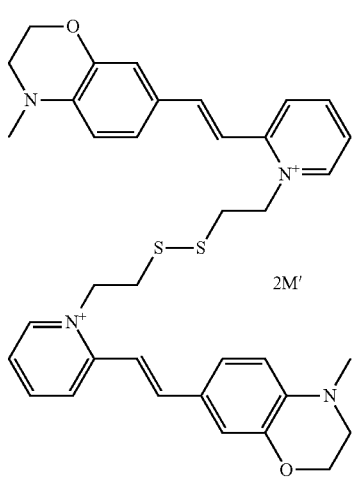
42
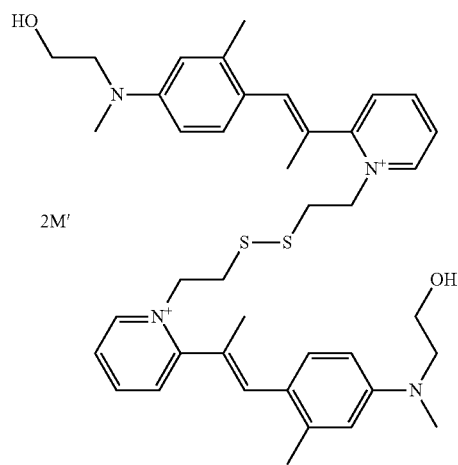
43
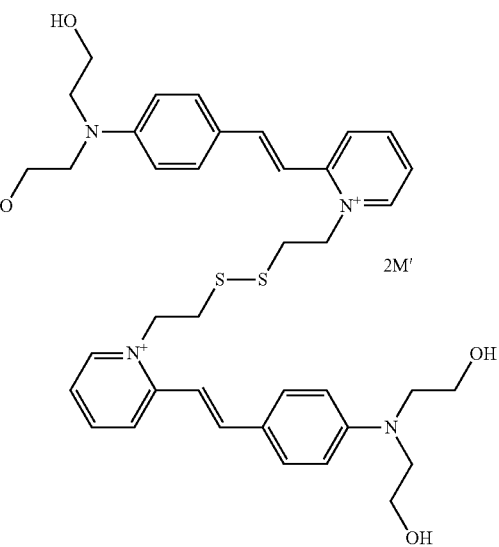
44

45
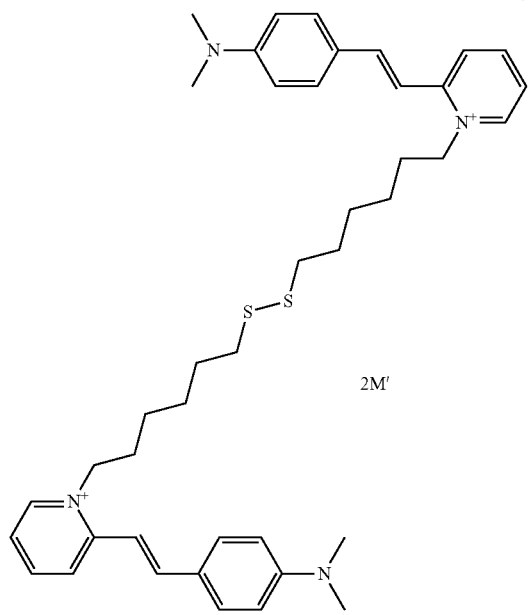
2M′
46
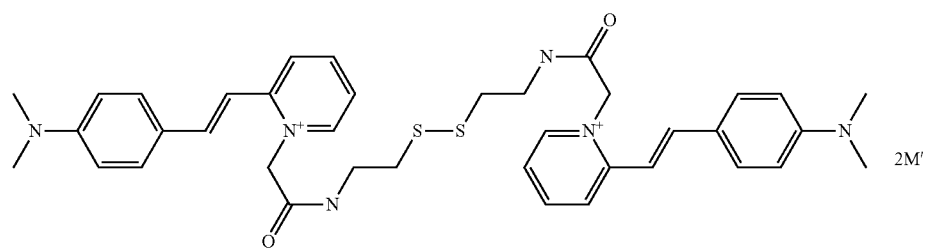
2M′
47
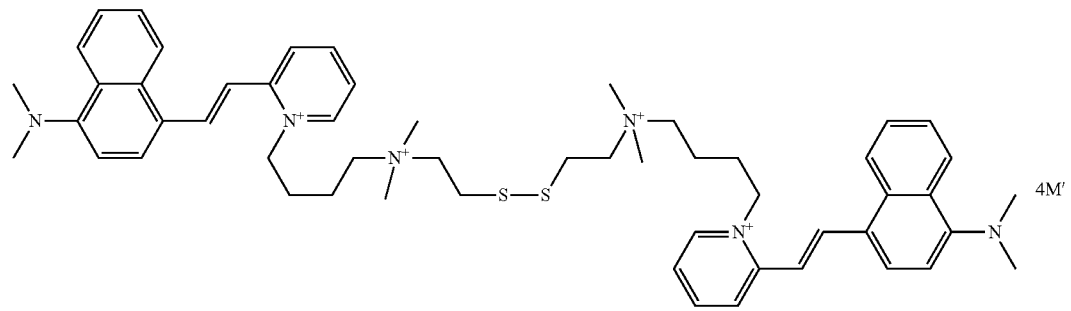
4M′
48
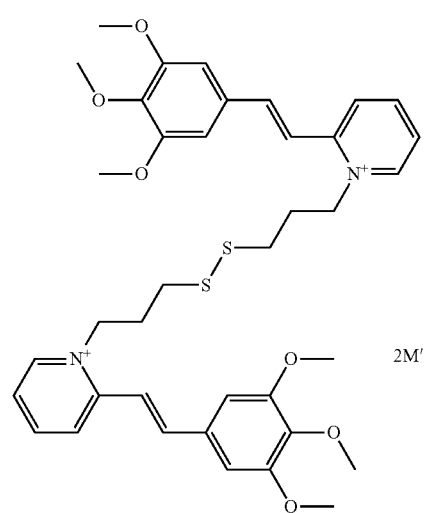
2M′

-continued
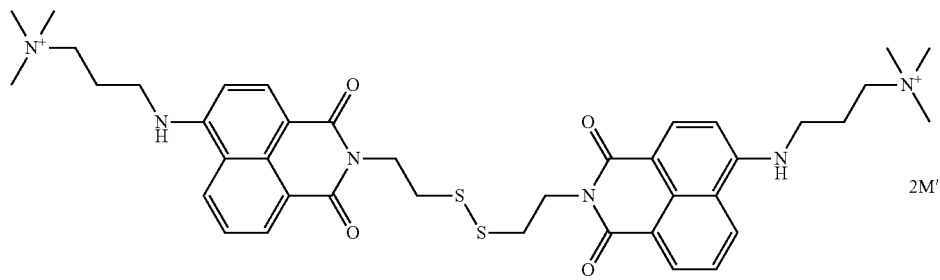
49
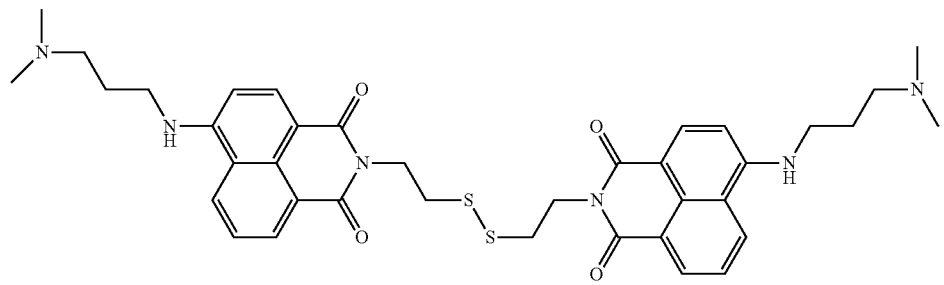
49a
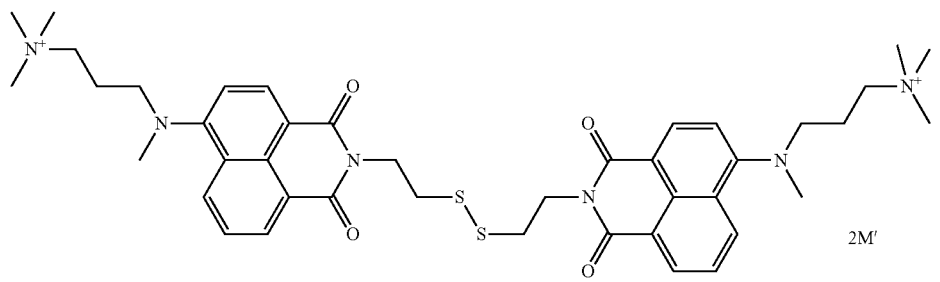
50
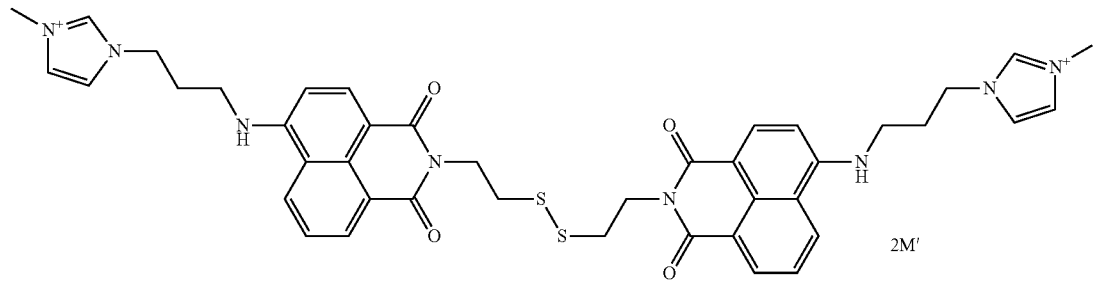
51
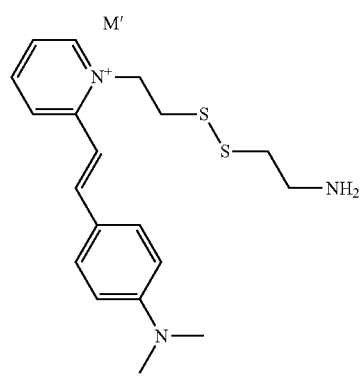
52
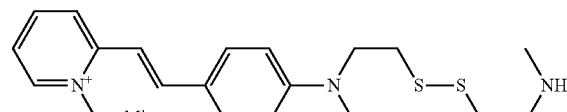
53

-continued
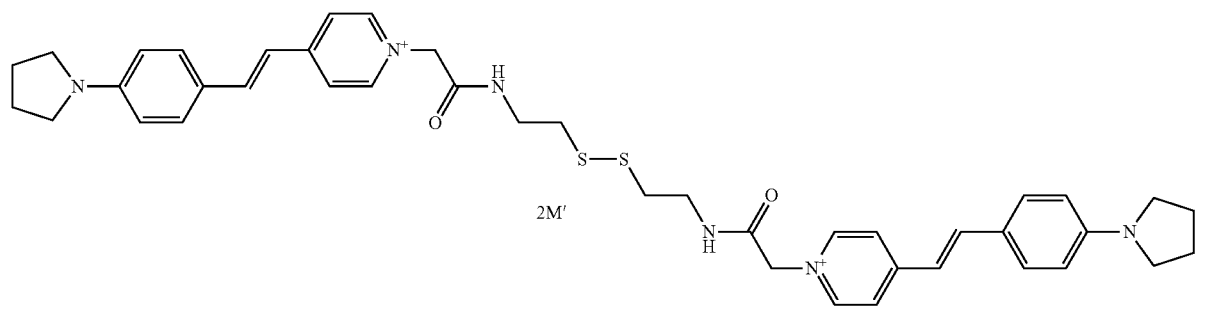
54
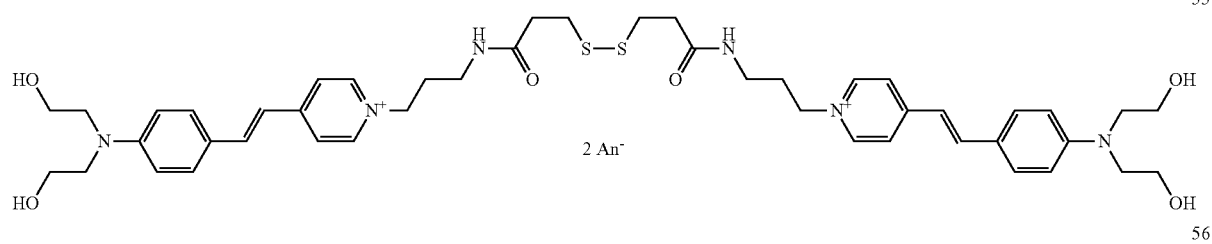
55
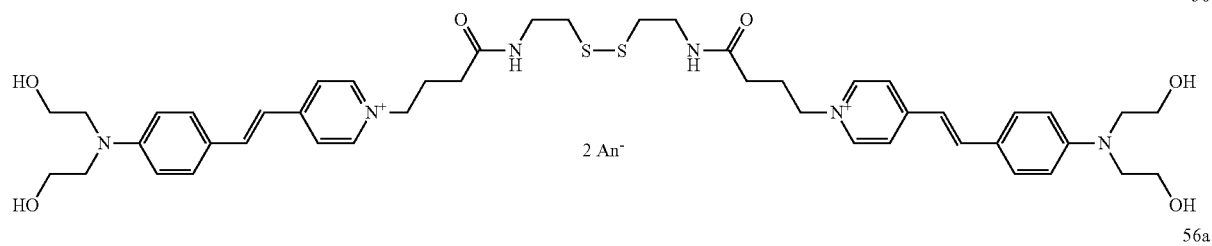
56
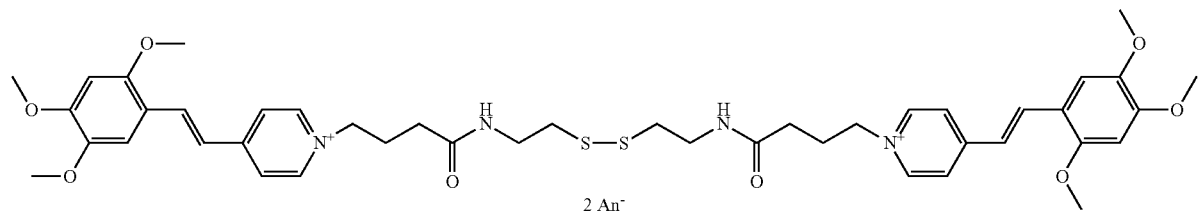
56a
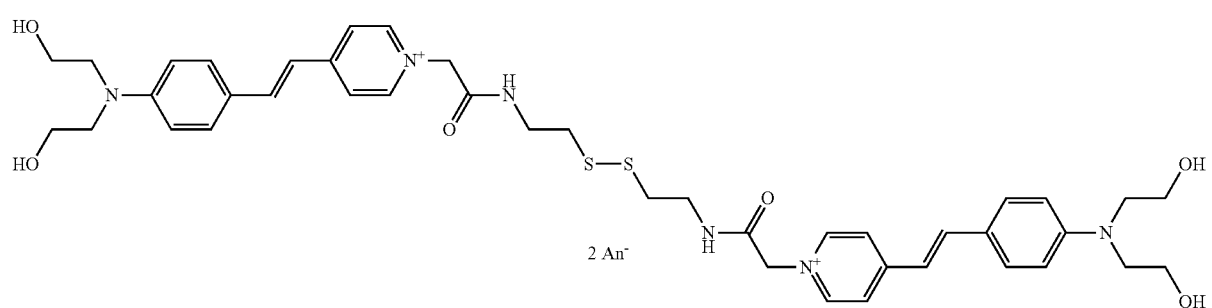
57
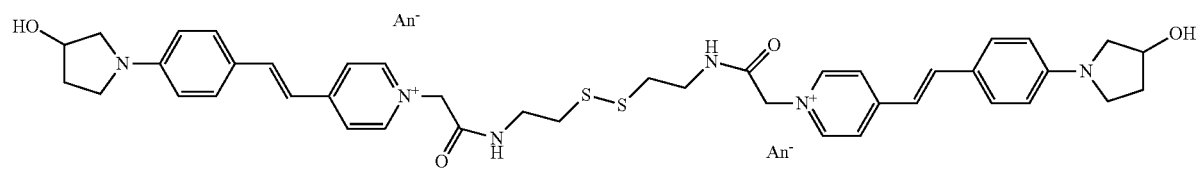
58

59
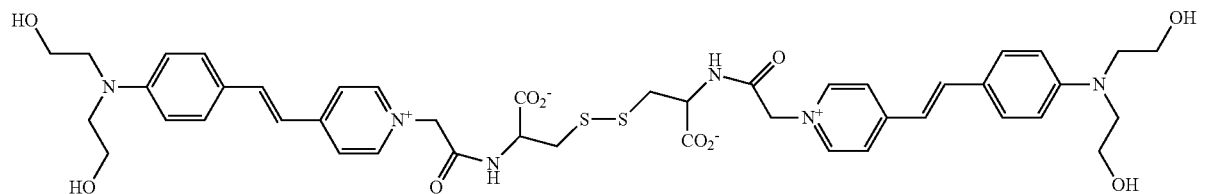
60
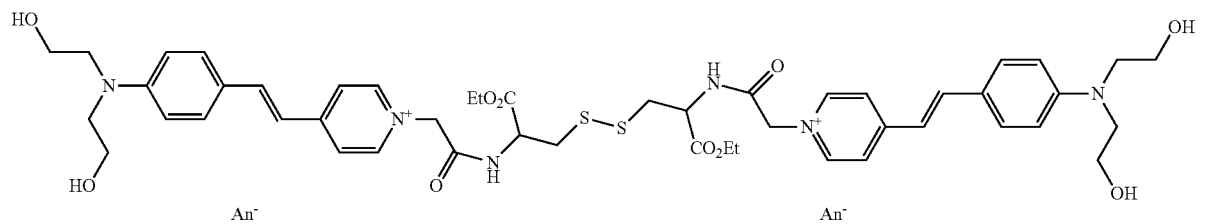
61
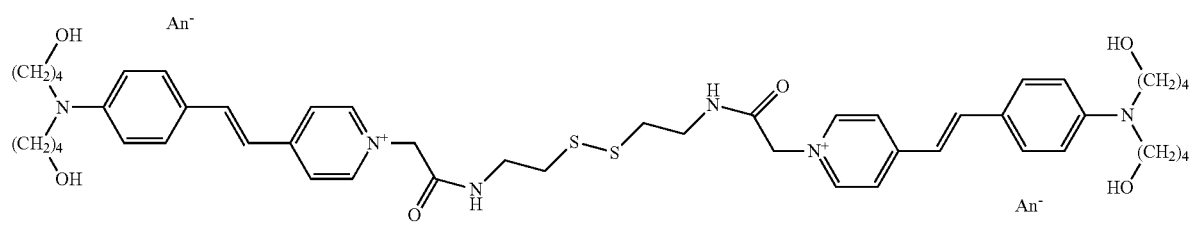
62
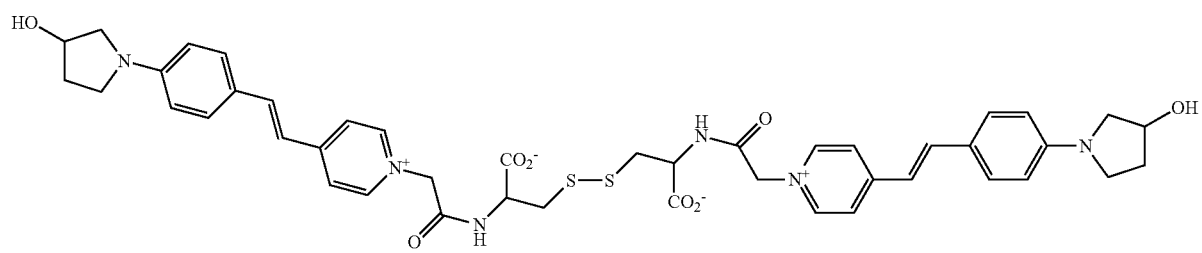
63
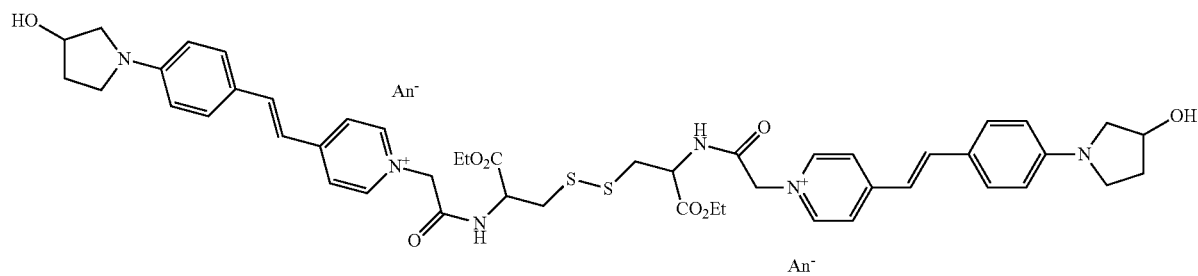
64
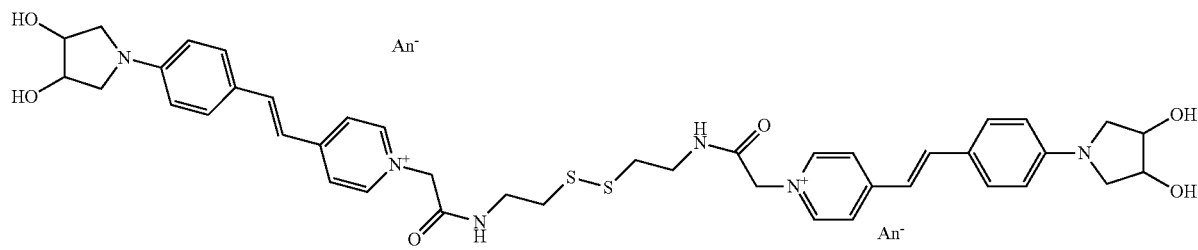

-continued
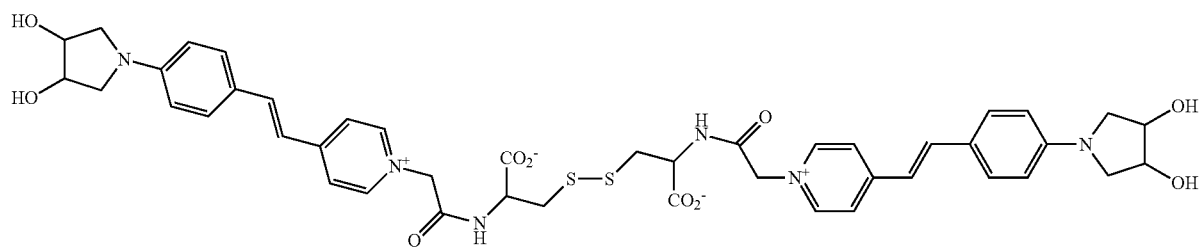
65
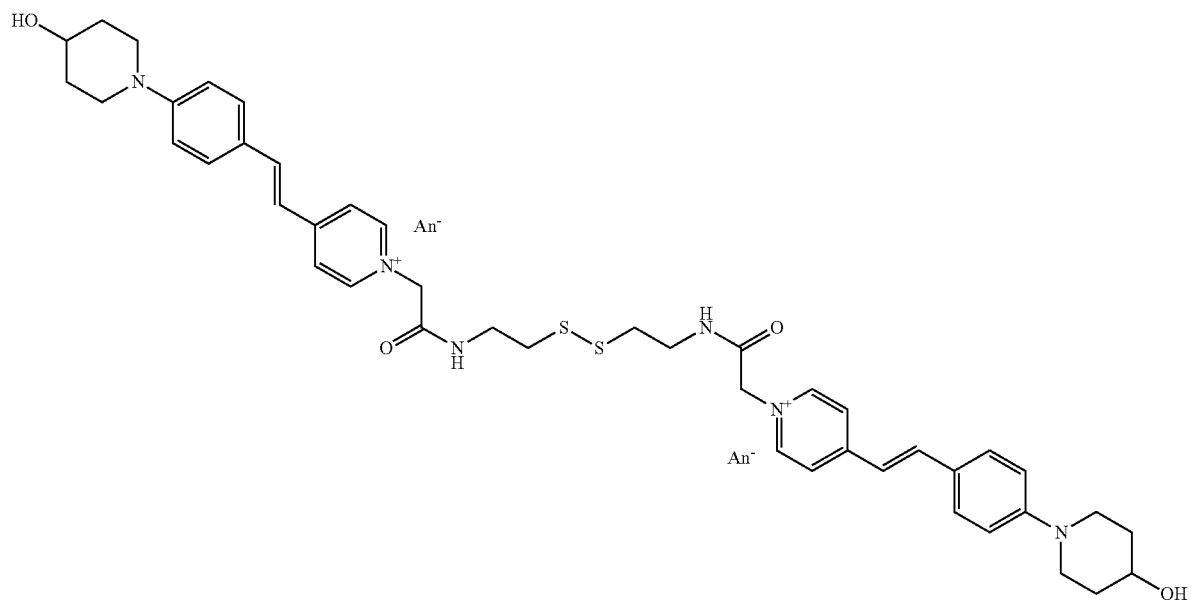
67
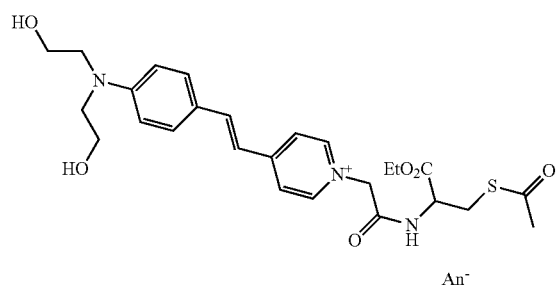
68
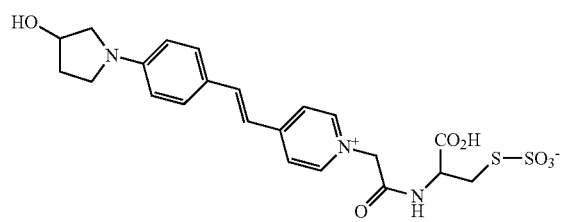
69
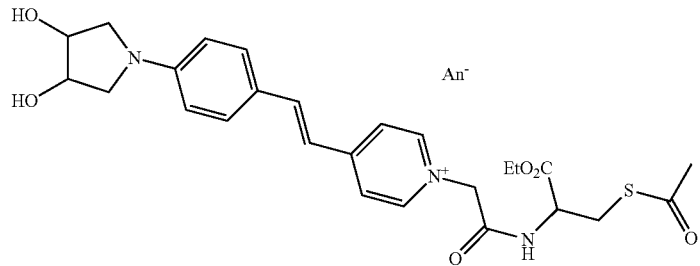
70

71
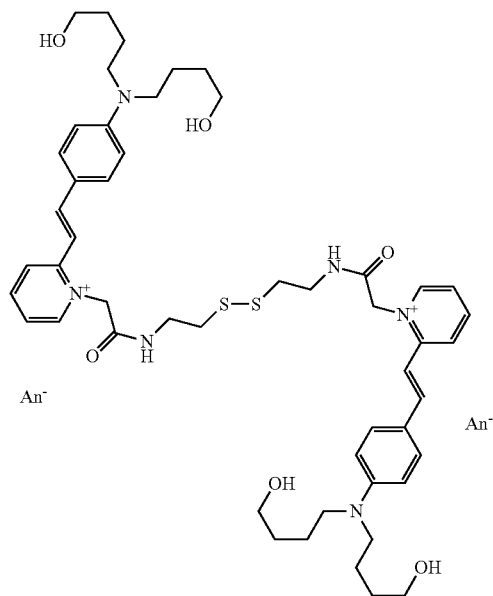
72
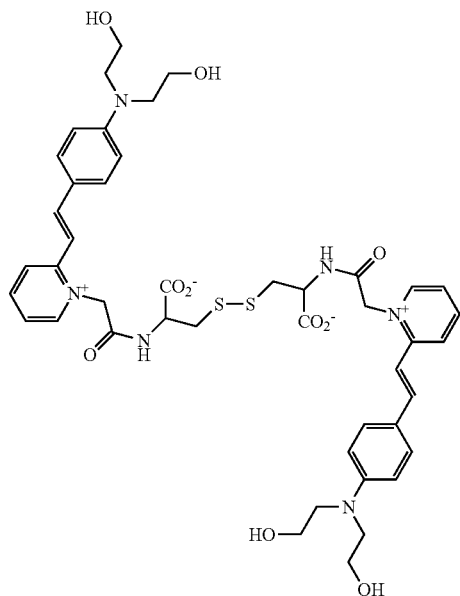
73
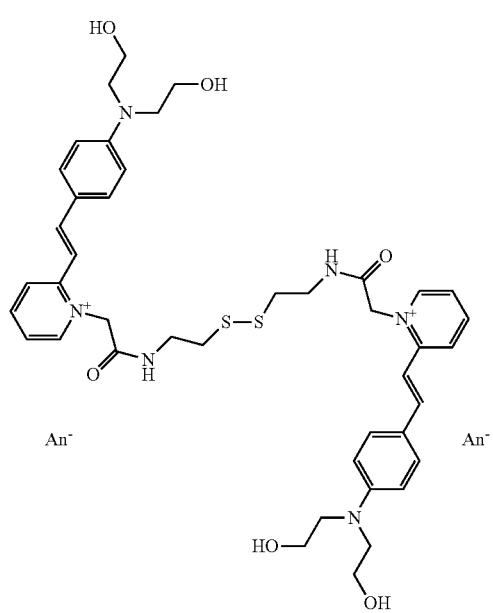
74
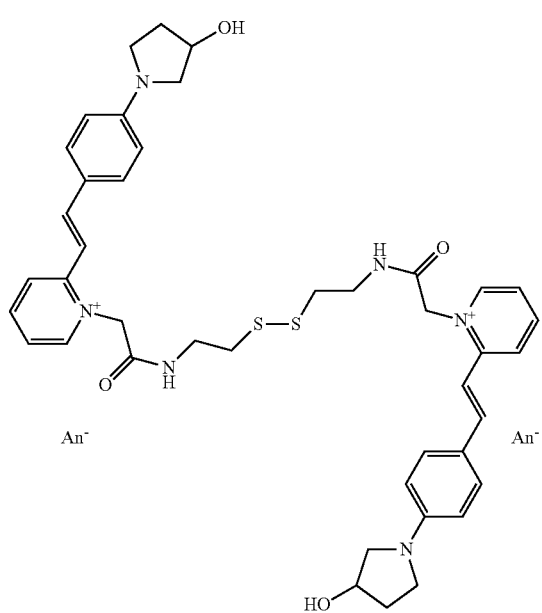

75
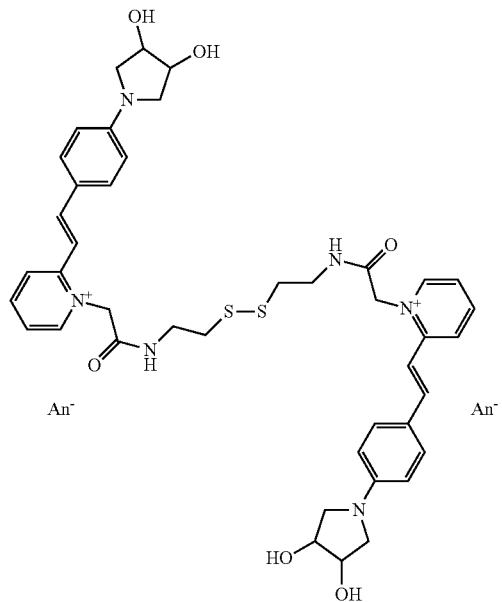
76
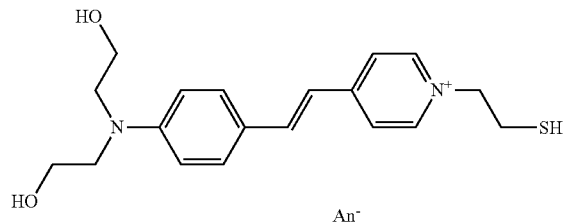
77
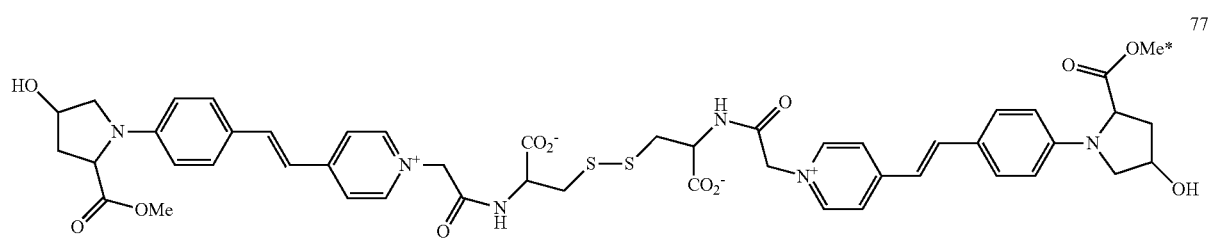
Me⁺ represents an alkali metal or ½ an alkaline-earth metal; or a methyl
78
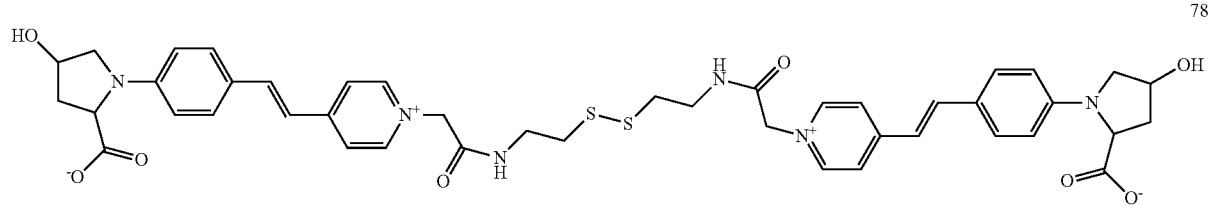

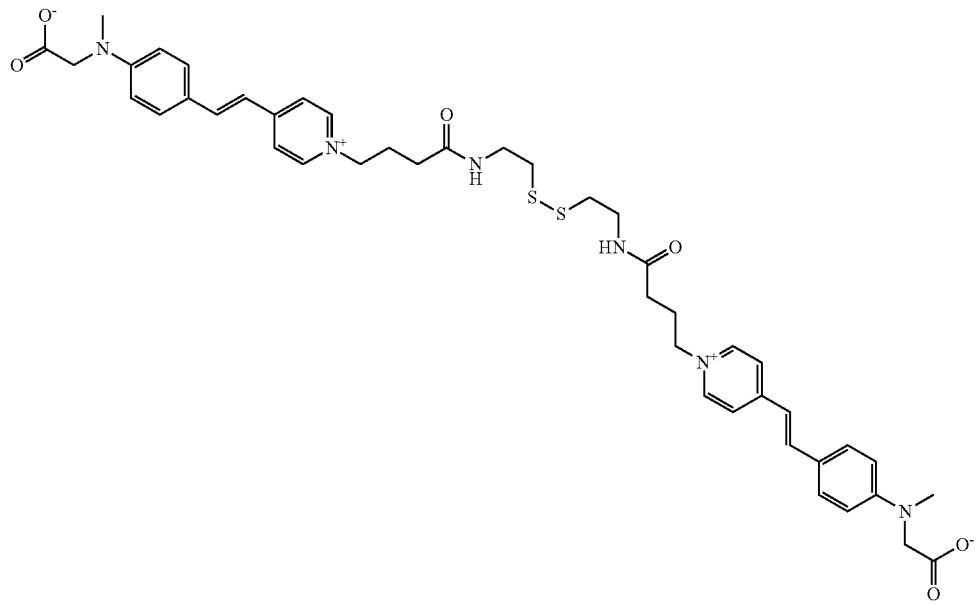
81
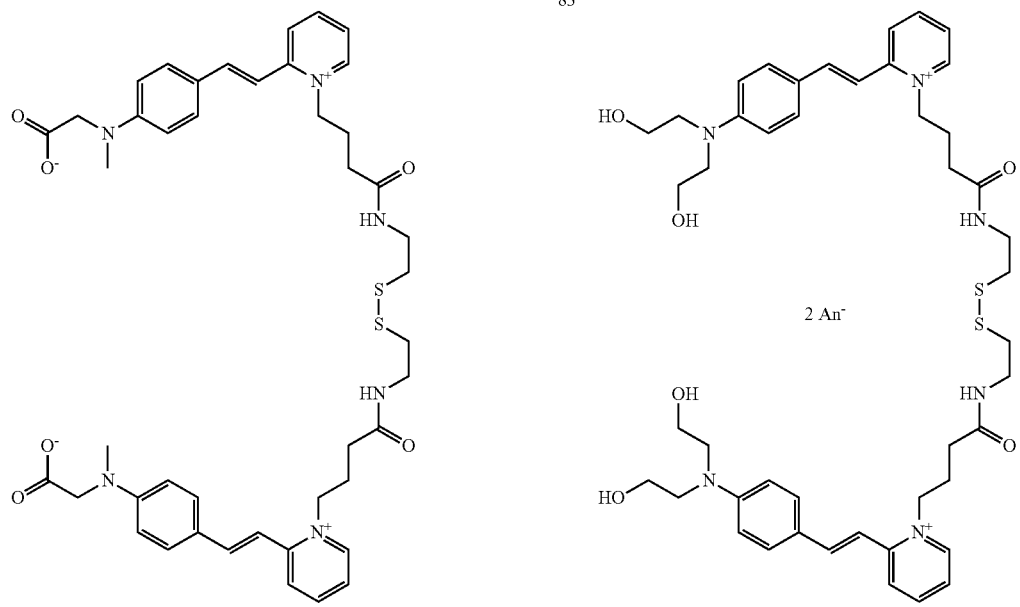
83
84
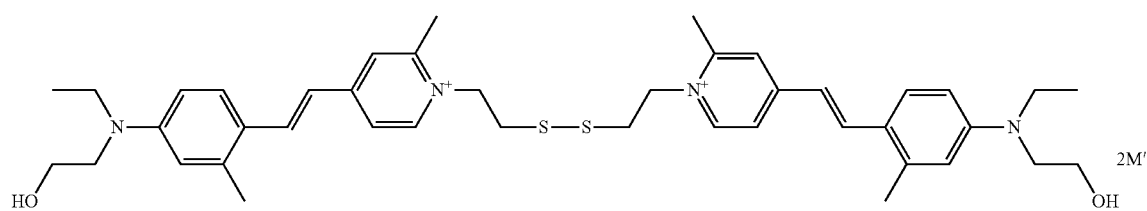
86
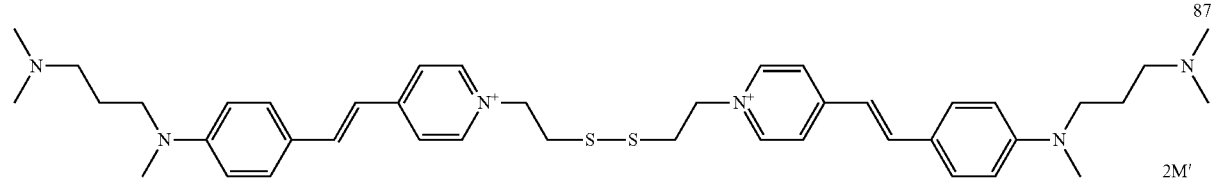
87

-continued
| 133 | 134 |
|---|---|
| 88 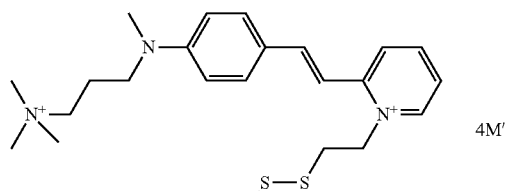 4M′ | 89 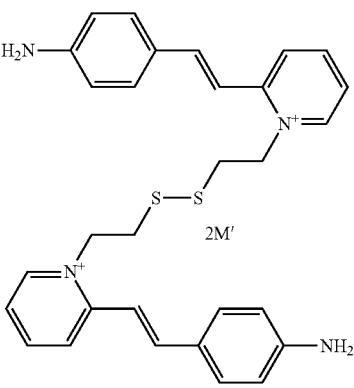 2M′ |
| 92 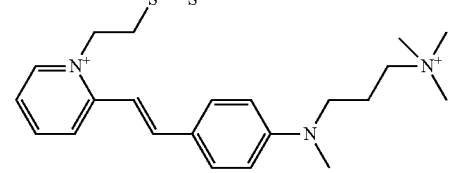 4M′ | 93 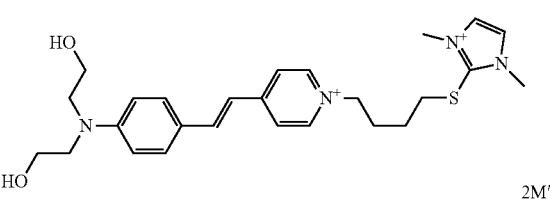 2M′ |
| | 94 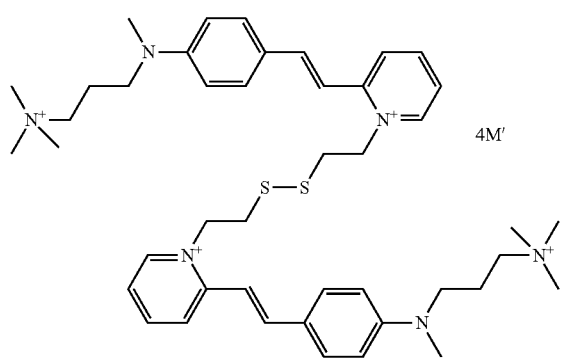 2M′ |
| | 95 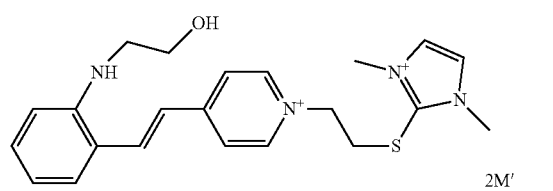 2M′ |
| 98 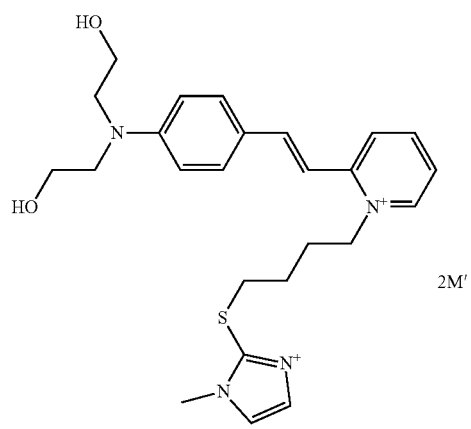 2M′ | 99 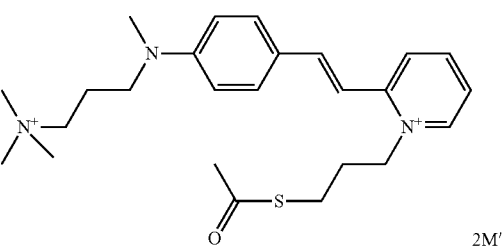 2M′ |
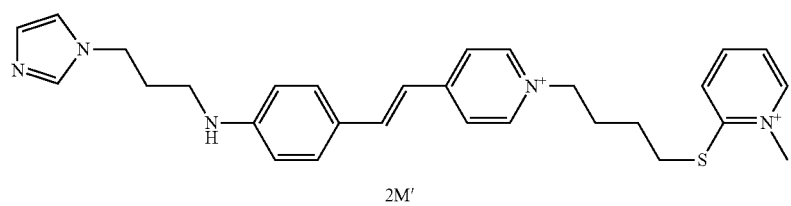

-continued
100
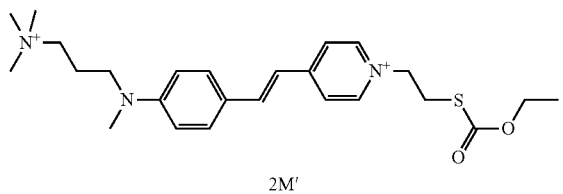
2M'
101
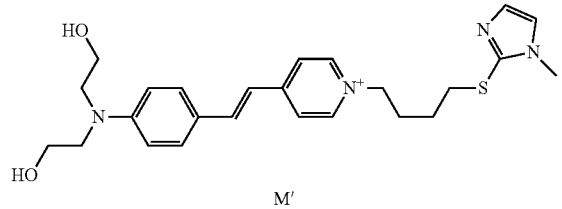
M'
102
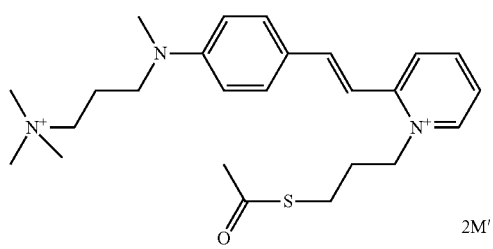
2M'
102
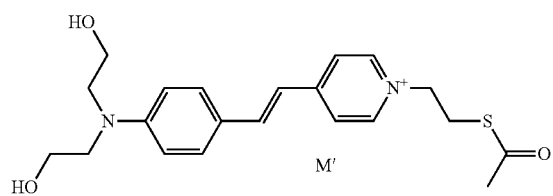
M'
104
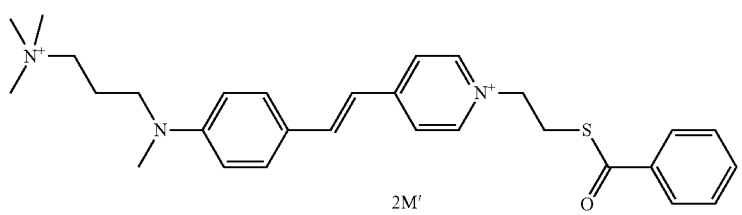
2M'
105
M'
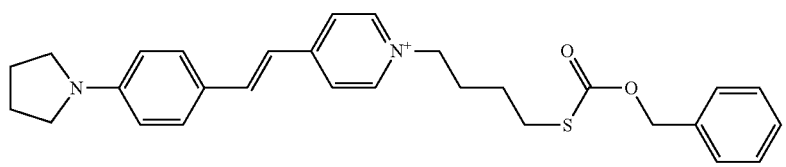
106
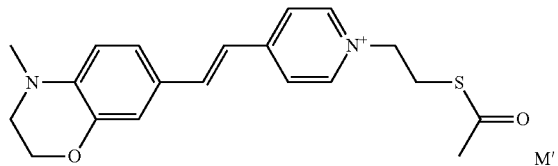
M'
107
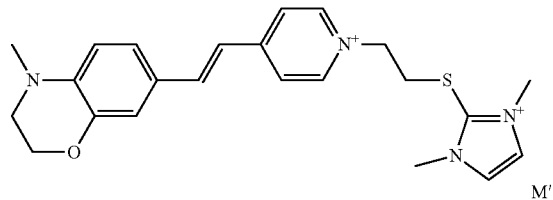
M'
108
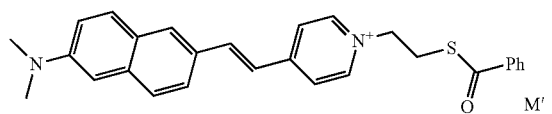
M'
109
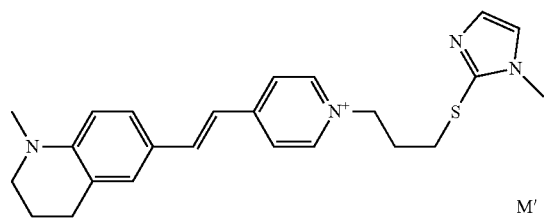
M'

-continued
110
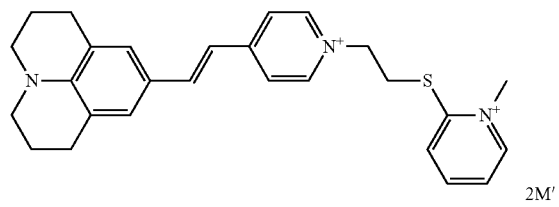
2M'
111
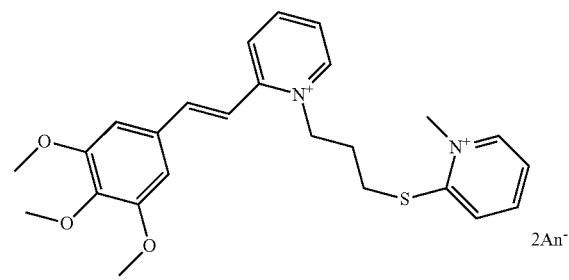
2An⁻
112
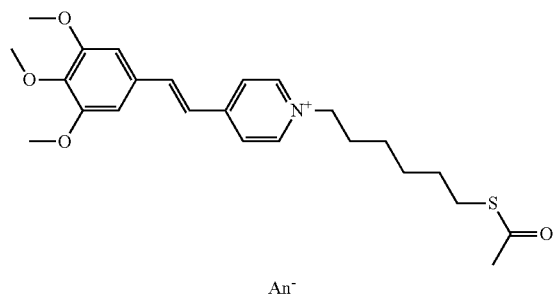
An⁻
113
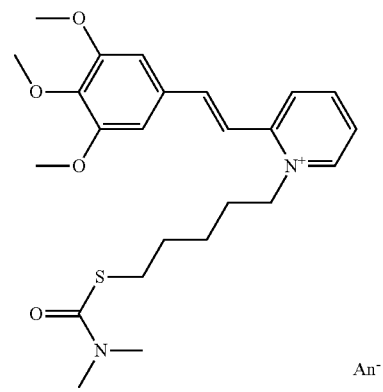
An⁻
114
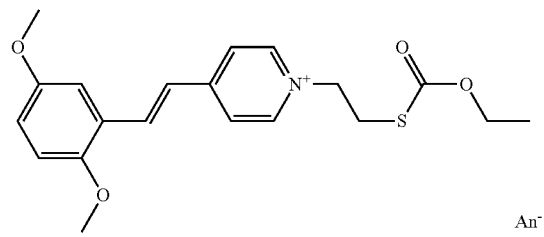
An⁻
115
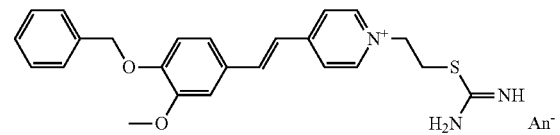
An⁻
116
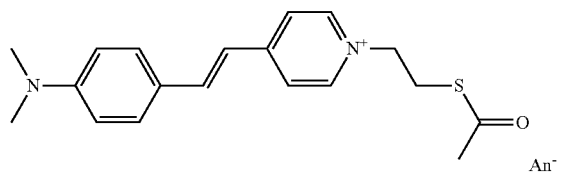
An⁻
117
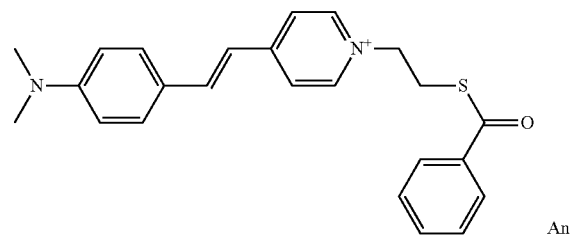
An⁻
118
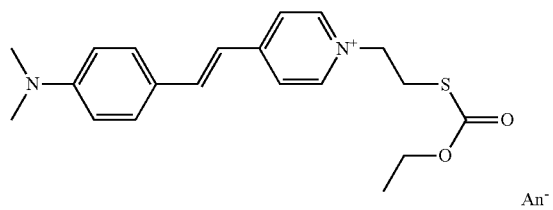
An⁻
119
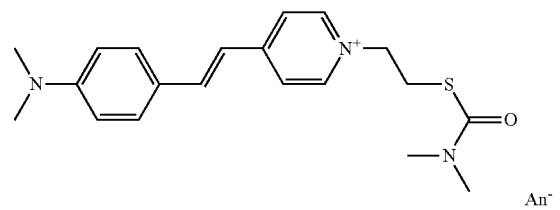
An⁻

-continued

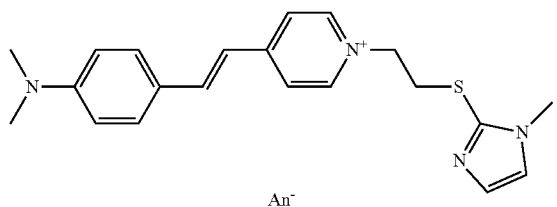
120 wherein An⁻ and M', which may be identical or different, represent anionic counterions.

10. The process according to claim 1, wherein the total amount of the at least one disulfide, thiol or protected-thiol fluorescent dye is between 0.001% and 30%, relative to the total weight of the composition in which it is present.

11. The process according to claim 1, wherein the process further comprises applying to said keratin fibers at least one reducing agent, wherein the at least one reducing agent is applied before, simultaneously with, or after the application of the at least one direct dye and/or the at least one disulfide, thiol, or protected-thiol fluorescent dye.

12. The process according to claim 1, wherein said process does not use any reducing agent.

13. The process according to claim 1, wherein the at least one direct dye and the at least one disulfide, thiol or protected-thiol fluorescent dye are applied jointly in the same composition to the keratin fibers.

14. The process according to claim 1, wherein the process comprises at least the two successive steps below:
 a first step of applying to said keratin fibers a cosmetic composition comprising the at least one disulfide, thiol or protected-thiol fluorescent dye followed by
 a second step of applying to said fibers a cosmetic composition comprising the at least one direct dye; or
 a first step of applying to said keratin fibers a cosmetic composition comprising the at least one direct dye, followed by
 a second step of applying to said fibers a cosmetic composition comprising the at least one disulfide, thiol or protected-thiol fluorescent dye.

15. The process according to claim 1, wherein the process further comprises application to said keratin fibers of at least one oxidizing agent applied after application of the at least one direct dye, and the at least one disulfide, thiol, or protected-thiol fluorescent dye.

16. The process according to claim 1, wherein the pH of a cosmetic composition comprising the at least one direct dye and/or the at least one disulfide, thiol or protected-thiol fluorescent dye is between 2 and 12.

17. The process according to claim 11, wherein the composition comprising the at least one reducing agent further comprises at least two alkaline agents, wherein the alkaline agents are different from one another.

18. A cosmetic composition comprising at least one direct dye, and at least one disulfide, thiol, or protected-thiol fluorescent dye, wherein the composition optionally comprises one or more reducing agents, and optionally having a pH of between 2 and 12;
 wherein the at least one direct dye is different from the at least one disulfide, thiol, or protected-thiol direct fluorescent dye; and
 wherein the at least one direct dye is present in a total amount ranging from 0.0001% to 30%, relative to the total weight of the cosmetic composition in which it is present.

19. A multi-compartment device comprising:
 either a first compartment comprising at least one direct dye, and a second compartment comprising at least one disulfide, thiol, or protected-thiol fluorescent dye; optionally a third compartment comprising one or more reducing agents, and optionally another compartment comprising one or more oxidizing agents;
 or a first compartment comprising at least one direct dye, and at least one disulfide, thiol, or protected-thiol fluorescent dye; optionally a second compartment comprising at least one reducing agent, and optionally another, third, compartment comprising at least one oxidizing agents;
 wherein the at least one direct dye is different from the at least one disulfide, thiol, or protected-thiol direct fluorescent dye; and
 wherein the at least one direct dye is comprised in a cosmetic composition, and is present in a total amount ranging from 0.0001% to 30%, relative to the total weight of the cosmetic composition in which it is present.

* * * * *

UNITED STATES PATENT AND TRADEMARK OFFICE
CERTIFICATE OF CORRECTION

| | | |
|---|---|---|
| PATENT NO. | : 11,096,880 B2 | Page 1 of 1 |
| APPLICATION NO. | : 16/622264 | |
| DATED | : August 24, 2021 | |
| INVENTOR(S) | : Samira Rharbi et al. | |

It is certified that error appears in the above-identified patent and that said Letters Patent is hereby corrected as shown below:

In the Claims

Claim 5, Column 103, Line 7, please change "Ar-O-S(O)2-" to -- Ar-O-S(O)$2^-$ --.

Claim 5, Column 106, Line 16, please add -- wherein: --.

Signed and Sealed this
Twenty-first Day of February, 2023

Katherine Kelly Vidal
*Director of the United States Patent and Trademark Office*